United States Patent [19]

Hamanaka et al.

[11] Patent Number: 5,770,594

[45] Date of Patent: Jun. 23, 1998

[54] NAPHTHYL-BENZOXAZEPINES OR -BENZOTHIAZEPINES AS SQUALENE SYNTHETASE INHIBITORS

[75] Inventors: Ernest S. Hamanaka, Gales Ferry, Conn.; Cheryl M. Hayward, North Providence, R.I.; Joel M. Hawkins, Old Lyme, Conn.

[73] Assignee: Pfizer Inc., New York, N.Y.

[21] Appl. No.: 860,155

[22] PCT Filed: Jun. 2, 1995

[86] PCT No.: PCT/IB95/00424

§ 371 Date: Jun. 17, 1997

§ 102(e) Date: Jun. 17, 1997

[87] PCT Pub. No.: WO96/20184

PCT Pub. Date: Jul. 4, 1996

Related U.S. Application Data

[63] Continuation of Ser. No. 362,713, Dec. 23, 1994, abandoned.

[51] Int. Cl.$^6$ .......................... A61K 31/55; C07D 267/14; C07D 281/10; C07D 281/08

[52] U.S. Cl. ........................... 514/211; 540/490; 540/488; 540/548; 540/552

[58] Field of Search .................................... 540/490, 488, 540/548, 552; 514/211

[56] References Cited

FOREIGN PATENT DOCUMENTS

| | | |
|---|---|---|
| 567026 | 10/1993 | European Pat. Off. . |
| 645378 | 3/1995 | European Pat. Off. . |
| 96-09827 | 10/1996 | WIPO . |

*Primary Examiner*—Mark L. Berch
*Attorney, Agent, or Firm*—Peter C. Richardson; Gregg C. Benson; A. Dean Olson

[57] ABSTRACT

This invention relates to certain benzoxazepinones and benzothiazepinones useful as hypocholesterolemic agents and antiatherosclerosis agents.

67 Claims, No Drawings

NAPHTHYL-BENZOXAZEPINES OR -BENZOTHIAZEPINES AS SQUALENE SYNTHETASE INHIBITORS

This application was filed under 35 U.S.C. §371 based on PCT/IB95/00424, which was filed on Jun. 2, 1995 which is a continuation of U.S. application Ser. No. 08/362,713 which was filed on Dec. 23, 1994 and is now abandoned.

BACKGROUND OF THE INVENTION

This invention relates to cholesterol synthesis inhibitors, pharmaceutical compositions containing such inhibitors and the use of such inhibitors to treat hypercholesterolemia and atherosclerosis in mammals.

Plasma cholesterol levels have been positively correlated with the incidence of clinical events associated with coronary heart disease (CHD). Thus, pharmacological interventions that reduce cholesterol levels in mammals have a beneficial effect on CHD. In particular, decreased plasma low density lipoprotein (LDL) cholesterol levels are associated with decreased atherosclerosis and a decreased risk of CHD, and hypolipidemic agents used in either monotherapy or combination therapy are effective at reducing plasma LDL cholesterol levels and the subsequent risk of CHD.

Cholesterol metabolism in mammals involves a series of pathways including cholesterol absorption in the small intestine, cholesterol biosynthesis in numerous tissues (primarily the liver and small intestine), bile acid biosynthesis in the liver and reabsorption in the small intestine, synthesis of cholesterol-containing plasma lipoproteins by the liver and intestine, catabolism of the cholesterol-containing plasma lipoproteins by the liver and extrahepatic tissues and secretion of cholesterol and bile acids by the liver.

Cholesterol synthesis occurs in multiple tissues, but principally in the liver and the intestine. It is a multistep process starting from acetyl-coenzyme A catalyzed by a series of enzymes including hydroxymethylglutaryl-coenzyme A (HMG-CoA) reductase, HMG-CoA synthase, squalene synthetase, squalene epoxidase, squalene cyclase and lanosterol demethylase. Inhibition of catalysis of these enzymes or blocking HMG-CoA reductase gene expression is recognized as an effective means to reduce cholesterol biosynthesis (thus they are referred to as cholesterol synthesis inhibitors) and can lead to a reduction in cholesterol levels. For example, there are known HMG-CoA reductase inhibitors (e.g., lovastatin, simvastatin, pravastatin, fluvastatin) that are used for the treatment of hypercholesterolemia.

Recently adopted National Cholesterol Education Program guidelines recommend aggressive lipid-lowering therapy for patients with pre-existing cardiovascular disease or for those with multiple factors that place them at increased risk.

The term squalene synthetase inhibitor refers to compounds that inhibit the condensation of 2 molecules of farnesylpyrophosphate to form squalene, a reaction that is catalyzed by the enzyme squalene synthetase. Such inhibition is readily determined by those skilled in the art according to standard assays (Meth. Enzymol. 1969; 15: 393–454 and Meth. Enzymol. 1985; 110:359–373 and references contained therein). A summary of squalene synthetase inhibitors has been compiled (Curr. Op. Ther. Patents (1993) 861-4). European patent publication 0 567 026 A1 discloses 4,1-benzoxazepine derivatives as squalene synthase inhibitors and their use in the treatment of hypercholesterolemia and as fungicides. European patent publication 0 645 378 A1 discloses condensed seven- or eight-membered heterocycles as squalene synthetase inhibitors and their use in treatment and prevention of hypercholesterolemia and fungal infections. European patent publication 0 645 377 A1 discloses benzoxazepine derivatives as squalene synthetase inhibitors useful for the treatment of hypercholesterolemia or coronary sclerosis. European patent publication 0 611 749 A1 discloses substituted amic acid derivatives useful for treatment of arteriosclerosis.

Thus, although there are a variety of hypercholesterolemia therapies, there is a continuing need and a continuing search in this field of art for alternative therapies.

SUMMARY OF THE INVENTION

This invention is directed to cholesterol synthesis inhibitor compounds of Formula I useful for the treatment of hypercholesterolemia and atherosclerosis.

The compounds of this invention have the formula

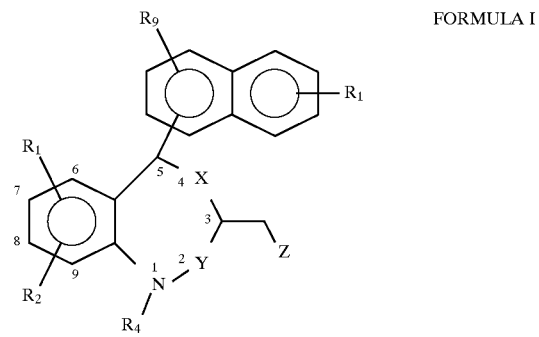

FORMULA I and the pharmaceutically acceptable cationic and anionic salts, prodrugs and stereoisomers thereof wherein X is oxy, thio, —S(O)— or —S(O)$_2$—;

Y is carbonyl or methylene;

$R_1$, $R_2$, $R_3$ and $R_9$ are each independently hydrogen, halo, hydroxyl, trifluoromethyl, ($C_1$–$C_4$)alkyl, fluorinated ($C_1$–$C_4$)alkyl having from 1 to 9 fluorines, ($C_1$–$C_4$) alkoxy, fluorinated ($C_1$–$C_4$)alkoxy having from 1 to 9 fluorines, ($C_1$–$C_4$)alkylthio, ($C_1$–$C_4$)alkylsulfinyl, ($C_1$–$C_4$)alkylsulfonyl, phenyl, amino, mono-N- or di-N,N-($C_1$–$C_4$)alkylamino, carboxyl, ($C_1$–$C_4$) alkoxylcarbonyl, carbamoyl, mono-N- or di-N,N-($C_1$–$C_4$)alkylcarbamoyl, ($C_1$–$C_4$)alkanoylamino, fluorinated ($C_1$–$C_4$)alkanoylamino having from 1 to 9 fluorines, ($C_1$–$C_4$)alkylsulfonylamino or fluorinated ($C_1$–$C_4$)alkylsulfonylamino having from 1 to 9 fluorines, ($C_1$–$C_6$)alkanoyl, ($C_1$–$C_4$)alkanoyl($C_1$–$C_6$) alkyl, oxazolyl, thiazolyl, isoxazolyl, pyrazolyl or isothiazolyl wherein said preceding heterocycles are carbon linked and wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is ($C_1$–$C_7$)alkyl or ($C_3$–$C_4$)cycloalkylmethyl;

Z is carboxyl, ($C_1$–$C_4$)alkoxycarbonyl, aminocarbonyl, cyano, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl,

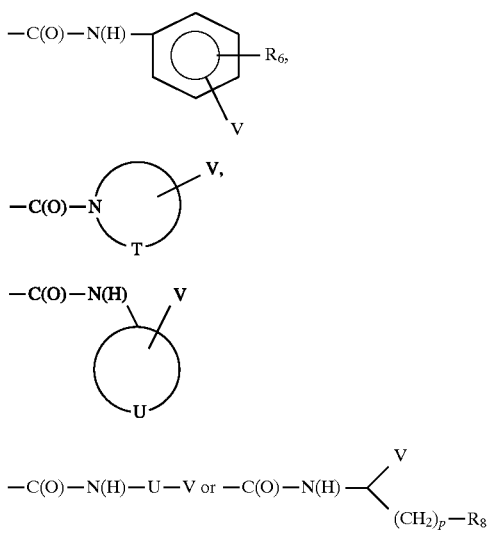

—C(O)—N(H)—U—V or —C(O)—N(H)—\<^{V}_{(CH_2)_p—R_8}

$R_5$ is amino or mono-N- or di-N,N-$(C_1-C_4)$alkylamino; $(C_1-C_4)$alkyl optionally substituted with 1 to 9 fluorines, amino, mono-N- or di-N,N-$(C_1-C_4)$ alkylamino, carboxyl, $(C_1-C_4)$alkoxycarbonyl, carbamoyl or mono-N- or di-N,N-$(C_1-C_4)$ alkylcarbamoyl; phenyl optionally mono- or di-substituted independently with methyl, methoxyl, fluoro, trifluoromethoxyl, carboxyl, $(C_1-C_4)$ alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or thiazolyl, isothiazolyl, thienyl, furyl, pyridinyl or such heterocycles optionally mono-substituted by carboxyl, or mono- or di-substituted with methyl;

$R_6$ is hydrogen, hydroxyl or methoxyl;

T forms a five to seven membered mono-aza, saturated ring, said ring optionally containing thio and said ring optionally mono-substituted on carbon with hydroxyl;

U forms a three to seven membered saturated carbocyclic ring;

V is —$CO_2R_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl;

$R_7$ is hydrogen or $(C_1-C_4)$alkyl;

p is 1, 2, 3 or 4;

$R_8$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$ alkylsulfinyl, mono-N- or di-N,N-$(C_1-C_4)$ alkylcarbamoyl, mono-N- or di-N,N-$(C_1-C_4)$ alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$ alkanoylamino having from 1 to 9 fluorines, mono-N- or di-N,N-$(C_1-C_4)$alkylaminosulfonyl, ureido, mono-N- or di-N,N-$(C_1-C_4)$ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl.

A first group of preferred compounds of Formula I consists of those compounds wherein $R_1$, $R_2$, $R_3$ and $R_9$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$ alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$ alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

Z is carboxyl, $(C_1-C_4)$alkoxycarbonyl, hydroxyaminocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl,

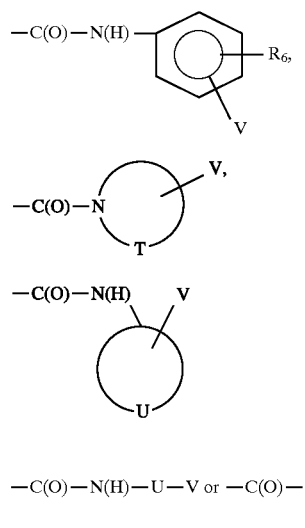

—C(O)—N(H)—U—V or —C(O)—N(H)—\<^{V}_{(CH_2)_p—R_8}

T forms a five to seven membered mono-aza, saturated ring optionally substituted with hydroxyl; and V is —$CO_2R_7$, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl.

Within this first group of preferred compounds of Formula I is a first group of especially preferred compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$ and $R_9$ are H;

X is oxy;

Y is carbonyl;

V is —$CO_2R_7$; and

Z is carboxyl, tetrazol-5-yl,

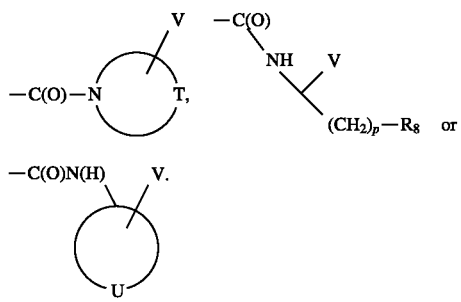

Within the preceding first group of especially preferred compounds is a first group of particularly preferred compounds wherein $R_1$ and $R_2$ are each independently hydrogen, halo, $(C_1-C_4)$alkyl, $(C_1-C_4)$alkoxy, hydroxy or trifluoromethyl; and Z is carboxyl,

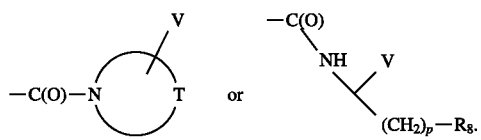

Preferred within the immediately preceding particularly preferred compounds are compounds wherein T forms a piperidin-1-yl ring; and $R_8$ is carboxyl or alkylthio.

Particular compounds within the immediately preceding group are compounds wherein:

a. $R_4$ is neopentyl;
 $R_1$ is 7-chloro;
 $R_2$ is H; and
 Z is carboxyl;

b. $R_4$ is neopentyl;
 $R_1$ is 7-chloro;
 $R_2$ is H; and
 Z is 4-carboxylpiperidin-1-yl-carbonyl;

c. $R_4$ is neopentyl;
 $R_1$ is 7-chloro;
 $R_2$ is H; and
 Z is 3-carboxylpiperidin-1-yl-carbonyl;

d. $R_4$ is neopentyl;
 $R_1$ is 7-chloro;
 $R_2$ is H;
 V is $—CO_2R_7$;
 Z is

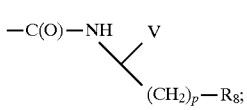

$R_7$ is methyl;
$R_8$ is carboxyl; and
p is 1;

e. $R_4$ is neopentyl;
 $R_1$ is 7-chloro;
 $R_2$ is H;
 V is $-CO_2R_7$;
 Z is

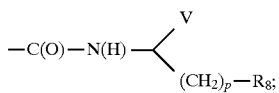

$R_7$ is methyl;
$R_8$ is carboxyl; and
p is 2;

f. $R_4$ is neopentyl;
 $R_1$ is 7-chloro;
 $R_2$ is H;
 V is $—CO_2R_7$;
 Z is

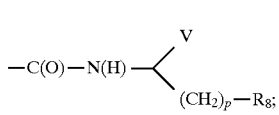

$R_7$ is H;
$R_8$ is thiomethyl; and
p is 1; or g. $R_4$ is neopentyl;
 $R_1$ is 7-chloro;
 $R_2$ is H; and
 Z is 4-ethoxycarbonylpiperidin-1-yl-carbonyl.

Especially preferred trans stereoisomers are (–)-trans-7-chloro-5-(1-naphthyl)-1-neopentyl-2-oxo-1,2,3,5-tetrahydro-4,1-benzoxazepin-3-acetic acid, (–)-N-(trans-7-chloro-5-(1-naphthyl)-1-neopentyl-2-oxo-1,2,3,5-tetrahydro-4,1-benzoxazepin-3-acetyl)-isonipecotic acid, (–)-N-(trans-7-chloro-5-(1-naphthyl)-1-neopentyl-2-oxo-1,2,3,5-tetrahydro-4,1-benzoxazepin-3-acetyl)-nipecotic acid, (–)-N-[trans-7-chloro-5-(1-naphthyl)-1-neopentyl-2-oxo-1,2,3,5-tetrahydro-4,1-benzoxazepin-3-acetyl]-(–)-nipecotic acid, (–)-N-(trans-7-chloro-5-(1-naphthyl)-1-neopentyl-2-oxo-1,2,3,5-tetrahydro-4,1-benzoxazepin-3-acetyl)-L-aspartic acid-α-methyl ester, (–)-N-(trans-7-chloro-5-(1-naphthyl)-1-neopentyl-2-oxo-1,2,3,5-tetrahydro-4,1-benzoxazepin-3-acetyl)-L-glutamic-α-methyl ester, (–)-N-(trans-7-chloro-5-(1-naphthyl)-1-neopentyl-2-oxo-1,2,3,5-tetrahydro-4,1-benzoxazepin-3-acetyl)-L-S-methylcysteine and Ethyl ester of (-)-N-trans-(7-chloro-5-(1-naphthyl)-1-neopentyl-2-oxo-1,2,3,5-tetrahydro-4,1-benzoxazepin-3-acetyl)-isonipecotic acid.

Other preferred compounds are

N-[trans-7-trifluoromethyl-5-(1-naphthyl)-1-neopentyl-2-oxo-1,2,3,5-tetrahydro-4,1-benzoxazepin-3-acetyl] isonipecotic acid, N-[trans-7-trifluoromethyl-5-(1-naphthyl)-1-neopentyl-2-oxo-1,2,3,5-tetrahydro-4,1-benzoxazepin-3-acetyl] nipecotic acid, N-[trans-7-trifluoromethyl-5-(1-naphthyl)-1-neopentyl-2-oxo-1,2,3,5-tetrahydro-4,1-benzoxazepin-3-acetyl]-L-proline, trans-7-methyl-5-(naphthalen-1-yl)-1-neopentyl-1,2,3,5-tetrahydro-2-oxo-4,1-benzoxazepine-3-acetic acid, N-[trans-7-methyl-5-(naphthalen-1-yl)-1-neopentyl-1,2,3,5-tetrahydro-2-oxo-4,1-benzoxazepine-3-acetyl] isonipecotic acid, N-[trans-7-methyl-5-(naphthalen-1-yl)-1-neopentyl-1,2,3,5-tetrahydro-2-oxo-4,1-benzoxazepine-3-acetyl] nipecotic acid, trans-7-methoxy-5-(naphthalen-1-yl)-1-neopentyl-1,2,3,5-tetrahydro-2-oxo-4,1-benzoxazepine-3-acetic acid, N-[trans-7-methoxy-5-(naphthalen-1-yl)-1-neopentyl-1,2,3,5-tetrahydro-2-oxo-4,1-benzoxazepine-3-acetyl] isonipecotic acid and N-[trans-7-methoxy-5-(naphthalen-1-yl)-1-neopentyl-1,2,3,5-tetrahydro-2-oxo-4,1-benzoxazepine-3-acetyl] nipecotic acid.

Another group of preferred stereoisomers is (−)-trans-7-trifluoromethyl-5-(1-naphthyl)-1-neopentyl-2-oxo-1,2,3,5-tetrahydro-4,1-benzoxazepin-3-acetic acid, (−)-N-[trans-7-chloro-5-(1-naphthyl)-1-neopentyl-2-oxo-1,2,3,5-tetrahydro-4,1-benzoxazepin-3-acetyl]-L-pipecolinic acid and (−)-N-[trans-7-chloro-5-(1-naphthyl)-1-neopentyl-2-oxo-1,2,3,5-tetrahydro-4,1-benzoxazepin-3-acetyl)-L-methionine.

Yet another group of preferred compounds is trans-7-methylthio-5-(1-naphthyl)-1-neopentyl-2-oxo-1,2,3,5-tetrahydro-4,1-benzoxazepin-3-acetic acid, trans-7-trifluoromethoxy-5-(1-naphthyl)-1-neopentyl-2-oxo-1,2,3,5-tetrahydro-4,1-benzoxazepin-3-acetic acid, trans-7,8ethylenedioxy-5-(1 -naphthyl)-1-neopentyl-2-oxo-1,2,3,5-tetrahydro-4,1-benzoxazepin-3-acetic acid, N-[trans-7-chloro-5-(1-naphthyl)-1-neopentyl-2-oxo-1,2,3,5-tetrahydro-4,1-benzoxazepin-3-acetyl]-1-amino-1-cyclopentanecarboxylic acid, N-[trans-7-chloro-5-(1-naphthyl)-1-neopentyl-2-oxo-1,2,3,5-tetrahydro-4,1-benzoxazepin-3-acetyl]-1-amino-1-cyclopropanecarboxylic acid and N-[trans-7-chloro-5-(1-naphthyl)-1-neopentyl-2-oxo-1,2,3,5-tetrahydro-4,1-benzoxazepin-3-acetyl]-4-azetidinecarboxylic acid.

Within the above first group of especially preferred compounds is a second group of particularly preferred compounds wherein T forms a 1,3-thiazolidine ring.

Preferred within this group of compounds is (−)-N-[trans-7-chloro-5-(1-naphthyl)-1-neopentyl-2-oxo-1,2,3,5-tetrahydro-4,1-benzothiazepin-3-acetyl]-(R)-thiazolidine-4-carboxylic acid.

Within the above first group of particularly preferred compounds are compounds wherein T forms a pyrrolidin-1-yl ring.

Within the immediately preceding group of compounds is a compound wherein $R_4$ is neopentyl;

$R_1$ is 7-chloro;

$R_2$ is H; and

Z is L-proline-N-carbonyl or D-proline-N-carbonyl, and two preferred stereoisomers thereof are (−)-N-(trans-7-chloro-5-(1-naphthyl)-1-neopentyl-2-oxo-1,2,3,5-tetrahydro-4,1-benzoxazepin-3-acetyl)-L-proline and (−)-N-[trans-7-chloro-5-(1-naphthyl)-1-neopentyl-2-oxo-1,2,3,5-tetrahydro-4,1-benzoxazepin-3-acetyl]-D-proline.

Within the first group of preferred compounds of Formula I is a second group of especially preferred compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy or trifluoromethyl;

$R_3$ and $R_9$ are H;

X is oxy;

Y is methylene;

V is —$CO_2R_7$; and

Z is carboxyl,

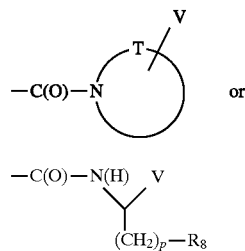

Within the above second group of especially preferred compounds is a first group of particularly preferred compounds wherein Z is

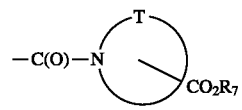

and T forms a piperidin-1-yl ring.

Particular compounds within the immediately preceding group are compounds wherein:

a. $R_4$ is neopentyl;

$R_1$ is 7-chloro;

$R_2$ is H; and

Z is 3-carboxylpiperidin-1-yl-carbonyl; and b. $R_4$ is neopentyl;

$R_1$ is 7-chloro;

$R_2$ is H; and

Z is 4-carboxylpiperidin-1-yl-carbonyl.

Particular stereoisomers of the immediately preceding compounds are (−)-N-(trans-7-chloro-5-(1-naphthyl)-1-neopentyl-1,2,3,5-tetrahydro-4,1-benzoxazepin-3-acetyl)-nipecotic acid and (−)-N-(trans-7-chloro-5-(1-naphthyl)-1-neopentyl-1,2,3,5-tetrahydro-4,1-benzoxazepin-3-acetyl)-isonipecotic acid.

Within the above first group of preferred compounds of Formula I is a third group of especially preferred compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$ and $R_9$ are H;

X is thio;

Y is carbonyl;

V is —$CO_2R_7$ or tetrazol-5-yl; and

Z is carboxyl, tetrazol-5-yl,

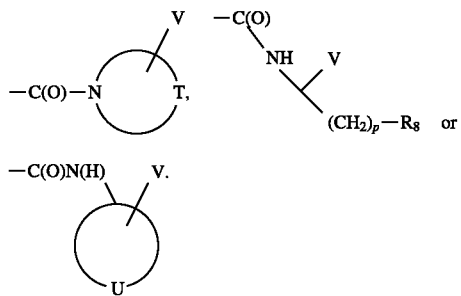

Within the above third group of especially preferred compounds are compounds wherein T forms a piperidin-1-yl ring.

Particular compounds within the immediately preceding group are trans-7-acetyl-5-(naphthalen-1-yl)-1-neopentyl-1,2,3,5-tetrahydro-2-oxo-4,1-benzothiazepine-3-acetic acid, N-[trans-7-acetyl-5-(naphthalen-1-yl)-1-neopentyl-1,2,3,5-tetrahydro-2-oxo-4,1-benzothiazepine-3-acetyl]isonipecotic acid, trans-7-chloro-5-(naphthalen-1-yl)-1-neopentyl-3-(1H-tetrazol-5-ylmethyl)-1,2,3,5-tetrahydro-4,1-benzothiazepin-2-one and trans-7-chloro-5-(naphthalen-1-yl)-1-neopentyl-3-{2-oxo-2-[4-(1H-tetrazol-5-yl)-piperidin-1-yl]-ethyl}-1,2,3,5-tetrahydro4,1-benzothiazepin-2-one.

Within the first group of preferred compounds of Formula I is a fourth group of especially preferred compounds wherein the $C^3$ and $C^5$ substituents are trans;

$R_1$ and $R_2$ are each independently hydrogen, halo, $(C_1-C_4)$alkyl, $(C_1-C_4)$alkoxy, hydroxy or trifluoromethyl;

$R_3$ and $R_9$ are H;

X is thio;

Y is carbonyl;

V is $CO_2$—$R_7$; and

Z is carboxyl,

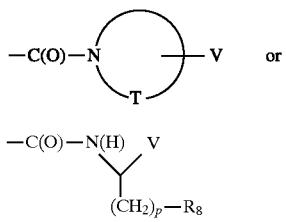

Within the fourth group of especially preferred compounds is a first group of particularly preferred compounds wherein T forms a piperidin-1-yl ring.

Within the immediately preceding group of compounds are trans-7-methyl-5-(naphthalen-1-yl)-1-neopentyl-1,2,3,5-tetrahydro-2-oxo-4,1-benzothiazepine-3-acetic acid, N-[trans-7-methyl-5-(naphthalen-1-yl)-1-neopentyl-1,2,3,5-tetrahydro-2-oxo-4,1-benzothiazepine-3-acetyl]isonipecotic acid, N-[trans-7-methyl-5-(naphthalen-1-yl)-1-neopentyl-1,2,3,5-tetrahydro-2-oxo-4,1-benzothiazepine-3-acetyl]nipecotic acid, trans-7-methoxy-5-(naphthalen-1-yl)-1-neopentyl-1,2,3,5-tetrahydro-2-oxo-4,1-benzothiazepine-3-acetic acid and N-[trans-7-methoxy-5-(naphthalen-1-yl)-1-neopentyl-1,2,3,5-tetrahydro-2-oxo-4,1-benzothiazepine-3-acetyl]isonipecotic acid.

Other compounds within the immediately preceding first group of particularly preferred compounds, which is within the fourth group of especially preferred compounds, are compounds wherein T forms a piperidin-1-yl ring and a. $R_4$ is neopentyl;

$R_1$ is 7-chloro;

$R_2$ is H; and

Z is 3-carboxylpiperidin-1-yl-carbonyl;

b. $R_4$ is neopentyl;

$R_1$ is 7-chloro;

$R_2$ is H; and

Z is 4-ethoxycarbonylpiperidin-1-yl-carbonyl; or c. $R_4$ is neopentyl;

$R_1$ is 7-chloro;

$R_2$ is H; and

Z is 4-carboxylpiperidin-1-yl-carbonyl; and preferred stereoisomers thereof are (−)-N-(trans-7-chloro-5-(1-naphthyl)-1-neopentyl-2-oxo-1,2,3,5-tetrahydro-4,1-benzothiazepin-3-acetyl)-nipecotic acid, Ethyl ester of (−)-N-(trans-7-chloro-5-naphthyl-1-neopentyl-2-oxo-1,2,3,5-tetrahydro-4,1-benzothiazepin-3-acetyl)isonipecotic acid, or (−)-N-(trans-7-chloro-5-(1-naphthyl)-1-neopentyl-2-oxo-1,2,3,5-tetrahydro-4,1-benzothiazepin-3-acetyl)-isonipecotic acid.

Within the fourth group of especially preferred compounds is another compound wherein $R_4$ is neopentyl;

$R_1$ is 7-chloro;

$R_2$ is H; and

Z is carboxyl, and a stereoisomer thereof (−)-trans-7-chloro-5-(1-naphthyl)-1-neopentyl-2-oxo-1,2,3,5-tetrahydro-4,1-benzothiazepin-3-acetic acid, and (R)-α-methylbenzylammonium salt thereof.

Within the fourth group of especially preferred compounds are compounds wherein a. $R_4$ is neopentyl;

$R_1$ is 7-chloro;

$R_2$ is H;

V is —$CO_2R_7$;

Z is

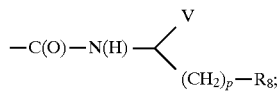

$R_7$ is methyl;
$R_8$ is carboxyl; and
p is 2;
b. $R_4$ is neopentyl;
$R_1$ is 7-chloro;
$R_2$ is H;
V is —$CO_2R_7$;
Z is

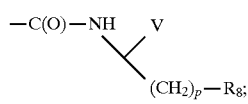

$R_7$ is methyl;
$R_8$ is carboxyl; and
p is 1; and
c. $R_4$ is neopentyl;
$R_1$ is 7-chloro;
$R_2$ is H;
V is —$CO_2R_7$;
Z is

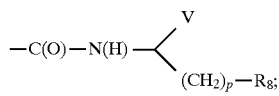

$R_7$ is H;
$R_8$ is thiomethyl; and
p is 1.

Within the immediately preceding group are the stereoisomers
(–)-N-(trans-7-chloro-5-(1-naphthyl)-1-neopentyl-2-oxo-1,2,3,5-tetrahydro-4,1-benzothiazepin-3-acetyl)-L-glutamic acid-α-methyl ester,
(–)-N-(trans-7-chloro-5-(1-naphthyl)-1-neopentyl-2-oxo-1,2,3,5-tetrahydro-4,1-benzothiazepin-3-acetyl)-L-aspartic acid-α-methyl ester or
(–)-N-(trans-7-chloro-5-(1-naphthyl)-1-neopentyl-2-oxo-1,2,3,5-tetrahydro-4,1-benzothiazepin-3-acetyl)-L-S-methylcysteine.

Within the fourth group of especially preferred compounds are compounds wherein
T forms a pyrrolidin-1-yl ring.

Within the immediately preceding group of compounds is a compound wherein
$R_4$ is neopentyl;
$R_1$ is 7-chloro;
$R_2$ is H; and
Z is L-proline-N-carbonyl or D-proline-N carbonyl and the stereoisomers thereof
(–)-N-(trans-7-chloro-5-(1-naphthyl)-1-neopentyl-2-oxo-1,2,3,5-tetrahydro-4,1-benzothiazepin-3-acetyl)-L-proline and
(–)-N-[trans-7-chloro-5-(1-naphthyl)-1-neopentyl-2-oxo-1,2,3,5-tetrahydro-4,1-benzothiazepin-3-acetyl]-D-proline.

Within the first group of preferred compounds is a fifth group of especially preferred compounds wherein
the $C^3$ and $C^5$ substituents are trans;
$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$alkoxy having from 1 to 9 fluorines, $(C_1-C_4)$alkanoyl or $R_1$ and $R_2$ taken together form an ethylenedioxy ring;
$R_3$ is H;
$R_9$ is $(C_1-C_4)$alkoxy
X is oxy;
Y is carbonyl;
V is —$CO_2R_7$; and
Z is carboxyl, tetrazol-5-yl,

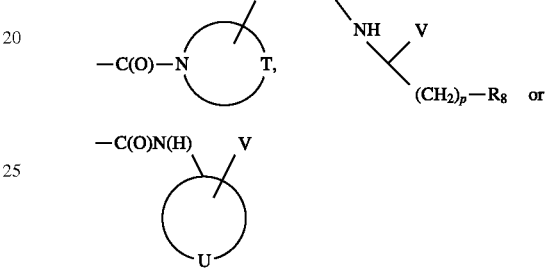

Within the fifth group of especially preferred compounds are compounds wherein
$R_1$ is 7-chloro;
$R_2$ is H;
$R_4$ is neopentyl;
$R_9$ is methoxy; and
T forms a piperidin-1-yl ring.

Within the immediately preceding group are the compounds
trans-7-chloro-5-(4-methoxynaphthalen-1-yl)-1-neopentyl-1,2,3,5-tetrahydro-2-oxo-4,1-benzoxazepine-3-acetic acid;
N-[trans-7-chloro-5-(4-methoxynaphthalen-1-yl)-1-neopentyl-1,2,3,5-tetrahydro-2-oxo-4,1-benzoxazepine-3-acetyl]isonipecotic acid; or
N-[trans-7-chloro-5-(4-methoxynaphthalen-1-yl)-1-neopentyl-1,2,3,5-tetrahydro-2-oxo-4,1-benzoxazepine-3-acetyl]nipecotic acid.

Yet another aspect of this invention is directed to a method for treating hypercholesterolemia, atherosclerosis, fungal infections, Alzheimer's or acne in a mammal by administering to a mammal suffering from hypercholesterolemia, atherosclerosis, a fungal infection, Alzheimer's or acne a hypercholesterolemia, atherosclerosis, antifungal, Alzheimer's or acne treating amount of a Formula I compound.

This invention is also directed to pharmaceutical compositions for the treatment of hypercholesterolemia, atherosclerosis, fungal infections, Alzheimer's or acne in mammals which comprise a therapeutically effective amount of a compound of the Formula I and a pharmaceutically acceptable carrier.

Exemplary T rings are piperidin-1-yl, pyrrolidin-1-yl, thiazolidin-3-yl, azetidin-1-yl, tetrahydro-1,4-thiazin-4-yl, tetrahydro-1,4-oxazin-4-yl and tetrahydro-1,3-thiazin-3-yl.

Exemplary U rings are cyclopropyl, cyclobutyl, cyclopentyl and cyclohexyl.

By halo is meant chloro, bromo, iodo, or fluoro.

By alkyl is meant straight chain or branched saturated hydrocarbon.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, L-lysine, L-arginine, meglamine (N-methyl-glucamine), benethamine (N-benzylphenethylamine), piperazine or tromethamine (2-amino-2-hydroxymethyl-1,3-propanediol). This is meant to include (R)-α-methylbenzylammonium.

The expression "prodrug" refers to compounds that are drug precursors, which following administration and absorption, release the drug in vivo via some metabolic process. Exemplary prodrugs upon cleavage release the corresponding free acid, and such hydrolyzable ester-forming residues of the Formula I compounds include but are not limited to substituents wherein the Z or the V moiety is carboxyl and the free hydrogen is replaced by ($C_1$–$C_4$) alkyl, ($C_2$–$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

As used herein, the expression "reaction-inert solvent" refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

Other features and advantages will be apparent from the specification and claims which describe the invention.

DETAILED DESCRIPTION OF THE INVENTION

REACTION SCHEME I

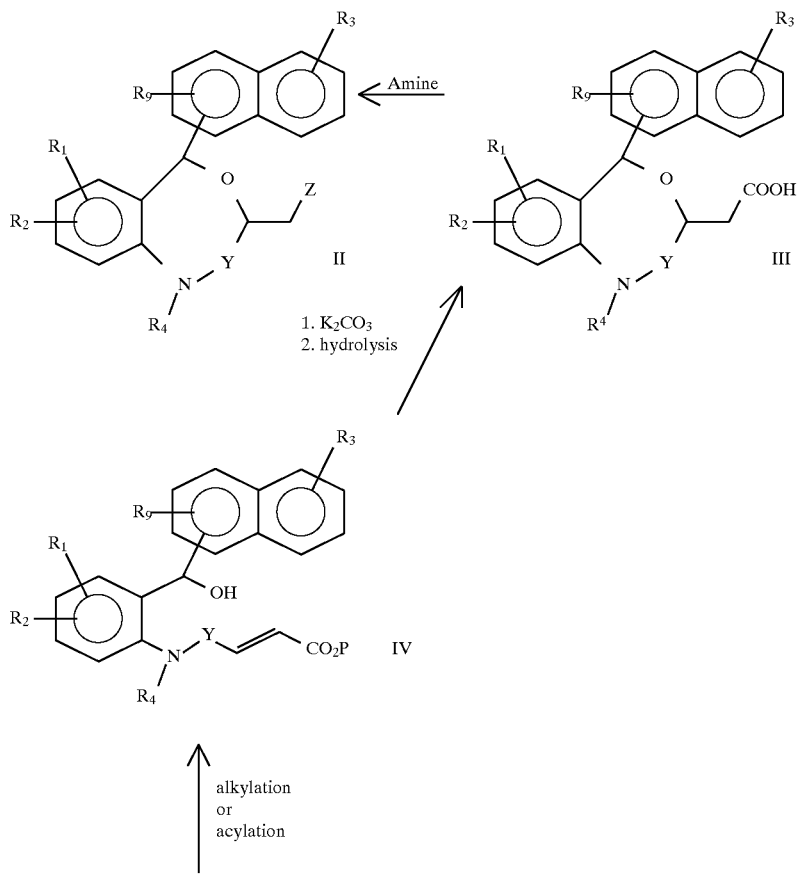

-continued
REACTION SCHEME I
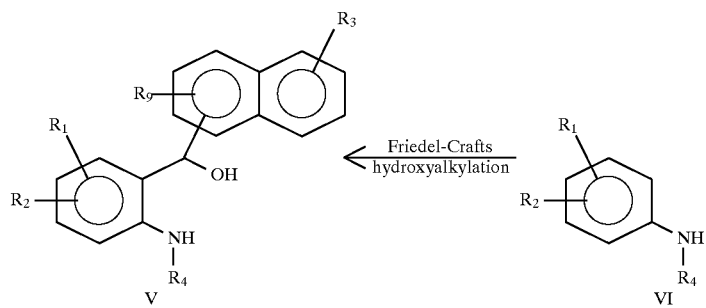
REACTION SCHEME II
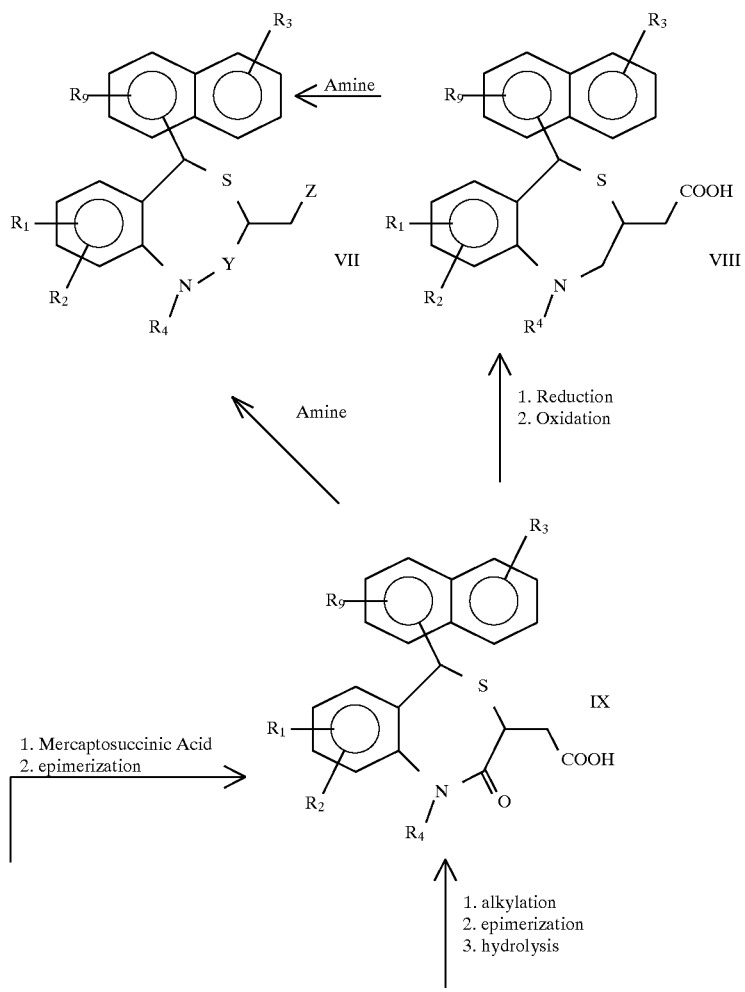

-continued
REACTION SCHEME II

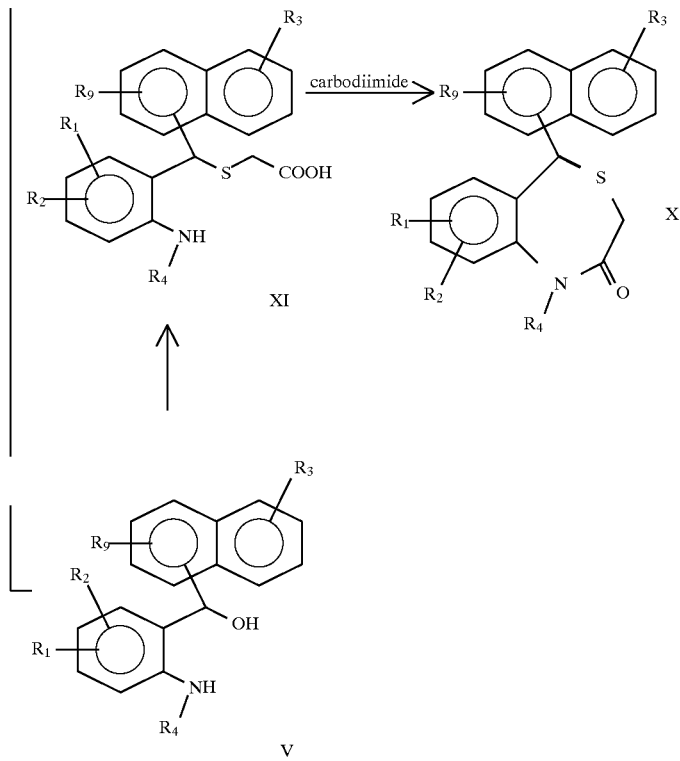

According to Reaction Scheme I the desired Formula I compounds wherein $R_1$, $R_2$, $R_3$, $R_4$ and $R_9$ are as described above, X is oxy, Y is carbonyl or methylene and Z is a substituted amide (depicted as Formula II compounds) may be prepared by acylating the appropriate amine with the corresponding Formula III compound wherein Z is carboxyl.

Generally, the acid is combined with the appropriate amine In an aprotic solvent such as dimethylformamide in the presence of an amine base such as triethylamine and a coupling agent such as diethyl cyanophosphonate or propylphosphonic anhydride at a temperature of about 0° C. to about 40° C. for about 1 hour to about 6 hours.

Alternatively, the acid is combined with the appropriate amine in the presence of a carbodiimide (e.g., 1-(3-dimethylaminopropyl)-3-ethylcarbodiimide hydrochloride) in a reaction inert solvent such as methylene chloride at a temperature of about 10° C. to 40° C. for about 2 to about 24 hours.

The desired Formula I compound wherein Z or V is tetrazol-5-yl may be prepared from the corresponding Formula I compound wherein Z or V is carboxyl by converting the carboxyl group to a carboxamide group (Z or V=$CONH_2$), dehydrating the carboxamide to the nitrile (Z or V=CN) and reacting the nitrile with an appropriate azide to form the tetrazole group.

Generally, the acid is converted to the imidazolide by reaction with carbonyl diimidazole in an aprotic solvent such as methylene chloride at a temperature of 15° C. to about 40° C. for about 30 minutes to about 4 hours, conveniently at room temperature for 1 hour. The resulting imidazolide is converted to the corresponding amide by bubbling ammonia gas into the reaction mixture at a temperature of 10° C. to about 40° C. for about 3 minutes to about 30 minutes, preferably at room temperature for about 5 minutes or until the reaction is complete by TLC analysis. The amide is converted to the nitrile by treatment with trifluoroacetic anhydride and triethylamine in an inert solvent such as methylene chloride at 0° C. for about 25 minutes to 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole.

The desired Formula I compound wherein Z or V is 4,5-dihydro-5-oxo-1,2,4-oxadiazol-3-yl may be prepared from the corresponding Formula I compound wherein Z or V is CN by converting the nitrile to the amide oxime and reacting the amide oxime with a carbonylating agent to form the corresponding 4,5-dihydro-5-oxo-1,2,4-oxadiazole derivative.

Generally, the nitrile is converted to the amide oxime by reaction with hydroxylamine hydrochloride in the presence of a base such as potassium carbonate in an alcoholic solvent at a temperature of about 60° C. to about 110° C. for about 5 hours to 24 hours, preferably in refluxing ethanol for about 18 hours. The amide oxime is converted to the corresponding 4,5-dihydro-5-oxo-1,2,4-oxadiazole derivative by reaction with carbonyidiimidazole and triethylamine in refluxing ethyl acetate for 24 hours.

Prodrugs of Formula I compounds having a carboxyl group may be prepared by combining the acid with the appropriate alkyl halide in the presence of a base such as potassium carbonate in an inert solvent such as dimethylformamide at a temperature of about 15° C. to about 100° C. for about 1 hour to about 24 hours.

Alternatively, the acid is combined with the appropriate alcohol as solvent in the presence of a catalytic amount of acid such as concentrated sulfuric acid at a temperature of about 20° C. to about 120° C., preferably at reflux, for about 1 hour to about 24 hours.

The desired Formula III compounds wherein $R_1$, $R_2$, $R_3$, $R_4$ and $R_9$ are as described above, X is oxy, Y is carbonyl or methylene and Z is carboxyl may be prepared from the corresponding Formula IV compound by cyclization followed by hydrolysis. Alternatively, the hydrolysis step may be omitted resulting in the desired prodrugs.

Generally, the Formula IV compound is combined with a base such as potassium carbonate in an alcoholic solvent such as ethanol at a temperature of about 10° C. to about 40° C., preferably ambient, for about 2 hours to about 18 hours followed by hydrolysis in an aqueous alcoholic solvent such as methanol/water with a base such as potassium carbonate at a temperature of about 40° C. to about 80° C., preferably at reflux, for about 2 hours to about 18 hours.

The desired Formula IV compounds wherein $R_1$, $R_2$, $R_3$, $R_4$ and $R_9$ are as described above, X is oxy, Y is carbonyl or methylene and P is a known carboxyl protecting group (see reference below) may be prepared from the appropriate corresponding Formula V compound by acylation or alkylation as appropriate.

Generally, for those compounds wherein Y is carbonyl the appropriate Formula V compound is combined with the appropriate fumaryl chloride protected mono acid, such as fumaryl chloride monoalkyl ester, in a reaction-inert solvent such as methylene chloride at a temperature of about 10° C. to about 50° C., typically ambient, for about six to about eighteen hours. Generally, for those compounds wherein Y is methylene the appropriate Formula V compound is combined with the appropriate protected 4-halocrotonic acid, such as alkyl 4-halocrotonate, in the presence of a base such as potassium carbonate in an aprotic solvent such as dimethylformamide at a temperature of about 10° C. to about 50° C., typically ambient, for about 12 hours to about 72 hours.

The desired Formula V compound wherein $R_1$, $R_2$, $R_3$, $R_4$ and $R_9$ are as described above may be prepared from the appropriate corresponding Formula VI compound by hydroxyalkylation (a modified Friedel-Crafts reaction).

Generally, the Formula VI compound is combined with a Lewis acid such as boron trichloride in a reaction-inert solvent such as benzene or toluene at a temperature of about ambient to about reflux for about 1 to about 6 hours under a nitrogen atmosphere to form an intermediate complex. The resulting complex is combined with the appropriately substituted naphthaldehyde in a reaction-inert solvent such as benzene in the presence of an amine base such as triethylamine at a temperature of about 0° C. to about 40° C., typically ambient, for about 30 minutes to about 18 hours followed by acid cleavage of the boron moiety.

Alternatively, a Formula V compound, wherein $R_1$ is 4-trifluoromethyl and $R_4$ is neopentyl, may be prepared by treating a Formula VI compound, wherein $R_1$ is 4-trifluoromethyl and $R_4$ is pivaloyl, with excess strong base, preferably 2.5 equivalents of n-butyllithium, in an anhydrous ethereal solvent, preferably tetrahydrofuran, at a temperature of about ambient to about 50° C. for about 1 hour to about 3 hours and reacting the resulting dianion with the appropriate naphthaldehyde. The resulting 2-(alpha-hydroxymethyinaphthalene) Formula V compound, wherein $R_4$ is pivaloyl, is converted to the Formula V compound, wherein $R_1$ is 4-trifluoromethyl and $R_4$ is neopentyl, by reducing the pivalamide functionality with a reducing agent such as lithium aluminum hydride or borane, preferably a borane-tetrahydrofuran complex, in an ethereal solvent such as tetrahydrofuran at an elevated temperature, typically reflux. Alternatively, the Formula V compounds wherein $R_1$ is 4-trifluoromethyl and $R_4$ is alkyl, including neopentyl, may be prepared by treating the Formula VI compound, wherein $R_1$ is 4-trifluoromethyl and $R_4$ is t-butoxycarbonyl, with an excess of t-butyllithium, preferably 2.4 equivalents, at a temperature of about −50° C. to about 0° C. in an ethereal solvent such as anhydrous tetrahydrofuran for about 2 hours to about 4 hours and coupling the resulting dianion with the appropriate naphthaldehyde. The resulting 2-(alpha-hydroxymethylnaphthalene) Formula V compound, wherein $R_1$ is 4trifluoromethyl and $R_4$ is t-butoxycarbonyl, is treated with acid and thereby converted to the Formula V compound, wherein $R_1$ is 4-trifluoromethyl and $R_4$ is H. This compound is transformed to the Formula V compound, wherein $R_1$ is 4-trifluoromethyl and $R_4$ is alkyl, by reductive amination under conditions similar to that for the preparation of the Formula VI compounds.

The desired Formula VI compound wherein $R_1$, $R_2$ and $R_4$ are as described above may be prepared from the appropriate corresponding aniline by reductive amination.

Generally, the aniline is reacted with the appropriate alkylaldehyde in a protic acidic solvent such as concentrated acetic acid at a temperature of about 10° C. to about 50° C., preferably ambient, for about 30 minutes to about four hours followed by reduction using for example sodium borohydride at a temperature of about 0° C. to about 20° C. for about 15 minutes to about four hours.

Alternatively, the aniline is reacted with the appropriate alkylaldehyde in an aprotic solvent such as 1,2-dichloroethane in the presence of an acid such as acetic acid at a temperature of about 15° C. to about 40° C., preferably ambient temperature, for a period of about 1 to about 20 hours followed by reduction using for example sodium triacetoxyborohydride at about −20° C. to about ambient temperature for a period of about 1 to about 20 hours.

According to Reaction Scheme II the desired Formula VII compounds wherein $R_1$, $R_2$, $R_3$, $R_4$ and $R_9$ are as described above, X is thio, Y is carbonyl or methylene and Z is a substituted amide may be prepared by acylating the appropriate amine with the corresponding Formula VIII or IX compound wherein Z is carboxyl. Generally this reaction may be performed as describe above for the Formula II compounds.

The desired Formula VIII compounds wherein $R_1$, $R_2$, $R_3$, $R_4$ and $R_9$ are as described above, X is thio, Y is methylene may be prepared from the appropriate corresponding Formula IX compound where Y is carbonyl by a sequential reduction/oxidation procedure.

Generally the Formula IX compound is fully reduced using for example a borane-methyl sulfide complex in a reaction-inert solvent such as tetrahydrofuran at a temperature of about 20° C. to about 80° C., preferably at reflux, for about 1 hour to about 6 hours. The resulting alcohol is then oxidized to the Formula VIII compound using for example a two step procedure involving first a Swern oxidation followed by oxidation with buffered sodium chlorite in acetonitrile and aqueous hydrogen peroxide at a temperature of about −10° C. to about 25° C. for about 30 minutes to about 4 hours. Or alternatively, the alcohol is directly oxidized to the acid using t-butyl hydroperoxide and cetyl trimethyl ammonium sulfate in an aqueous mixture at pH>13.

The desired Formula IX compound wherein $R_1$, $R_2$, $R_3$, $R_4$ and $R_9$ are as described above, may be prepared from the appropriate corresponding Formula X compound by alkylation followed by epimerization and finally hydrolysis.

Generally, the Formula X compound is combined with a base such as lithium diisopropylamide in a reaction-inert solvent such as cyclohexane/tetrahydrofuran at a temperature of about −100° C. to about −20° C. under nitrogen for about 30 minutes to about 3 hours followed by addition of a suitable alkyl haloacetate such as t-butyl bromoacetate and mixing for about 2 to about 24 hours at a temperature of about 10° C. to about 40° C., preferably ambient. The alkylated product is epimerized to exclusively the trans isomers using a base like potassium carbonate in an alcoholic solvent like methanol for 1 hour to 6 hours at a temperature of about 40° C. to about 80° C., preferably at 60° C. The resulting t-butyl ester may be hydrolyzed by treatment with an acid such as trifluoroacetic acid in a reaction-inert solvent such as dichloromethane.

The desired Formula X compound wherein $R_1$, $R_2$, $R_3$, $R_4$ and $R_9$ are as described above, may be prepared from the appropriate corresponding Formula XI compound by coupling under carbodiimide conditions.

Generally, the Formula XI compound is combined with a suitable carbodiimide such as 1-(3-dimethylaminopropyl)-3-ethylcarbodiimide hydrochloride in a reaction-inert solvent such as dichloromethane at a temperature of about 10° C. to about 50° C., conveniently at ambient temperature, for about 5 hours to about 24 hours.

The desired Formula XI compound wherein $R_1$, $R_2$, $R_3$, $R_4$ and $R_9$ are as described above, may be prepared from the appropriate corresponding Formula V compound by a solvolytic displacement reaction.

Generally, the Formula V compound may be combined with mercaptoacetic acid under aqueous acidic conditions at a temperature of about 60° C. to about 120° C., conveniently at reflux, for about 2 to about 6 hours.

Alternatively, the desired Formula IX compounds wherein $R_1$, $R_2$, $R_3$, $R_4$, and $R_9$ are as described above may be prepared from the appropriate corresponding Formula V compound by a solvolytic displacement reaction with cyclization to the lactam followed by epimerization.

Generally, the Formula V compound and mercaptosuccinic acid are combined in a carboxylic acid solvent such as propionic acid and heated to about 100° C. to about 140° C. for about 12 to 72 hours with a means to remove water such as a nitrogen sweep across the head space of the reaction vessel. The cyclized product is epimerized to the trans isomers by treatment in an inert solvent such as tetrahydrofuran with a base such as a metal alkoxide base in the corresponding alcohol solvent, preferably sodium methoxide in methanol, at about ambient temperature to reflux temperature for a period of about 1 to about 24 hours.

The starting materials and reagents for the above described reaction schemes (e.g., 4-haloaniline, 1-naphthaldehyde, fumaric acid monoethyl ester, amino acid esters, prodrug residues, protected forms) are readily available or can be easily synthesized by those skilled in the art using conventional methods of organic synthesis. Some of the preparation methods described herein will require protection of remote functionality (i.e., carboxyl). The need for these protecting groups will vary depending on the nature of the remote functionality and the conditions of the preparation methods. This need is readily determined by one skilled in the art. For a general description of protecting groups (e.g., halo($C_1$–$C_4$)alkyl, ($C_1$–$C_4$)alkoxymethyl, arylmethyl and tri($C_1$–$C_4$)alkylsilyl) and their use, see T. W. Greene, *Protective Groups in Organic Synthesis*, John Wiley & Sons, New York, 1991.

The compounds of Formula I have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers (e.g., of Formula III, VII or IX) can be separated by converting the enantiomeric mixture into a diasteromeric mixture (e.g., ester or salt) by reaction with an appropriate optically active compound (e.g., alcohol or amine), separating the diastereomers and converting (e.g., hydrolyzing or acidifying) the individual diastereomers to the corresponding pure enantiomers. All such isomers, including diastereomers and enantiomers are considered as part of this invention.

Some of the compounds of this invention, where for example Z contains an acid group, are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some of the compounds of this invention where, for example Y is methylene or Z contains an amine group are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The compounds of this invention are all adapted to therapeutic use as agents that lower plasma LDL cholesterol levels in mammals, particularly humans. Since the concentration of cholesterol in blood is closely related to the development of cardiovascular, cerebral vascular or peripheral vascular disorders, these compounds, by virtue of their hypocholesterolemic action, prevent, arrest and/or regress atherosclerosis.

The hypocholesterolemia activity of these compounds can be determined by assessing the effect of these compounds on the action of squalene synthetase by measuring the overall conversion of [1-$^3$H]farnesyl pyrophosphate to [$^3$H] squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic acid A).

Briefly, to a 3 μl volume of either DMSO (control) or DMSO containing compound, are added 47 μl of Squalene Synthetase Cofactor/Substrate solution (SQS Cofactor/Substrate solution contains 50 mM $K_xPO_4$ (pH=7.4), 5.0 mM $MgCl_2$, 411 μM $NADP^+$, 3.4 mM glucose-6-phosphate, 20 U/ml glucose-6-phosphate dehydrogenase, 15 mM NaF, 78.1 mM sodium ascorbate, 31.3 U/ml ascorbate oxidase, and 1.56 times the indicated final concentrations of {$^3$H]FPP (sp. act. 380/pmol)) and 25 μl of PMED buffer (PMEB buffer contains 50 mM K$_x$PO$_4$ (pH 7.4), 5 mM MgCl$_2$, 1.0 mM EDTA, 5.0 mM dithiothreitol) containing 1 mg/ml microsomal protein [Final assay concentrations: 48 mM K$_x$PO$_4$ (pH 7.4), 4.8 mM MgCl$_2$, 0.33 mM EDTA, 1.67 mM DTT, 258 μM NADP$^+$, 2.1 mM glucose-6-phosphate, 0.95U glucose-6-phosphate dehydrogenase, 9.5 mM NaF, 50 mM sodium ascorbate, 1.5U ascorbate oxidase, 4% DMSO, and 5.1 μM [$^3$H]farnesyl pyrophosphate]. After incubation at 37° C. for 30 min, enzymatic reactions are terminated by sequential addition of 40 μl 10M NaOH, 40 μl EtOH, 10 μl of 2 mg/ml squalene in chloroform. After saponification (90 minutes, 37° C.), aliquots were applied to silica gel TLC and newly formed squalene separated from unreacted substrate by chromatography in toluene-ethyl acetate (9:1). The squalene band is visualized with iodine vapors, removed, and immersed in Aqualsol-2 liquid scintillation fluid. Squalene synthetase activity is expressed as pmoles of squalene formed from farnesyl pyrophosphate per min of incubation at 37° C. per mg microsomal protein, based on the stoichiometry of the reaction whereby two moles of [$^3$H]farnesyl pyrophosphate react to form one mole of [$^3$H]squalene and half of the radiolabel is lost from the C-1 position of the prenylating [$^3$H]farnesyl pyrophosphate due to 1-pro-S hydrogen release. Rat hepatic microsomes are used as the source of squalene synthetase activity as described by Harwood et al (J. Lipid Res. 34, 377, 1993). Briefly, hepatic tissues are rinsed in phosphate buffered saline and immediately homogenized at 4° C. in PMED buffer, using a Dounce tissue homogenizer. Homogenates are centrifuged at 10,000×g for 20 min at 4° C. and the resultant supernatants are centrifuged at 178,000×g for 90 min at 4° C. Microsomal pellets were resuspended in PMED buffer by a Potter-Elvehjem pestle and stored frozen in liquid N$_2$ until use. For such preparations, there is no notable loss in enzyme activity within 3 months.

The hypercholesterolemic treating activity of these compounds may be demonstrated by methods based on standard procedures. For example, the in vivo activity of these compounds in inhibiting cholesterol biosynthesis may be determined by the procedure of Hughes et. al. 1977 J. Biol Chem. 252: 548.

Activity of these compounds can be determined by the amount of hypocholesterolemic agent that reduces hepatic cholesterol biosynthesis, relative to control, in male CD1 mice. Male CD1 mice are maintained on a cholesterol-free diet in a 12 hr light/12 hr dark cycle. At mid light cycle animals are administered a 0.5 mL oral bolus of saline containing 0.25% methyl cellulose, 0.6% Tween 80 and 10% ethanol (control animals) or an oral bolus that contained in addition the desired concentration of compound to be tested. One hour following bolus administration the animals receive an intraperitoneal injection (0.15 ml) of [$^{14}$C]-mevalonolactone dissolved in water (0.5 uCi/animal). One hour following the injection of radioactivity animals are sacrificed, livers excised, saponified (saponified (2.5 M KOH, 2h) 60° C.) and extracted with petroleum ether and ethanol. After saponification, the radioactivity is measured. Total hepatic radioactivity is calculated based on measured liver weights. The degree of cholesterol biosynthesis inhibition is expressed as a percentage of the total radioactivity in treated vs control animals. The above assay carried out with a range of doses of test compounds allow the determination of an approximate ED$_{50}$ value for the in vivo reduction of hepatic cholesterol biosynthesis.

The hypercholesterolemic treating activity of these compounds may also be demonstrated by determining the amount of agent required to reduce cholesterol levels, for example LDL cholesterol levels, in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). Adult marmosets are assigned to treatment groups so that each group has a similar mean ±SD for total plasma cholesterol concentration. After group assignment, marmosets are dosed daily with compound as a dietary admix or by intragastric intubation for from one to eight weeks. Control marmosets receive only the dosing vehicle. Plasma total, LDL and HDL cholesterol values can be determined at any point during the study by obtaining blood from an antecubital vein and by separating plasma lipoproteins into their individual subclasses by density gradient centrifugation, and by measuring cholesterol concentration as previously described (Crook, et al., Arteriosclerosis 10, 625, 1990).

Anti-atherosclerosis effects of the compounds can be determined by the amount of agent required to reduce the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean ±s.d. for total plasma cholesterol concentration. After group assignment, rabbits are dosed daily with compound given as a dietary admix or on a small piece of gelatin based confection. Control rabbits receive only the dosing vehicle be it the food or the gelatin confection. The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the iliac arteries. The aortae are cleaned of adventitia, opened longitudinally and then stained with Sudan IV as described by Holman et al. (Lab. Invest. 1958, 7, 4247). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention can be via any method which delivers the squalene synthetase inhibitor to the intestine and the liver. These methods include oral routes, parenteral, intraduodenal routes etc.

Thus, for example, in one mode of administration a squalene synthetase inhibitor of this invention may be administered once at night prior to sleep. Alternatively the compounds may be administered twice or three times daily with or without meals. In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the plasma cholesterol lowering that he/she considers appropriate for the patient. In considering the degree of hypocholesterolemic activity desired, the physician must balance a variety of factors such as starting cholesterol level, other cardiovascular risk factors, presence of preexisting disease, and age of the patient and his/her motivation. Those skilled in the art will know of the National Cholesterol Education program guidelines for treatment of hypercholesterolemia (Circulation 1991; 83:2154) In general an effective dosage for the squalene synthetase inhibitors described above is in the range of 0.0005 to 50 mg/kg/day, preferably 0.001 to 25 mg/kg/day, most preferably 0.005 to 5 mg/kg/day. For an average 70 kg human, this would amount to 0.000035 to 3.5 g/day, preferably 0.00007 to 1.75 g/day, most preferably 0.00035 to 0.35 g/day.

The present invention compounds also demonstrate broad spectrum antifungal activity as determined by broth or agar dilution methods.

In case of administering the compound of the present invention for the therapy of fungus infections, generally from 0.0005 to 100 mg/kg/day should be employed as a unit dosage in an antifungal treatment.

The antifungal activity of the compound of this invention may be determined with a bioassay that utilizes *Crypococcus bhutenensis* FD 23971. A ten-day-old slant of *C. bhutenensis* is washed with 10 mL of sterile water, and 300 $\mu$l of the suspension is mixed with an assay medium consisting of 0.67% of yeast nitrogen based medium (DIFCO) and 0.5% of glucose. 150 mL of the warm medium is poured onto a sterile, polystyrene bioassay plate (245×245×20 mm) and is left to solidify. The solid medium is bored into well-separated wells with a size #2 cork bore, and a suitable solution of the compound to be tested is spotted into the wells. The plates are incubated at 28° C. for 2 to 3 days and the zone of inhibition is measured according to standard procedures against controls.

As an antifungal treatment the compounds of this invention are administered to mammals (e.g., humans) by conventional methods.

Since the compounds of this invention are cholesterol biosynthesis inhibitors they can also lower the levels of Apolipoprotein E isoform 4 circulating in the bloodstream Apolipoprotein E isoform 4 that is made in the brain also circulates through the central nervous system and is present in the cerebrospinal fluid. Compounds of this invention are useful for the treatment of Alzheimer's disease.

Apolipoprotein E isoform 4 ("ApoE isoform 4") is an apolipoprotein which is the gene product of the apolipoprotein E Type 4 allele and is carried in the bloodstream on lipoproteins including LDL. Possession of one or two copies of the apolipoprotein E type 4 allele has been linked to a greatly increased risk of developing Alzheimers disease. In the liver, low density lipoprotein receptors (LDL receptors) are responsible for absorbing and taking up from the bloodstream various lipoproteins including some of those containing ApoE isoform 4. LDL receptors are regulated by gene repressors derived from cholesterol that suppress the transcription of the LDL-receptor. Inhibition of cholesterol biosynthesis reduces the presence of these cholesterol-derived LDL gene repressors. This relieves the suppression of the production of the LDL receptor, leading to production of additional LDL receptors in the liver, which in turn, remove additional amounts of lipoproteins including ApoE Type 4 containing lipoproteins from the bloodstream.

The Alzheimer's disease treating activity of these compounds can be determined by assessing the effect of these compounds on the action of squalene synthetase by measuring the overall conversion of [1-$^3$H]famesyl pyrophosphate to [$^3$H]squalene, essentially as previously described in Meth. Enzymol. 110, 359, 1985 using the anaerobic atmosphere generating oxygen consumption system described in Analyt. Biochem. 203, 310, 1992, in comparison to known controls (e.g., zaragozic acid A). This assay is described more fully above.

The Alzheimer's disease treating activity of these compounds may also be demonstrated by determining the amount of agent required to reduce cholesterol levels, for example LDL cholesterol levels, in the plasma of certain mammals, for example marmosets that possess a plasma lipoprotein profile similar to that of humans (Crook et al. Arteriosclerosis 10, 625, 1990). Cholesterol synthesis inhibitors, for example HMG-CoA reductase inhibitors and the squalene synthetase inhibitor zaragozic acid A, lower plasma cholesterol concentrations in this species (Baxter, et al., J. Biol. Chem. 267, 11705, 1992). This assay is described more fully above.

The compounds of this invention may be administered in conventional methods for the treatment of Alzheimer's disease. In general an effective dosage for the squalene synthetase inhibitors of this invention for the treatment of Alzheimer's disease is in the range for adults of from about 1 mg to 1000 mg (preferably 5 to 100 mg,) which may be given in a single dose or in two to four divided doses. Higher doses may be favorably employed as required.

Since the compounds of this invention are squalene synthesis inhibitors they are effective for the treatment of acne vulgaris. Squalene is a major component of sebum, comprising about 12% of sebum in adults. The severity of acne vulgaris correlates directly with the sebum secretion rate and several compounds which decrease sebum secretion rate have been shown to improve acne. By inhibiting squalene the compounds of this invention can decrease the sebum secretion rate and thereby improve acne.

The concentration of squalene in sebum increases four-fold after puberty and It is believed that this increase in squalene concentration alone or in concert with other changes in sebum composition or sebum secretion rate facilitate the development of acne. The compounds of this invention are useful in preventing or mollifying acne by reducing the percentage and total amount of squalene in sebum.

In addition to reducing squalene levels in sebum, by limiting the production of epoxides, the sebum may become less inflammatory (through metabolic action of the ever-present P. acnes). The compounds of this invenetion may therefor provide a dual effect to combat acne and thus constitute a new, better treatment for acne than current keratolytic and anti-androgen therapies.

The anti-acne activity of the compounds of this invention may be demonstrated by testing the in vitro effects of the compounds in human sebaceous gland culture using conditions similar to those described in FEBS Letters 200(1), 173–176 (1986) and J. Cell Science 95, 125–136 (1990). Thus, the human sebaceous gland culture may be incubated with the test compound and subsequent sebum production and qualitative changes of sebum composition measured over a short period of time and compared with controls and other actives.

For the treatment of acne the compounds of this invention may be administered by conventional methods. For the treatment of acne each dosage unit will preferably contain 0.001 mg to 1000 mg, advantageously 0.01 mg to 400 mg, of active ingredient. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient.

The compounds of this invention may also be used in conjunction with other pharmaceutical agaents. For example, they may be used in combination with fibrates, niacins, ion-exchange resins, antioxidants, ACAT inhibitors and bile acid sequestrants as a measns of lowering plasma cholesterol and as a means of treating atherosclerosis. Alternatively, they may be used in conjunction with another anti-acne agent (e.g. a topical antibiotic). In combination therapy treatment, both the squalene synthetase inhibitors of this invention and the other drug therapies are administered to mammals (e.g., humans) by conventional methods.

The compounds can be administered individually or together in any conventional oral or parenteral dosage form such as a capsule, tablet, powder, cachet, suspension or solution. For oral administration, which is preferred, a pharmaceutical composition can take the form of solutions, suspensions, tablets, pills, capsules, powders, and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound(s) according to the invention as an active ingredient. In addition, it may include other medicinal or pharmaceutical agents, carriers, adjuvants, etc.

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the signs of the subject being treated, i.e., hypercholesterolemia, atherosclerosis, Alzheimer's disease or fungal infection.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing a compound(s) according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent in light of this disclosure, to those skilled in this art. For examples, see Remington's Pharmaceutical Sciences., Mack Publishing Company, Easter, Pa., 15th Edition (1975).

EXAMPLE 1

Ethyl ester of trans-7-chloro-5-(naphthalen-1-yl)-1-neopentyl-1,2,3,5-tetrahydro-2-oxo-4,1-benzoxazepine-3-acetic acid

EXAMPLE 1A (4-Chloro-phenyl)-(neopentyl)-amine

Pivalaldehyde (20.4 g, 236 mmol, 25.6 mL) was added to a solution of 4-chloroaniline (30.2 g, 236 mmol) in concentrated acetic acid (475 mL) at ambient temperature. After 1.5 hour, the reaction mixture was cooled to 0° C. and sodium borohydride (11.7 g, 307 mmol) was added portionwise over 15 minutes After stirring for 1 hour, the resulting mixture was diluted with water and extracted with ethyl acetate (3×). The combined organics were washed successively with water (3×), aqueous 2N sodium hydroxide (2×), saturated aqueous sodium bicarbonate, and saturated aqueous sodium chloride, dried over anhydrous sodium sulfate, filtered, and concentrated under reduced pressure to give 47.2 g (99%) of the title compound as an off-white solid which was taken on crude to the next step.

$^1$H NMR (250 MHz, CDCl$_3$) δ 7.10 (d, 2H), 6.53 (d, 2H), 3.65 (br s, 1 H), 2.85 (s, 2H), 0.98 (s, 9H).

EXAMPLE 1B (5-Chloro-2-neopentylamino-phenyl)-naphthalen-1-yl-methanol

A solution of (4-chloro-phenyl)-(neopentyl)-amine (6.58 g, 33.3 mmol) in benzene (15 mL) was added to a solution of boron trichloride (1.0 M in xylenes; 36.6 mL, 36.6 mmol) in benzene (40 mL) at 0° C. under a nitrogen atmosphere. Once the addition was complete, the resulting mixture was heated at reflux for 2 hours and then recooled to 0° C. A solution of 1-naphthaldehyde (5.72 g, 36.6 mmol, 5.0 mL), triethylamine (6.74 g, 66.6 mmol, 9.3 mL) and benzene (15 mL) was then added and the resulting mixture stirred 1 hour before diluting with ethyl acetate and aqueous 2N hydrochloric acid. The resulting mixture was shaken vigorously, the aqueous layer alkalized with aqueous 5N sodium hydroxide, and the layers separated. The aqueous layer was extracted with ethyl acetate (2×). The organic layers were combined, dried over anhydrous sodium sulfate, filtered, concentrated under reduced pressure, and purified by flash column chromatography (5:1 hexanes/ethyl acetate) to produce 7.95 g (67%) of the title compound as a pale yellow solid.

MS (PCl): 354.

$^1$H NMR (250 MHz, CDCl$_3$) δ 8.00 (m, 1H), 7.89 (m, 2H), 7.51 (m, 4H), 7.15 (dd, 1H), 6.93 (d, 1H), 6.64 (d, 1H), 6.51 (s, 1H), 4.42 (br s, 1H), 2.83 (s, 2H), 2.38 (br s, 1H), 0.84 (s, 9H).

EXAMPLE 1C

3-[[4-Chloro-2-(hydroxy-naphthalen-1-yl-methyl)-phenyl]-neopentyl-carbamoyl]-acrylic acid ethyl ester Fumaric chloride monoethyl ester (5.48 g, 33.7 mmol) was added to a mixture of (5-chloro-2-neopentylamino-phenyl)-naphthalen-1-yl-methanol (7.95 g, 22.5 mmol) and sodium bicarbonate (3.77 g, 45.0 mmol) in methylene chloride (45 mL). After stirring 18 hours at ambient temperature, the reaction mixture was diluted with methylene chloride, washed with water (2×) and saturated aqueous sodium chloride, dried over anhydrous sodium sulfate, filtered, concentrated under reduced pressure, and purified by flash column chromatography (5:1 hexanes/ethyl acetate) to produce 10.12 g (94%) of the title compound as a pale yellow foam.

MS (PCl): 480.

$^1$H NMR (250 MHz, CDCl$_3$, major rotamer) δ 7.85–7.69 (m, 4H), 7.58–7.15 (m, 6H), 6.51 (d, 1H), 6.18 (d, 2H), 4.44 (d, 1H), 4.06 (qd, 2H), 3.20 (d, 1H), 2.58 (d, 1H), 1.21 (t, 3H), 0.92 (s, 9H).

EXAMPLE 1D

Ethyl ester of trans-7-chloro-5-(naphthalen-1-yl)-1-neopentyl-1,2,3,5-tetrahydro-2-oxo-4,1-benzoxazepine-3-acetic acid Potassium carbonate (5.82 g, 42.2 mmol) was added to a solution of 3-[[4-chloro-2-(hydroxy-naphthalen-1-yl-methyl)-phenyl]-neopentyl-carbamoyl]-acrylic acid ethyl ester (10.1 g, 21.1 mmol) in ethanol (60 mL). The resulting mixture was stirred at ambient temperature for 12 hours and concentrated under reduced pressure. The resulting residue was taken up in ether, washed with water (2×) and saturated aqueous sodium chloride, dried over anhydrous sodium sulfate, filtered, concentrated under reduced pressure, and purified by flash column chromatography (5:1 hexanes/ethyl acetate) to produce 8.75 g (86%) of the title compound as a white solid.

MS (PCl): 481 (M+H$^+$).

$^1$H NMR (250 MHz, CDCl$_3$) δ 7.91 (d, 2H), 7.84 (d, 1H), 7.59 (t, 1H), 7.51–7.30 (m, 5H), 6.63 (s, 1H), 6.53 (d, 1H), 4.56 (m, 2H), 4.15 (qd, 2H), 3.48 (d, 1H), 3.09 (dd, 1H), 2.86 (dd, 1H), 1.26 (t, 3H), 1.04 (s, 9H).

The title compounds of Examples 2–6 were prepared according to procedures analogous to those described in Example 1.

EXAMPLE 2

Ethyl ester of trans-7.8-methylenedioxy-5-(naphthalen-1-yl)-1-neopentyl-1,2,3,5-tetrahydro-2-oxo-4,1-benzoxazepine-3-acetic acid 87% yield.

MS (PCl): 491 (M+H$^+$).

$^1$H NMR (250 MHz, CDCl$_3$) δ 7.86 (m, 3H), 7.55 (m, 2H), 7.44 (m, 1H), 7.32 (td, 1H), 6.93 (s, 1H), 6.58 (s, 1H), 5.97 (s, 1H), 5.87 (d, 2H), 4.57 (m, 2H), 4.15 (m, 2H), 3.37 (d, 1H), 3.08 (dd, 1H), 2.86 (dd, 1H), 1.26 (t, 3H), 1.07 (s, 9H).

EXAMPLE 3

Ethyl ester of trans-7-chloro-5-(1-bromonaphthalen-2-yl)-1-neopentyl-1,2,3,5-tetrahydro-2-oxo-4,1-benzoxazepine-3-acetic acid 90% yield.

MS (PCl): 560 (M+H$^+$).

$^1$H NMR (250 MHz, CDCl$_3$) δ 8.30 (m, 1H), 7.88 (m, 3H), 7.62 (m, 2H), 7.37 (s, 2H), 6.54 (s, 1H), 6.52 (s, 1H), 4.54 (m, 2H), 4.16 (m, 2H), 3.44 (d, 1H), 3.05 (dd, 1H), 2.84 (dd, 1H), 1.26 (t, 3H), 1.01 (s, 9H).

EXAMPLE 4

Ethyl ester of trans-7-chloro-5-(4-methoxynaphthalen-1-yl)-1-neopentyl-1,2,3,5-tetrahydro-2-oxo-4,1-benzoxazepine-3-acetic acid 67% yield.

MS (PCl): 510.

$^1$H NMR (300 MHz, CDCl$_3$) δ 8.36 (m, 1H), 7.73 (d, 1H), 7.40 (m, 5H), 6.91 (d, 1H), 6.60 (d, 1H), 6.54 (s, 1H), 4.46 (m, 2H), 4.15 (qd, 2H), 4.06 (s, 3H), 3.48 (d, 1H), 3.09 (dd, 1H), 2.85 (dd, 1H), 1.26 (t, 3H), 1.04 (s, 9H).

EXAMPLE 5

Ethyl ester of trans-7-chloro-5-(4-hydroxynaphthalen-1-yl)-1-neopentyl-1,2,3,5-tetrahydro-2-oxo-4,1-benzoxazepine-3-acetic acid 67% yield.

MS (PCl): 496.

$^1$H NMR (300 MHz, CDCl$_3$) δ 8.33 (d, 1H), 7.62 (d, 1H), 7.38 (m, 5H), 6.95 (d, 1H), 6.61 (s, 1H), 6.56 (s, 1H), 4.59 (m, 2H), 4.18 (m, 2H), 3.45 (d, 1H), 1H), 2.89 (dd, 1H), 1.24 (t, 3H), 1.03 (s, 9H).

EXAMPLE 5A

Ethyl ester of trans-7-chloro-5-(4-dimethylamino-naphthalen-1-yl)-1-neopentyl-1,2,3,5-tetrahydro-2-oxo-4,1-benzoxazepine-3-acetic acid 81% yield.

MS (PCl): 523.

$^1$H NMR (300 MHz, CDCl$_3$) δ 8.33 (d, 1H), 7.72 (d, 1H), 7.49–7.28 (m, 5H), 7.16 (d, 1H), 6.63 (d, 1H), 6.55 (s, 1H), 4.56 (m, 2H), 4.15 (qd, 2H), 3.47 (d, 1H), 3.08 (dd, 1H), 2.94 (s, 6H), 2.84 (d, 1H), 1.26 (t, 3H), 1.03 (s, 9H).

EXAMPLE 5B

Ethyl ester of trans-7-methyl-5-(naphthalen-1-yl)-1-neopentyl-1,2,3,5-tetrahydro-2-oxo-4 1-benzoxazepine-3-acetic acid 88% yield.

MS (PCl): 461 (M+2H$^+$).

1H NMR (300 MHz, CDCl$_3$) δ 7.88 (m, 3H), 7.57 (m, 2H), 7.44 (td, 1H), 7.31 (m, 2H), 7.16 (dd, 1H), 6.66 (s, 1H), 6.35 (d, 1H), 4.57 (m, 2H), 4.15 (m, 2H), 3.52 (d, 1H), 3.08 (dd, 1H), 2.87 (dd, 1H), 2.03 (s, 3H), 1.25 (t, 3H), 1.05 (s, 9H).

EXAMPLE 5C

Ethyl ester of trans-7-chloro-5-(5-iodonaphthalen-1-yl)-1-neopentyl-1,2,3,5-tetrahydro-2-oxo-4,1-benzoxazepine-3-acetic acid 86% yield.

MS (PCl): 606 (M+H$^+$).

$^1$H NMR (300 MHz, CDCl$_3$) δ 8.22 (d,1H), 8.08 (d,$_1$H), 7.90 (d, 1H), 7.67 (t,1H), 7.43 (m, 3H), 7.01 (t, 1H), 6.59 (s, 1H), 6.46 (d, 1H), 4.56 (m, 2H), 4.15 (qd, 2H), 3.48 (d, 1H), 3.07 (dd, 1H), 2.85 (dd, 1H), 1.26 (t, 3H), 1.02 (s, 9H).

EXAMPLE 5D

Ethyl ester of trans-7-methylthio-5-(1-naphthyl)-1-neopentyl-2-oxo-1,2,3,5-tetrahydro-4,1-benzoxazepin-3-acetic acid 89% yield.

$^1$H NMR (250 MHz, CDCl$_3$) δ 1.03 (s, 9H); 1.25 (t, 3H); 2.07 (s, 3H); 2.85 (q, 1H); 3.08 (q, 1H); 3.48 (d, 1H); 4.14 (c, 2H); 4.53, 4.46, 4.58, 4.61 (m, 2H); 6.4 (d, 1H); 6.63 (s, 1H); 7.23 (m, 1H); 7.33 (q, 2H); 7.44 (t, 1H); 7.56 (c, 2H); 7.82 (d, 1H); 7.89 (d, 2H).

EXAMPLE 5E

Ethyl ester of trans 7-trifluoromethoxy-5-(1-naphthyl)-1-neopentyl-2-oxo-1,2,3,5-tetrahydro-4,1-benzoxazepin-3-acetic acid 43% yield.

$^1$H NMR (250 MHz, CDCl$_3$) δ 1.04 (s, 9H); 1.25 (t, 3H); 2.87 (q, 1H); 3.11 (q, 1H); 3.5 (d, 1H); 4.15 (q, 2H); 4.55, 4.57, 4.59, 5.62 (m, 2H); 6.38 (d, 1H); 6.63 (s, 1H); 7.23 (c, 1H); 7.31 (t, 1H); 7.46 (c, 3H); 7.58 (t, 1H); 7.83 (d, 1H); 7.91 (d, 2H).

EXAMPLE 5F

Ethyl ester of trans-7,8-ethylenedioxy-5-(1-naphthyl)-1-neopentyl-2-oxo-1,2,3,5-tetrahydro-4,1-benzoxazepin-3-acetic acid 18% yield.

$^1$H NMR (250 MHz, CDCl$_3$) δ 1.05 (s, 9H); 1.26 (t, 3H); 2.85 (q, 1H); 3.06 (q, 1H); 3.38 (d, 1H); 4.04, 4.25 (c, 6H); 4.52 (d, 1H); 4.59 (t, 1H); 6.03 (s, 1H); 6.59 (s, 1H); 6.93 (s, 1H); 7.33 (t, 1H); 7.44 (t, 1H); 7.56 (q, 2H); 7.8 (d, 1H); 7.87 (t, 2H).

EXAMPLE 5G

Ethyl ester of trans-7-trifluoromethyl-5-(1-naphthyl)-1-neopentyl-2-oxo-1,2,3,5-tetrahydro-4,1-benzoxazepin-3-acetic acid The title compound was prepared using the procedures described in Examples 1C and 1D.

73% yield.

$^1$H NMR (250 MHz, CDCl$_3$) δ 1.05 (s, 9H); 1.26 (t, 3H); 2.87 (q, 1H); 3.12 (q, 1H); 3.57 (d, 1H); 4.15 (m, 2H); 4.54 (q, 1H); 4.61 (d, 1H); 6.67 (s, 1H); 6.83 (s, 1H); 7.31 (t, 1H); 7.44 (d, 2H); 7.61 (m, 3H); 7.86 (d, 1H); 7.92 (d, 2H).

EXAMPLE 6

Ethyl ester of trans-7,8-trimethylene-5-(naphthalen-1-yl)-1-neopentyl-1,2,3,5-tetrahydro-2-oxo-4,1-benzoxazepine-3-acetic acid 93% yield.

MS (PCl): 487 (M+H$^+$).

$^1$H NMR (300 MHz, CDCl$_3$) δ 7.87 (m, 3H), 7.63–7.29 (m, 5H), 6.69 (s, 1H), 6.41 (s, 1H), 4.61 (m, 2H), 4.17 (m, 4H), 3.55 (d, 1H), 3.12 (dd, 1H), 2.89 (m, 3H), 2.57 (m, 2H), 1.98 (m, 2H), 1.26 (t, 3H), 1.08 (s, 9H).

EXAMPLE 6A

Methyl ester of trans-7-chloro-5-(4-methylamino-naphthalen-1-yl)-1-neopentyl-1,2,3,5-tetrahydro-2-oxo-4,1-benzoxazepine-3-acetic acid α-Chloroethyl chloroformate (109 mg, 765 μmol, 83 μL) was added to a solution of the ethyl ester of trans-7-chloro-5-(4-dimethylamino-naphthalen-1-yl)-1-neopentyl-1,2,3,5-tetrahydro-2-oxo-4,1-benzoxazepine-3-acetic acid (364 mg, 696 μmol) in 1,2- dichloroethane (3.5 mL) at 0° C. The resulting mixture was heated at reflux. After 4 hours, additional ACE-Cl (380 μL) was added. ACE-Cl (750 μL) was added both the following morning and the morning after that. On the third morning, the brown reaction mixture was cooled to ambient temperature and concentrated under reduced pressure to a brown foam which was taken up in methanol (7 mL) and heated at reflux for 4 hours, cooled to ambient temperature, concentrated under reduced pressure, and purified by flash column chromatography (2:1 hexanes/ethyl acetate with 1% triethylamine) to give 279 mg (81%) of the title compound as a beige foam.

MS (PCl): 495.

$^1$H NMR (300 MHz, CDCl$_3$) δ 7.86 (d, 1H), 7.68 (d, 1H), 7.50 (d, 1H), 7.43–7.29 (m, 4H), 6.68 (m, 2H), 6.52 (s, 1H), 4.56 (m, 3H), 3.69 (s, 3H), 3.46 (d, 1H), 3.10 (dd, 1H), 3.05 (s, 3H), 2.87 (dd, 1H), 1.03 (s, 9H).

EXAMPLE 6B

Ethyl ester of trans-7-chloro-5-(4-phenylnaphthalen-1-yl)-1-neopentyl-1,2,3,5-tetrahydro-2-oxo-4,1-benzoxazepine-3-acetic acid

EXAMPLE 6B1

Ethyl ester of trans-7-chloro-5-(4-trifluoromethanesulfonyloxy-naphthalen-1-yl)-1-neopentyl-1,2,3,5-tetrahydro-2-oxo-4,1-benzoxazepine-3-acetic acid Trifluoromethanesulfonic anhydride (208 mg, 739 μmol, 120 μL) was added to a solution of the ethyl ester of trans-7-chloro-5-(4-hydroxynaphthalen-1-yl)-1-neopentyl-1,2,3,5-tetrahydro-2-oxo-4,1-benzoxazepine-3-acetic acid (305 mg, 616 μmol), pyridine (195 mg, 2.46 mmol, 200 μL) and methylene chloride (3 mL) at 0° C. The orange mixture was gradually warmed to ambient temperature and stirred for 5 hours, diluted with ether, washed with water (2×) and saturated aqueous sodium chloride, dried over anhydrous sodium sulfate, filtered, concentrated under reduced pressure, and purified by flash column chromatography (4:1 hexanes/ethyl acetate) to afford 356 mg (92%) of the title compound as a white solid.

$^1$H NMR (250 MHz, CDCl$_3$) δ 8.17 (d, 1H), 7.90 (d, 1H), 7.67–7.36 (m, 6H), 6.59 (s, 1H), 6.47 (s, 1H), 4.56 (m, 2H), 4.15 (qd, 2H), 3.49 (d, 1H), 3.07 (dd, 1H), 2.85 (dd, 1H), 1.26 (t, 3H), 1.03 (s, 9H).

EXAMPLE 6B2

Ethyl ester of trans-7-chloro-5-(4-phenylnaphthalen-1-yl)-1-neopentyl-1,2,3,5-tetrahydro-2-oxo-4,1-benzoxazepine-3-acetic acid To a solution of the ethyl ester of trans-7-chloro-5-(4-trifluoromethanesulfonyloxy-naphthalen-1-yl)-1-neopentyl-1,2,3,5-tetrahydro-2-oxo-4,1-benzoxazepine-3-acetic acid (160 mg, 255 μmol) in toluene (2.5 mL) was successively added tetrakis(triphenylphosphine)palladium(0) (9.4 mg, 8.2 μmol), 2M aqueous sodium carbonate (330 μL, 663 μmol), ethanol (1 mL), boronic acid (34.2 mg, 280 μmol) and lithium chloride (21.6 mg, 510 μmol). The resulting orange solution was heated at 95° C. for 28 hours. The black solution was cooled to ambient temperature, diluted with ethyl acetate, washed with 1N aqueous sodium hydroxide and saturated aqueous sodium chloride, dried over anhydrous sodium sulfate, filtered, concentrated under reduced pressure, and purified by flash column chromatography (4:1 hexanes/ethyl acetate) to afford 137 mg (97%) of the title compound as a white solid.

MS (PCl): 556.

$^1$H NMR (300 MHz, CDCl$_3$) δ 8.01 (d, 1H), 7.94 (d, 1H), 7.63–7.34 (m, 11H), (d, 1H), 6.71 (s, 1H), 4.63 (m, 2H), 4.18 (m, 2H), 3.53 (d, 1H), 3.15 (dd, 1H), 2.92 (dd, 1H), 1.28 (t, 3H), 1.09 (s, 9H).

EXAMPLE 6C

Ethyl ester of trans-7-chloro-5-(4-carboxynaphthalen-1-yl)-1-neopentyl-1,2,3,5-tetrahydro-2-oxo-4,1-benzoxazepine-3-acetic acid A solution of the ethyl ester of trans-7-chloro-5-(4-trifluoromethanesulfonyloxy-naphthalen-1-yl)-1-neopentyl-1,2,3,5-tetrahydro-2-oxo-4,1-benzoxazepine-3-acetic acid (152 mg, 242 μmol), potassium acetate (95 mg, 968 μmol), palladium (II) acetate (3 mg, 12 μmol), 1,1'-bis (diphenylphosphino)-ferrocene (27 mg, 48 μmol) and dimethyl sulfoxide (3 mL) at 60° C. was purged with carbon monoxide gas for 10 minutes and then maintained under a carbon monoxide atmosphere for 3 hours. The reaction mixture was diluted with water and extracted with ethyl acetate (3×). The combined organics were dried over anhydrous magnesium sulfate, filtered, concentrated under reduced pressure, and purified by prep plate (80:15:1 chloroform/methanol/saturated ammonium hydroxide) to afford 99 mg (78%) of the title compound as a beige solid.

MS (PCl): 524.

$^1$H NMR (250 MHz, CDCl$_3$) δ 9.17 (d, 1H), 8.51 (d, 1H), 7.98 (d, 1H), 7.66–7.34 (m, 5H), 6.68 (s, 1H), 6.48 (d, 1H), 4.58 (m, 2H), 4.18 (qd, 2H), 3.51 (d, 1H), 3.12 (dd, 1H), 2.90 (dd, 1H), 1.27 (t, 3H), 1.06 (s, 9H).

EXAMPLE 6D

Ethyl ester of trans-7-chloro-5-(5-methylnaphthalen-1-yl)-1-neopentyl-1,2,3,5-tetrahydro-2-oxo-4,1-benzoxazepine-3-acetic acid Methyllithium (1.4 M in ether; 310 μL, 431 μmol) was added to a solution of 1-aza-5-stannabicyclo[3.3.3]undecane chloride (127 mg, 431 μmol) and ether (2 mL) at 0° C. The resulting mixture was stirred 30 minutes at 0° C. and then warmed to ambient temperature and stirred an additional 30 minutes before concentrating under reduced pressure. The resulting residue was taken up with the ethyl ester of trans-7-chloro-5-(5-iodonaphthalen-1-yl)-1-neopentyl-1,2,3,5-tetrahydro-2-oxo-4,1-benzoxazepine-3-acetic acid (218 mg, 359μmol), [1,1'-bis(diphenylphosphino)ferrocene] palladium (II) chloride complex with dichloromethane (1:1) (5.8 mg, 7.2 μmol) and toluene (5 mL) and this mixture heated at reflux for 18 hours. The reaction mixture was cooled to ambient temperature, diluted with ether, washed with 0.2 N aqueous hydrochloric acid, dried over anhydrous sodium sulfate, concentrated under reduced pressure and purified by flash column chromatography (5:1 hexanes/ethyl acetate) to provide 34 mg (19%) of the title compound as a white powder.

1H NMR (250 MHz, CDCl$_3$) δ 8.09 (d, 1H), 7.86 (d, 1H), 7.62 (dd, 1H), 7.48–7.17 (m, 5H), 6.63 (s, 1H), 6.52 (d, 1H), 4.56 (m, 2H), 4.16 (qd, 1H), 3.48 (d, 1H), 3.09 (dd, 1H), 2.86 (dd, 1H), 2.74 (s, 3H), 1.26 (t, 3H), 1.04 (s, 9H).

EXAMPLE 6E

Ethyl ester of trans-7-chloro-5-(5-phenylnaphthalen-1-yl)-1-neopentyl-1,2,3,5-tetrahydro-2-oxo-4,1-benzoxazepine-3-acetic acid Reaction performed in a manner similar to that described in Example 6B2 using the ethyl ester of trans-7-chloro-5-(5-iodonaphthalen-1-yl)-1-neopentyl-1,2,3,5-tetrahydro-2-oxo-4,1-benzoxazepine-3-acetic acid as starting material under nonaqueous conditions using cesium fluoride instead of lithium chloride and dimethylformamide as the solvent.

quantitative yield.

$^1$H NMR (300 MHz, CDCl$_3$) δ 7.96 (d, 1H), 7.85 (d, 1H), 7.55–7.36 (m, 11H), (s, 1H), 6.62 (d, 1H), 4.58 (m, 2H), 4.15 (qd, 2H), 3.50 (d, 1H), 3.10 (dd, 1H), 2.86 (dd, 1H), 1.26 (t, 3H), 1.06 (s, 9H).

EXAMPLE 6F

Ethyl ester of trans-7-chloro-5-(5-acetylnaphthalen-1-yl)-1-neopentyl-1,2,3,5-tetrahydro-2-oxo-4,1-benzoxazepine-3-acetic acid A mixture of the ethyl ester of trans-7-chloro-5-(5-iodonaphthalen-1-yl)-1-neopentyl-1,2,3,5-tetrahydro-2-oxo-4,1-benzoxazepine-3-acetic acid (204 mg,337 μmol), bis(triphenylphosphine)palladium (II) chloride (24 mg, 34μmol), (1-ethoxyvinyl)tributyltin (134 mg, 370 μmol, 125 μL) and toluene (2 mL) was heated at 100° C. for 48 hours under a nitrogen atmosphere and cooled to ambient temperature. Aqueous 2 N hydrochloric acid (2 mL) was added and the resulting mixture stirred 24 hours before diluting with ether, washing with water, drying over anhydrous sodium sulfate, concentrating under reduced pressure and purifying by flash column chromatography (3:1 hexanes/ ethyl acetate) to provide 163 mg (92%) of the title compound as a light brown foam.

MS (PCl): 522 (M+H$^+$).

$^1$H NMR (250 MHz, CDCl$_3$) δ 8.70 (d, 1H), 7.87 (m, 2H), 7.69 (m, 2H), 7.37 (m, 3H), 6.60 (s, 1H), 6.48 (d, 1H), 4.56 (m, 2H), 4.14 (qd, 2H), 3.48 (d, 1H), 3.07 (dd, 1H), 2.85 (dd, 1H), 2.76 (s, 3H), 1.25 (t, 3H), 1.03 (s, 9H).

EXAMPLE 7

Ethyl ester of trans-7,8-trimethylene-5-(naphthalen-1-yl)-1-neopentyl-1,2,3,5-tetrahydro-4,1-benzoxazepine-3-acetic acid

EXAMPLE 7A

4-[[4,5-Trimethylene-2-(hydroxy-naphthalen-1-yl-methyl)-phenyl]-(neopentyl)-amino]-but-2-enoic acid ethyl ester Ethyl 4-bromocrotonate (203 mg, 1.05 mmol, 145 μL) was added to a mixture of (4,5-trimethylene-2-neopentylamino-phenyl)-naphthalen-1-yl-methanol (344 mg, 956 μmol; prepared as described in example 1) and potassium carbonate (159 mg, 1.15 mmol) in dimethylformamide (2 mL) at ambient temperature. After stirring 20 hours, an additional amount of potassium carbonate (1.32 g, 956 mmol) and ethyl 4-bromocrotonate (922 mg, 4.78 mmol, 658 μL) was added. After an additional 18 hours, the reaction mixture was diluted with ether, washed successively with water (2×) and saturated aqueous sodium chloride, dried over anhydrous sodium sulfate, filtered, concentrated under reduced pressure, and purified by flash column chromatography (5:1 hexanes/ethyl acetate) to produce 193 mg (43%) of the title compound.

EXAMPLE 7B

Ethyl ester of trans-7,8-trimethylene-5-(naphthalen-1-yl)-1-neopentyl-1,2,3,5-tetrahydro-4,1-benzoxazeline-3-acetic acid 4-[[4,5-Trimethylene-2-(hydroxy-naphthalen-1-yl-methyl)-phenyl]-(neopentyl)-amino]-but-2-enoic acid ethyl ester (193 mg, 408 μmol) was taken up in ethanol (3 mL) and potassium carbonate (113 mg, 817 μmol) and stirred at ambient temperature for 16 hours. The reaction mixture was diluted with ethyl acetate, washed successively with water (2×) and saturated aqueous sodium chloride, dried over anhydrous sodium sulfate, filtered, concentrated under reduced pressure, and purified by flash column chromatography (10:1 hexanes/ethyl acetate) to produce 127 mg (66%) of the title compound as an off-white solid.

MS (PCl): 472.

$^1$H NMR (300 MHz, CDCl$_3$) δ 8.12 (d, 1H), 7.97 (m, 2H), 7.74.(d, 1H), 7.50 (m, 3H), 7.00 (s, 1H), 6.33 (br s, 1H), 6.29 (s, 1H), 5.13 (dd, 1H), 4.12 (q, 2H), 3.65 (d, 1H), 2.91 (m, 3H), 2.63 (t, 2H), 2.40 (t, 2H), 2.31–1.87 (m, 4H), 1.25 (t, 3H), 1.09 (s, 9H).

EXAMPLE 8

Ethyl ester of trans-7-chloro-5-(naphthalen-1-yl)-1-neopentyl-1,2,3,5-tetrahydro-4,1-benzoxazepine-3-acetic acid The title compound was prepared as described in example 7 except using 10 equivalents of potassium carbonate and 5 equivalents of ethyl 4-bromocrotonate initially and stirring at ambient temperature for 72 hours.

27% yield for 2 steps.

MS (PCl): 466 (M+H⁺).

¹H NMR (250 MHz, CDCl₃) δ 8.28 (d, 1H), 7.87 (d, 2H), 7.45 (m, 4H), 7.04 (dd, 1H), 6.85 (d, 1H), 6.62 (d, 1H), 6.32 (s, 1H), 4.92 (dd, 1H), 4.14 (q, 2H), 3.55 (d, 1H), 2.86 (d, 1H), 2.54 (m, 2H), 2.34 (m, 1H) 2.11 (m, 1H), 1.25 (t, 3H), 1.12 (s, 9H).

EXAMPLE 9

Trans-7-chloro-5-(naphthalen-1-yl)-1-neopentyl-1,2,3,5-tetrahydro-2-oxo-4,1-benzoxazepine-3-acetic acid Potassium carbonate (5.03 g, 36.5 mmol) was added to a solution of the ethyl ester of the title compound (18.75 g, 18.2 mmol) in methanol (60 mL) and water (10 mL). The resulting mixture was heated at 60° C. for 18 hours. After cooling to room temperature, the reaction mixture was concentrated and the resulting residue taken up in water, acidified with an aqueous solution of 1N hydrochloric acid and extracted with ethyl acetate (3×). The combined organics were dried over anhydrous magnesium sulfate, filtered, concentrated under reduced pressure, and purified by flash column chromatography (80:15:1 chloroform/methanol/saturated ammonium hydroxide) to produce a clear oil that was taken up in ethyl acetate, washed with an aqueous solution of 1N hydrochloric acid, dried over anhydrous magnesium sulfate, filtered through a pad of Celite, and concentrated under reduced pressure. The resulting solid was triturated with ether/hexanes to give 7.39 g (89%) of the title compound as a white solid.

MS (PCl): 453 (M+H⁺).

¹H NMR (250 MHz, CDCl₃) δ 7.89 (m, 3H), 7.60 (t, 1H), 7.49–7.30 (m, 5H), 6.63 (s, 1H), 6.54 (d, 1H), 4.58 (d, 1H), 4.51 (dd, 1H), 3.50 (d, 1H), 3.14 (dd, 1H), 2.93 (dd, 1H), 1.05 (s, 9H).

The title compounds of Examples 10–16 were prepared according to procedure analogous to those described in Example 9.

EXAMPLE 10

Trans-7,8-methylenedioxy-5-(naphthalen-1-yl)-1-neopentyl-1,2,3,5-tetrahydro-2-oxo-4,1-benzoxazepine-3-acetic acid 66% yield.

MS (PCl): 463 (M+H⁺).

¹H NMR (250 MHz, CDCl₃) δ 7.87 (m, 3H), 7.56 (m, 2H), 7.45 (t, 1H), 7.32 (m, 1H), 6.93 (s, 1H), 6.58 (s, 1H), 5.98 (s, 1H), 5.91 (d, 2H), 4.54 (m, 2H), 3.39 (d, 1H), 3.13 (dd, 1H), 2.93 (dd, 1H), 1.07 (s, 9H).

EXAMPLE 10B

Trans-7-methyl-5-(naphthalen-1-yl)-1-neopentyl-1,2,3,5-tetrahydro-2-oxo-4,1-benzoxazepine-3-acetic acid 81% yield.

MS (PCl): 433 (M+2H⁺).

¹H NMR (300 MHz, CDCl₃) δ 7.78 (m, 3H), 7.56 (m, 2H), 7.44 (t, 1H), 7.31 (m, 2H), 7.18 (m, 1H), 6.65 (s, 1H), 6.36 (d, 1H), 4.57 (d, 1H), 4.51 (dd, 1H), 3.53 (d, 1H), 3.13 (dd, 1H), 2.93 (dd, 1H), 2.05 (s, 3H), 1.05 (s, 9H).

EXAMPLE 10C

Trans-7-methoxy-5-(naphthalen-1-yl)-1-neopentyl-1,2,3,5-tetrahydro-2-oxo-4,1-benzoxazepine-3-acetic acid 78% yield.

MS (PCl): 449 (M+2H⁺).

¹H NMR (250 MHz, DMSO-d₆) δ 8.02 (d, 2H), 7.80 (d, 1H), 7.66 (m, 2H), 7.45 (m, 3H), 7.05 (dd, 1H), 6.46 (s, 1H), 5.81 (d, 1H), 4.37 (m, 2H), 3.67 (d, 1H), 3.47 (s, 3H), 2.85 (dd, 1H), 2.70 (dd, 1H), 0.96 (s, 9H).

EXAMPLE 10D

Trans-7-chloro-5-(5-iodonaphthalen-1-yl)-1-neopentyl-1,2,3,5-tetrahydro-2-oxo-4,1-benzoxazepine-3-acetic acid 98% yield.

MS (PCl): 578 (M+H⁺).

¹H NMR (300 MHz, CDCl₃) δ 8.21 (d,1H), 8.08 (d, 1H), 7.90 (d, 1H), 7.67 7.43 (m, 3H), 7.00 (t, 1H), 6.59 (s, 1H), 6.47 (s, 1H), 4.57 (d, 1H), 4.50 (t 1H), 3.10 (dd, 1H), 2.95 (dd, 1H), 1.03 (s, 9H).

EXAMPLE 10E

Trans-7-chloro-5-(5-methylnaphthalen-1-yl)-1-neopentyl-1,2,3,5-tetrahydro-2-oxo-4,1-benzoxazepine-3-acetic acid 98% yield.

¹H NMR (250 MHz, CDCl₃) δ 8.10 (d, 1H), 7.90 (d, 1H), 7.65 (t, 1H), 7.50–7.20 (m, 5H), 6.65 (s, 1H), 6.55 (d, 1H), 4.50 (m, 2H), 3.50 (d, 1H), 3.15 (dd, 1H), 2.90 (dd, 1H), 2.75 (s, 3H), 1.05 (s, 9H).

EXAMPLE 10F

Trans-7-chloro-5-(5-phenylnaphthalen-1-yl)-1-neopentyl-1,2,3,5-tetrahydro-2-oxo-4,1-benzoxazepine-3-acetic acid 86% yield.

MS (PCl): 528 (M+H⁺).

¹H NMR (250 MHz, CDCl₃) δ 7.96 (d,1H), 7.86 (d, 1H), 7.56–7;33 (m, 11H), 6.66 (s, 1H), 6.63 (d, 1H), 4.59 (d, 1H), 4.53 (dd, 1H), 3.51 (d, 1H), 3.16 (dd, 1H), 2.94 (dd, 1H), 1.06 (s, 9H).

EXAMPLE 10G

Trans-7-chloro-5-(5-acetylnaphthalen-1-yl)-1-neopentyl-1,2,3,5-tetrahydro-2-oxo-4,1-benzoxazepine-3-acetic acid 53% yield.

MS (PCl): 494 (M+H⁺).

¹H NMR (300 MHz, CDCl₃) δ 8.69 (d,1H), 7.87 (m, 2H), 7.70 (nm, 2H), 7.44 (m, 3H), 6.60 (s, 1H), 6.49 (d,,1H), 4.54 (m, 2H), 3.48 (d, 1H), 3.14 (dd, 1H), 2.92 (dd, 1H), 2.75 (s, 3H), 1.03 (s, 9H).

EXAMPLE 11

Trans-7-chloro-5-(1-bromonaphthalen-2-yl)-1-neopentyl-1,2,3,5-tetrahydro-2-oxo-4,1-benzoxazepine-3-acetic acid 62% yield.

MS (PCl): 532 (M+H⁺).

¹H NMR (250 MHz, CD₃OD) δ 8.28 (m, 1H), 7.96 (m, 3H), 7.63 (m, 3H), 7.44 (dd, 1H), 6.48 (s, 1H), 6.37 (d, 1H), 4.53 (m, 1H), 4.46 (d, 1H), 3.62 (d, 1H), 2.76 (m, 2H), 1.00 (s, 9H).

EXAMPLE 12

Trans-7-chloro-5-(4-methoxynaphthalen-1-yl)-1-neopentyl-1,2,3,5-tetrahydro-2-oxo-4,1-benzoxazepine-3-acetic acid 96% yield.

MS (PCl): 482.

¹H NMR (300 MHz, CDCl₃) δ 8.37 (d, 1H), 7.75 (d, 1H), 7.40 (m, 5H), 6.92 (d, 1H), 6.61 (d, 1H), 6.56 (s, 1H), 4.55 (m, 2H), 4.04 (s, 3H), 3.48 (d, 1H), 3.15 (dd, 1H), 2.93 (dd, 1H), 1.04 (s, 9H).

EXAMPLE 13

Trans-7-chloro-5-(4-hydroxynaphthalen-1-yl)-1-neopentyl-1,2,3,5-tetrahydro-2-oxo-4,1-benzoxazepine-3-acetic acid 20% yield.

¹H NMR (300 MHz, CD₃OD) δ 8.32 (d, 1H), 7.65 (d, 1H), 7.58 (d, 1H), 7.39 (m, 4H), 6.93 (d, 1H), 6.46 (m, 2H), 4.48 (m, 2H), 3.63 (d, 1H), 2.83 (m, 2H), 1.02 (s, 9H).

EXAMPLE 13A

Trans-7-chloro-5-(4-dimethylamino-naphthalen-1-yl)-1-neopentyl-1,2,3,5-tetrahydro-2-oxo-4,1-benzoxazepine-3-acetic acid 92% yield.

MS (PCl): 495.

¹H NMR (300 MHz, CDCl₃) δ 8.32 (d, 1H), 7.74 (d, 1H), 7.46–7.30 (m, 5H), 7.17 (d, 1H), 6.64 (d, 1H), 6.55 (s, 1H), 4.57 (d, 1H), 4.50 (t, 1H), 3.48 (d, 1H), 3.12 (dd, 1H), 2.94 (s, 6H), 2.89 (app d, 1H), 1.03 (s, 9H).

EXAMPLE 13B

Trans-7-chloro-5-(4-methylamino-naphthalen-1-yl)-1-neopentyl-1,2,3,5-tetrahydro-2-oxo-4,1-benzoxazepine-3-acetic acid 70% yield.

MS (PCl): 481.

¹H NMR (300 MHz, CDCl₃) δ 7.86 (d, 1H), 7.70 (d, 1H), 7.51–7.29 (m, 5H), 6.69 (m, 2H), 6.52 (s, 1H), 4.57 (d, 1H), 4.52 (t,₁H), 3.47 (d, 1H), 3.15 (dd, 1H), 3.05 (s, 3H), 2.92 (dd, 1H), 1.03 (s, 9H).

EXAMPLE 13C

Trans-7-chloro-5-(4-phenylnaphthalen-1-yl)-1-neopentyl-1,2,3,5-tetrahydro-2-oxo-4,1-benzoxazepine-3-acetic acid 64% yield.

MS (PCl): 528.

¹H NMR (300 MHz, CD₃OD, major conformer) δ 7.95 (m, 2H), 7.89 (s, 2H), 7.69–7.32 (m, 9H), 6.62 (s, 1H), 6.49 (d, 1H), 4.49 (m, 2H), 3.70 (d, 1H), 2.98 (s, 1H), 2.85 (s, 1H), 1.06 (s, 9H).

EXAMPLE 13D

Trans-7-chloro-5-(4-carboxynaphthalen-1-yl)-1-neopentyl-1,2,3,5-tetrahydro-2-oxo-4,1-benzoxazepine-3-acetic acid 84% yield.

MS (PCl): 496.

¹H NMR (250 MHz, CD₃OD) δ 8.99 (d, 1H), 8.29 (d, 1H), 7.95 (d, 1H), 7.80 (d, 1H), 7.64–7.34 (m, 5H), 6.61 (s, ₁H), 6.36 (d, 1H), 4.49 (m, 2H), 3.65 (d, ₁H), 3.01 (dd, 1H), 2.85 (dd, 1H), 1.04 (s, 9H).

EXAMPLE 13E

Trans-7-chloro-5-(4-methoxycarbonylnaihthalen-1-yl)-1-neopentyl-1,2,3,5-tetrahydro-2-oxo-4,1-benzoxazepine-3-acetic acid The ethyl ester of the title compound was prepared using a procedure analogous to that described in example 6C using methanol (20 equivalents) and triethylamine (2 equivalents) in dimethylformamide-instead of dimethyl sulfoxide and potassium carbonate. Hydrolysis to the title compound was carried out using an analogous procedure to that described in Example 9.

MS (PCl): 510.

EXAMPLE 14

Trans-7,8-trimethylene-5-(naphthalen-1-yl)-1-neopentyl-1,2,3,5-tetrahydro-2-oxo-4,1-benzoxazepine-3-acetic acid 72% yield.

MS (PCl): 472.

¹H NMR (300 MHz, CD₃OD) δ 7.91 (dd, 2H), 7.85 (d, 1H), 7.50 (m, 4H), 7.28 (m, 1H), 6.58 (s, 1H), 6.27 (s, 1H), 4.48 (m, 2H), 3.69 (d, 1H), 2.96 (dd, 1H), 2.92 (t, 2H), 2.80 (dd, 1H), 2.55 (m, 2H), 1.98 (quintet, 2H), 1.04 (s, 9H).

EXAMPLE 15

Trans-7,8-trimethylene-5-(naphthalen-1-yl)-1-neopentyl-1,2,3,5-tetrahydro-4,1-benzoxazepine-3-acetic acid 85% yield.

MS (PCl): 444.

¹H NMR (300 MHz, CDCl₃) δ 8.37 (m, 1H), 7.86 (m, 2H), 7.49 (m, 4H), 6.88 (s, 1H), 6.54 (s, 1H), 6.42 (s, 1H), 4.92 (s, 1H), 3.59 (d, 1H), 2.87 (m, 3H), 2.62 (m, 4H), 2.42 (m, 1H), 2.12 (m, 1H), 1.97 (quintet, 2H), 1.14 (s, 9H).

EXAMPLE 16

Trans-7-chloro-5-(naphthalen-1-yl)-1-neopentyl-1,2,3,5-tetrahydro-4,1-benzoxazepine-3-acetic acid 56% yield MS (PCl): 438.

¹H NMR (250 MHz, CDCl₃) δ 8.26 (d, 1H), 7.86 (d, 2H), 7.54–7.36 (m, 4H), 7.04 (dd, 1H), 6.86 (d, 1H), 6.63 (d, 1H), 6.32 (s, 1H), 4.92 (dd, 1H), 3.54 (d, 1H), 2.84 (d, 1H), 2.59 (m, 2H), 2.34 (m, 1H), 2.09 (m, 1H), 1.11 (s, 9H).

EXAMPLE 17

Methyl ester of (−)-(R)-O-[trans-7-chloro-5-(naphthalen-1-yl)-1-neopentyl-2-oxo-1,2,3,5-tetrahydro-4,1-benzoxazepine-3-acetyl]]lactic acid and methyl ester of (+)-(R)-O-[trans-7-chloro-5-(naphthalen-1-yl)-1-neopentyl-2-oxo-1,2,3,5-tetrahydro-4,1-benzoxazepine-3-acetyl]]lactic acid 1-(3-Dimethylaminopropyl)-3-ethylcarbodiimide hydrochloride (309 mg, 1.61 mmol) and 4-dimethylaminopyridine (59 mg, 484 μmol) were added to a solution of trans-7-chloro-5-(naphthalen-1-yl)-1-neopentyl-2-oxo-1,2,3,5-tetrahydro-4,1-benzoxazepine-3-acetic acid (606 mg, 1.34 mmol) and methyl (R)-lactate (168 mg, 1.61 mmol) in methylene chloride (15 mL) at ambient temperature. After stirring 5 hours, the reaction mixture was diluted with ether, washed successively with aqueous solutions of 1N hydrochloric acid, saturated sodium bicarbonate and saturated sodium chloride, dried over anhydrous sodium sulfate, filtered, concentrated under reduced pressure, and purified by flash column chromatography (3:1 hexanes/ether, 200 mL silica).

As the less polar fraction, 268 mg of the methyl ester of (R)-O-[(+)-trans-7-chloro-5-(naphthalen-1-yl)-1-neopentyl-2-oxo-1,2,3,5-tetrahydro-4,1-benzoxazepine-3-acetyl]lactic acid was isolated as a white solid.

$[\alpha]_D^{25}$ +179.1° (c 0.92, chloroform).

$^1$H NMR (300 MHz, CDCl$_3$) δ 7.91 (m, 3H), 7.61 (t, 1H), 7.50–7.31 (m, 5H), 6.65 (s, 1H), 6.55 (d, 1H), 5.11 (q, 1H), 4.58 (m, 2H), 3.72 (s, 3H), 3.50 (d, 1H), 3.26 (dd, 1H), 2.99 (dd, 1H), 1.51 (d, 3H), 1.05 (s, 9H).

As the more polar fraction, 270 mg of the methyl ester of (R)-O-[(−)-trans-7-chloro-5-(naphthalen-1-yl)-1-neopentyl-2-oxo-1,2,3,5-tetrahydro-4,1-benzoxazepine-3-acetyl]lactic acid was isolated as a white solid.

$[\alpha]_D^{25}$ −132.1° (c 1.2, chloroform).

$^1$H NMR (300 MHz, CDCl$_3$) δ 7.91 (d, 2H), 7.86 (d, 1H), 7.63–7.32 (m, 6H), (s, 1H), 6.55 (d, 1H), 5.15 (q, 1H), 4.60 (m, 2H), 3.74 (s, 3H), 3.48 (d, 1H), 3.15 (dd, 1H), 3.02 (dd, 1H), 1.47 (d, 3H), 1.05 (s, 9H).

EXAMPLE 18

(−)-Trans-7-chloro-5-(naphthalen-1-yl-1-neopentyl-2-oxo-1,2,3,5-tetrahydro-4,1-benzoxazepine-3-acetic acid Potassium carbonate (137 mg, 994 μmol) and water (0.5 mL) were added to a solution of the methyl esterof (−)-(R)-O-[trans-7-chloro-5-(naphthalen-1-yl)-1-neopentyl- 2-oxo-1,2,3,5-tetrahydro-4,1-benzoxazepine-3-acetyl]lactic acid (268 mg, 497 μmol) in methanol (5 mL). The resulting mixture was heated at 60° C. for 14 hours and concentrated under reduced pressure. The resulting residue was taken up in water, acidified with an aqueous solution of 2N hydrochloric acid and extracted with ethyl acetate. The combined organics were dried over anhydrous sodium sulfate, filtered, concentrated under reduced pressure, and purified by flash column chromatography (5% methanol/methylene chloride) to yield 208 mg (93%) of a white solid.

$[\alpha]_D^{25}$ −159.9° (c 1.0, chloroform).

EXAMPLE 19

(+)-Trans-7-chloro-5-(naphthalen-1-yl)-1-neopentyl-2-oxo-1,2,3,5-tetrahydro-4,1-benzoxazepine-3-acetic acid The title compound was prepared according to a procedure analogous to that of Example 18.

89% yield.

$[\alpha]_D^{25}$ +185.5° (c 1.1, chloroform).

EXAMPLE 20

Trans-7-chloro-5-(1-naphthyl)-1-neopentyl-2-oxo-1,2,3,5-tetrahydro-4,1-benzothiazepin-3-acetic acid

EXAMPLE 20A (5-Chloro-2-neopentylamino)phenyl-(1-naphthyl)methylthiocilycolic acid A mixture of 6.0 g (17 mmol) (5-chloro-2-neopentylamino)phenyl-(1-naphthyl)methanol, 6 mL (86 mmol) mercaptoacetic acid and 50 mL 6N aqueous hydrochloric acid was heated at 100° C. for 5 hours under nitrogen. The reaction was cooled to room temperature, diluted with 200 mL water and stirred at room temperature for several hours. The mixture was then filtered, the solid was washed repeatedly with water and air-dried to yield 7.26 g (quantitative yield) of the desired product as a tan colored solid.

$^1$H NMR (CDCl$_3$) δ 0.9 (s, 9H); 2.86 (s, 2H); 3.24 (s, 2H); 6.46 (s, 1H); 7.0 (d, 1H); 7.1 (c, 2H); 7.42 (c, 4H); 7.78 (c, 4H).

EXAMPLE 20B

7-Chloro-5-(1-naphthyl)-1-neopentyl-2-oxo-1,2,3,5-tetrahydro-4,1-benzothiazepine To a solution of 7.26 ((17 mmol) (5-chloro-2-neopentylamino)phenyl-(1-naphthyl)methylthioglycolic acid in 800 mL dichloromethane was added 14.4 g (33.9 mmol) 1-cyclohexyl-3-(2-morpholinoethyl)carbodiimide metho-p-toluenesulfonate and the reaction mixture was stirred at room temperature under nitrogen overnight. TLC analysis indicated that the reaction had not gone to completion so another 3.6 g (8.5 mmol) of the carbodiimide was added and the reaction mixture stirred at room temperature overnight.

The reaction mixture was then concentrated in vacuo and the residue was partitioned between 200 mL ethyl acetate and 100 mL water. The ethyl acetate layer was washed sequentially with 2×100 mL water and 100 mL brine, dried over anhydrous sodium sulfate, filtered and concentrated in vacuo. The residue (7.8 g) was chromatographed on 700 g silica gel, eluting with 85:15 hexane/ethyl acetate to yield 4.84 g (69.5% yield) of the desired product.

$^1$ H NMR (CDCl$_3$) δ 1.11 (s, 9H); 3.08 (d, 1H); 3.34 (2d, 2H); 4.51 (d, 1H); 6.60 (s, 1H); 6.78 (d, 1H); 7.28 (c, 2H); 7.4 (t, 1H); 7.5 (t, 1H); 7.61 (t, 1H); 7.93 (t, 3H); 8.02 (d, 1H).

EXAMPLE 20C t-Butyl ester of trans-7-chloro-5-(1-naphthyl)-1-neopentyl-2-oxo-1,2,3,5-tetrahydro-4,1-benzothiazepin-3-acetic acid A solution of lithium diisopropylamide in cyclohexane [11.8 mL (17.7 mmol) of a 1.5M solution] was added slowly to a stirred solution of 4.84 g (11.8 mmol) 7-chloro-5-(1-naphthyl)-1-neopentyl-2-oxo-1,2,3,5,-tetrahydro-4,1-benzothiazepine in 225 mL anhydrous tetrahydrofuran cooled to -70° C. under nitrogen. The solution was stirred at −70° C. for 45 min, then 2.1 mL (13.0 mmol) t-butyl bromoacetate was slowly added and the resulting solution was allowed to warm to room temperature overnight. The reaction mixture was treated with 300 mL saturated aqueous ammonium chloride solution and 100 mL ethyl acetate and the organic phase separated. The aqueous phase was extracted with 3×200 mL ethyl acetate and the combined organic extracts were washed sequentially with 300 mL water and 230 mL brine, dried over anhydrous sodium sulfate, filtered and concentrated in vacuo. The residue (6.0 g) was chromatographed on 500 g silica gel, eluting with 9:1 hexane/ethyl acetate to yield 5.6 g (91% yield) of the title compound as a 5:2 mixture of cis and trans isomers.

A solution of 3.03 g (21.9 mmol) potassium carbonate in 60 mL water was added to a solution of 5.6 g (10.7 mmol) of the mixture of cis and trans isomers of the title compound dissolved in 225 mL methanol and the resulting solution was heated at 60° C. for 90 minutes The reaction mixture was cooled to room temperature, then concentrated in vacuo. Water (100 ml) was added to the residue and the aqueous mixture was extracted with 3×100 mL ethyl acetate. The combined ethyl acetate solutions were washed sequentially with 100 mL water and 100 mL brine, dried over anhydrous sodium sulfate, filtered and concentrated in vacuo. The residue (5.15 g) was chromatographed on 500 g silica gel, eluting with 9:1 hexane/ethyl acetate to yield 4.54 g (81 % yield) of the title compound as a white solid.

$^1$H NMR (CDCl$_3$) δ 1.11 (s, 9H); 1.43 (s, 9H); 2.41 (q, 1H); 3.08 (q, 1H); 3.41 (d, 1H); 3.8 (q, 1H); 4.49 (d, 1H); 6.62 (s, 1H); 6.79 (d, 1H); 7.3–7.64 (c, 5H); 7.92 (d, 1H); 8.0 (d, 1H).

EXAMPLE 20C1

7-Chloro-5-(1-naphthyl)-1-neopentyl-2-oxo-1,2,3,5-tetrahydro-4,1-benzothiazepin-3-acetic acid (mixture of diastereomers)

A stirred mixture of 50.0 g (141 mmol) of (5-chloro-2-neopentylamino-phenyl)-naphthalen-1-yl-methanol, 27.58 g (184 mmol, 1.3 equivalents) of mercaptosuccinic acid, and 340 mL of propionic acid was heated to 130° C. with a nitrogen purge. After 48 hours, the reaction mixture was cooled to room temperature giving a precipitate, treated with 200 mL of water, cooled to –5° C. with stirring, and filtered giving 60.83 g (92% yield) of the title compound as an off white solid.

The $^1$H NMR (CDCl$_3$) indicates three compounds in a 2:2:1 ratio, characteristic sets of peaks: 6.64 (s), 3.81 (dd), 1.11 (s); 6.73 (s), 4.16 (dd), 1.13 (s); 5.69 (s), 3.59 (dd), 0.63 (s).

EXAMPLE 20D

Trans-7-chloro-5-(1-naphthyl)-1-neopentyl-2-oxo-1,2,3,5-tetrahydro-4,1-benzothiazepin-3-acetic acid Trifluoroacetic acid (38 ml) was added slowly at room temperature to a stirred solution of 4.5 g of the t-butyl ester of trans-7-chloro-5-(1-naphthyl)-1-neopentyl-2-oxo-1,2,3,5-tetrahydro-4,1-benzothiazepin-3-acetic acid in 38 mL dichloromethane. The resulting solution was stirred at room temperature for 3 hours, then concentrated in vacuo. The residue was triturated with diethyl ether and the solid was filtered to yield 2.11 g of the title compound as a white solid. The filtrate was concentrated in vacuo and residue was triturated with diethyl ether and filtered to yield a further 1.05 g of the title compound (86% total yield).

$^1$H NMR (CDCl$_3$) δ 1.12 (s, 9H); 2.62 (q, 1H); 3.19 (q, 1H); 3.43 (d, 1H); 3.83 (q, 1H); 4.48 (d, 1H); 6.64 (s, 1H); 6.8 (d, 1H); 7.3–7.64 (c, 5H); 7.94 (d, 3H); 8.0 (d, 1H).

EXAMPLE 20D1

Trans-7-chloro-5-(1-naphthyl)-1-neopentyl-2-oxo-1,2,3,5-tetrahydro-4,1-benzothiazepin-3-acetic acid A solution of 30.0 g (64.1 mmol) of 7-chloro-5-(1-naphthyl)-1-neopentyl-2-oxo-1,2,3,5-tetrahydrom4,1-benzothiazepin-3-acetic acid (mixture of diastereomers) in 120 mL of dry tetrahydrofuran was treated with 22.0 mL of 25% sodium methoxide solution in methanol (96 mmol, 1.5 equivalents). The reaction mixture was warmed to 40° C. for 6 hours, cooled to room temperature, treated with 144 mL of 1N hydrochloric acid followed by 350 mL of water, stirred overnight at room temperature, and filtered giving 29.10 g (97% yield) of the title compound as a pale peach-colored granular solid. 1 H NMR identical to that of Example 20D.

EXAMPLE 21

Methyl ester of (–)-(S)-O-[trans-7-chloro-5-(1-naphthyl)-1-neopentyl-2-oxo-1,2,3,5-tetrahydro-4,1-benzothiazepin-3-acetyl]lactic acid and methyl ester of (+)-(S)-O-[trans-7-chloro-5-(1-naphthyl)-1-neopentyl-2-oxo-1,2,3,5-tetrahydro-4,1-benzothiazerin-3-acetyl]lactic acid To a solution of 1.5 g (3.2 mmol) trans-7-chloro-5-(1-naphthyl)-1-neopentyl-2-oxo-1,2,3,5-tetrahydro-4,1-benzothiazepin-3-acetic acid and 0.61 mL (6.4 mmol) (S)-methyl lactate in 30 mL dichloromethane cooled to 0° C. under nitrogen was added 1.1 g 1-ethyl-3-(3-dimethylaminopropyl)carbodiimide hydrochloride (5.8 mmol) and 45 mg 4-dimethylaminopyridine. The reaction mixture was stirred at room temperature for 3.5 hours, then diluted with 80 mL dichloromethane. The resulting solution was washed sequentially with 70 mL 1N aqueous hydrochloric acid, 70 mL saturated aqueous sodium bicarbonate solution and 70 mL brine, dried over anhydrous sodium sulfate, filtered and concentrated in vacuo. Flash chromatography of the residue (1.63 g) on 600 g silica gel, eluting with 3:1 hexane/ethyl acetate, yielded 716 mg of the less polar diastereomer, 72 mg of the more polar diastereomer and 739 mg of a mixture of the two diastereomers (86% total yield).

EXAMPLE 21A

Methyl ester of (–)-(S)-O-[trans-7-chloro-5-(1-naphthyl)-1-neopentyl-2-oxo-1,2,3,5-tetrahydro-4,1-benzothiazepin-3-acetyl]lactic acid (less polar diastereomer)

$^1$H NMR (CDCl$_3$) δ 1.10 (s, 9H); 1.49 (d, 3H); 2.60 (q, 1H); 3.25 (q, 1H); 3.40 (d, 1H); 3.72 (s, 3); 3.87 (q, 1H); 4.47 (d, 1H); 5.08 (q, 1H); 6.64 (s, 1H); 6.79 (d, 1H); 7.28 (m, 1H); 7.35–7.45 (m 3H); 7.50 (t, 1H); 7.61 (t, 1H); 7.93 (d, 2H); 7.99 (t, 1H).

$[\alpha]_D^{20}$ –261° (methanol)

EXAMPLE 21B

Methyl ester of (+)-(S)-O-[trans-7-chloro-5-(1-naphthyl)-1-neopentyl-2-oxo-1,2,3,5-tetrahydro-4,1-benzothiazepin-3-acetyl]lactic acid (more polar diastereomer)

$^1$H NMR (CDCl$_3$) δ 1.11 (s, 9H); 1.47 (d, 3H); 2.59 (q, 1H); 3.27 (q, 1H); 3.41 (d, 1H); 3.75 (s, 3H); 3.87 (q, 1H); 4.48 (d, 1H); 5.10 (q, 1H); 6.65 (s, 1H); 6.79 (d, 1H); 7.26–7.45 (m, 4H); 7.50 (t, 1H); 7.60 (t, 1H); 7.92 (d, 2H); 7.99 (t, 1H).

$[\alpha]_D^{20}$ +202° (methanol)

EXAMPLE 21C

Methyl ester of (–)-(S)-O-[trans-7-trifluoromethyl-5-(1-naphthyl)-1-neopentyl-2-oxo-1,2,3,5tetrahydro-4,1-benzoxazepin-3-acetyl]lactic acid A procedure similar to that described in Example 21 was used.

Less polar (–)-diastereomer

29% yield.

$^1$H NMR (250 MHz, CDCl$_3$) δ 1.05 (s, 9H); 1.5 (d, 3H); 2.98 (q, 1H); 3.26 (q, 1H); 3.57 (d, 1H); 3.71 (s, 3H); 4.54 (q, 1H); 4.59 (d, 1H); 5.09 (q, 1H); 6.67 (s, 1H); 6.82 (s, 1H); 7.73 (t, 1H); 7.44 (2d, 2H); 7.62 (m, 3H); 7.91 (t, 3H).

More polar (+)-diastereomer

23% yield.

$^1$H NMR (250 MHz, CDCl$_3$) δ 1.04 (s, 9H): 1.45 (d, 3H); 2.99 (q, 1H); 3.14 (q, 1H); 3.57 (d, 1H); 3.72 (s, 3H); 4.55 (t, 1H); 4.6 (d, 1H); 5.11 (q, 1H); 6.68 (s, 1H); 6.82 (s, 1H); 7.3 ((t, 1H); 7.46 (m, 2H); 7.6 (m, 3H); 7.84 (d, 1H); 7.92 (d, 2H).

EXAMPLE 22

(–)-Trans-7-chloro-5-(1-naphthyl)-1-neopentyi-2-oxo-1,2,3,5-tetrahydro-4,1-benzothiazepin-3-acetic acid A solution of 269 mg(1.95 mmol) potassium carbonate in 8 mL water was added to a solution of 360 mg (0.65 mmol)

methyl ester of (−)-(S)-O-[trans-7-chloro-5-(1-naphthyl)-1-neopentyl-2-oxo-1,2,3,5-tetrahydro-4,1-benzothiazepin-3-acetyl]lactic acid (less polar diastereomer) in 25 mL methanol. The resulting solution was heated at 60° C. for 2 hours, cooled to room temperature and then concentrated in vacuo. Water (10 ml) was added to the residue, the resulting solution was acidified with 1N aqueous hydrochloric acid and extracted with 3×30 mL ethyl acetate. The combined ethyl acetate extracts were washed with 70 mL brine, dried over anhydrous sodium sulfate, filtered and concentrated in vacuo to yield 290 mg (95% yield) of the title compound as a white solid.

$^1$H NMR (CDCl$_3$) δ 1.12 (s, 9H); 2.57 (q, 1H); 3.18 (q, 1H); 3.42 (d, 1H); 3.82 (q, 1H); 4.50 (d, 1H); 6.64 (s, 1H); 6.80 (d, 1H); 7.26–7.45 (m, 3H); 7.51 (t, 1H); 7.61 (t, 1H); 7.93 (d, 3H); 7.99 (t, 1H).

$[α]_D^{20}$ −288° (methanol)

EXAMPLE 22A (R)-α-Methylbenzylammonium salt of (−)-trans-7-chloro-5-(1-naphthyl)-1-neopentyl-2-oxo-1,2,3,5-tetrahydro-4,1-benzothiazepin-3-acetic acid A mixture of 10.0 g (21.4 mmol) of trans-7-chloro-5-(1-naphthyl)-1-neopentyl-2-oxo-1,2,3,5-tetrahydro-4,1-benzothiazepin-3-acetic acid, 224 mL of 95% ethanol, and 2.8 mL (21 mmol) of (R)-(+)-α-methylbenzylamine was heated to reflux and cooled with seeding of the title compound. The resulting slurry was stirred overnight at room temperature. The solids were isolated and dissolved in 60 mL of 95% ethanol at reflux, stirred at reflux temperature for 5 minutes, and slowly cooled to room temperature with stirring overnight. Filtration of the white solid and vacuum drying yielded 3.98 g (29% yield) of the title compound as an ethanol solvate with a diastereomeric purity 99.8% according to chiral chromatography.

$[α]_D$ −217.3° (c 1.0, CHCl$_3$).

$^1$H NMR (CDCl$_3$) δ 8.03–7.90 (m, 4H), 7.61–7.23 (m, 10H), 6.79 (d, 1H), 6.62 (s, 1H), 5.00 (br s, 4H), 4.40 (d, 1H), 4.22 (q, 1H), 3.78 (dd, 1H), 3.73 (q, 2H), 2.90 (dd, 1H), 2.32 (dd, 1H), 1.53 (d, 3H), 1.25 (t, 3H), 1.08 (s, 9H).

EXAMPLE 22B (−)-Trans-7-chloro-5-(1-naphthyl)-1-neopentyl-2-oxo-1,2,3,5-tetrahydro-4,1-benzothiazepin-3-acetic acid The (R)-α-methylbenzylammonium salt of (−)-trans-7-chloro-5-(1-naphthyl)-1-neopentyl-2-oxo-1,2,3,5-tetrahydro-4,1-benzothiazepin-3-acetic acid, ethanol solvate, 3.50 g (5.51 mmol), was treated with 35 mL of ethyl acetate and 17 mL of 1N hydrochloric acid with stirring at room temperature giving two homogeneous phases. The phases were separated, the aqueous phase was extracted with ethyl acetate (2×15 mL), and the combined organic phases were concentrated under vacuum giving 2.48 g (96% yield) of the title compound as a white solid.

$^1$H NMR identical to that of Example 22.

EXAMPLE 22C (−)-Trans-7-trifluoromethyl-5-(1-naphthyl)-1-neopentyl-2-oxo-1,2,3,5-tetrahydro-4,1-benzoxazepin-3-acetic acid A procedure similar to that described in Example 22 was used using the less polar (−)-diastereomer of Example 21C. 60% yield.

$^1$H NMR (250 MHz, CDCl$_3$) identical to that of Example 54D.

$[α]_D^{20}$ −151° (c 1.0,methanol).

EXAMPLE 23

(+)-Trans-7-chloro-5-(1-naphthyl)-1-neopentyl-2-oxo-1,2,3,5-tetrahydro-4,1-benzothiazepin-3-acetic acid Using a procedure analogous to that described in Example 22 but starting with the methyl ester of (S)-O-[(+)-trans-7-chloro-5-(1-naphthyl)-1-neopentyl-2-oxo-1,2,3,5-tetrahydro-4,1-benzothiazepin-3-acetyl]lactic acid (more polar diastereomer), the title compound was obtained as a white solid in quantitative yield.

$^1$H NMR (CDCl$_3$) δ 1.12 (s, 9H); 2.57 (q, 1H); 3.19 (q, 1H); 3.42 (d, lh); 3.82 (q, 1H); 4.50 (d, 1H); 6.64 (s, 1H); 6.80 (d, 1H); 7.26–7.46 (c, 3H); 7.51 (t, 1H); 7.61 (t, 1H); 7.93 (d, 3H); 7.99 (t, 1H).

$[α]_D^{20}$ +264° (methanol)

The title compounds of Examples 23A through 23C were prepared by a procedure analogous to that described in Example 20A–20C.

EXAMPLE 23A t-Butyl ester of trans-7-methyl-5-(naphthalen-1-yl)-1-neopentyl-1,2,3,5-tetrahydro-2-oxo-4,1-benzothiazepine-3-acetic acid 95% yield.

MS (PCl): 505 (M+2H$^+$).

$^1$H NMR (250 MHz, CDCl$_3$) δ 8.00 (m, 2H), 7.90 (m, 2H), 7.61–7.28 (m, 4H), 7.10 (dd, 1H), 6.64 (s, 1H), 6.59 (d, 1H), 4.47 (d, 1H), 3.80 (dd, 1H), 3.44 (d, 1H), 3.07 (dd, 1H), 2.39 (dd, 1H), 2.09 (s, 3H), 1.42 (s, 9H), 1.10 (s, 9H).

EXAMPLE 23B t-Butyl ester of trans-7-methoxy-5-(naphthalen-1-yl)-1-neopentyl-1,2,3,5-tetrahydro-2-oxo-4,1-benzothiazepine-3-acetic acid 82% yield.

MS (PCl): 521 (M+2H$^+$).

$^1$H NMR (300 MHz, CDCl$_3$) δ 8.00 (m, 2H), 7.88 (dd, 2H), 7.59–7.32 (m, 4H), 6.82 (dd, 1H), 6.63 (s, 1H), 6.34 (d, 1H), 4.46 (d, 1H), 3.84 (dd, 1H), 3.54 (s, 3H), 3.40 (d, 1H), 3.07 (dd, 1H), 2.39 (dd, 1H), 1.42 (s, 9H), 1.11 (s, 9H).

EXAMPLE 23C t-Butyl ester of trans-7-chloro-5-(4-methoxyrarphthalen-1-yl)-1-neopentyl-1,2,3,5-tetrahydro-2-oxo-4,1-benzothiazepine-3-acetic acid 34% yield.

MS (PCl): 555 (M+2H$^+$).

$^1$H NMR (250 MHz, CDCl$_3$) δ 8.35 (d, $_1$H), 7.88 (m, 2H), 7.51–7.25 (m, 4H), 6.91 (d, 1-H), 6.82 (d, 1H), 6.53 (s,1H), 4.48 (d, 1H), 4.07 (s, 3H), 3.76 (dd,1H), 3.39(d, 1H), 3.07 (dd, 1H), 2.39 (dd, 1H), 1.42 (s, 9H), 1.10 (s, 9H).

EXAMPLE 23D

Ethyl ester of trans-7-acetyl-5-(naphthalen-1-yl)-1-neopentyl-1,2,3,5-tetrahydro-2-oxo-4,1-benzothiazepine-3-acetic acid Trans-7-bromo-5-(naphthalen-1-yl)-1-neopentyl-1,2,3,5-tetrahydro-2-oxo-4,1-benzothiazepine-3-acetic acid (Example 23I; 3.19 g, 6.23 mmol), concentrated sulfuric acid (10 drops) and ethanol (53 mL) were heated at reflux for 18 h, cooled to ambient temperature and concentrated under reduced pressure. The resulting oil was diluted with ethyl acetate, washed with saturated aqueous sodium bicarbonate and saturated aqueous sodium chloride, dried over anhydrous sodium sulfate and concentrated under reduced pressure to provide the ethyl ester of trans-7-bromo-5-(naphthalen-1-yl)-1-neopentyl-1,2,3,5-tetrahydro-2-oxo-4,1-benzothiazepine-3-acetic acid as a white foam in quantitative yield. The ethyl ester of trans-7-bromo-5-(naphthalen-1-yl)-1-neopentyl-1,2,3,5-tetrahydro-2-oxo-4,1-benzothiazepine-3-acetic acid (1.00 g) was converted to the title compound in a manner similar to that described in Example 6F to provide 406 mg (44%) of the title compound as a white powder.

MS (PCl): 504 (M+H$^+$).

EXAMPLE 23D1

Ethyl ester of trans-7-(thiazol-2-yl)-5-(naphthalen-1-yl)-1-neopentyl-1,2,3,5-tetrahydro-2-oxo-4,1-benzothiazepine-3-acetic acid A mixture of the ethyl ester of trans-7-bromo-5-(naphthalen-1-yl)-1-neopentyl-1,2,3,5-tetrahydro-2-oxo-4,1-benzothiazepine-3-acetic acid (200 mg, 370 μmol), 2-tributylstannylthiazole (253 mg, 407 μmol; 60% pure), bis(triphenylphosphine)palladium (II) chloride (2.6 mg, 3.7μmol) and toluene (450 μL) was heated at 100° C. for 20 hours. Rection mixture cooled to ambient temperature, absorbed onto silica gel and purified by flash column chromatography (4:1 hexanes/ethyl acetate) to provide 97 mg (48%) the title compound as a white foam that was triturated with hexanes.

MS (PCl): 545 (M+H$^+$).

$^1$H NMR (300 MHz, CDCl$_3$) δ 8.10–7.89 (m, 5H), 7.72 (d, 1H), 7.64 (t, 1H), 7.52–7.37 (m, 4H), 7.19 (d, 1H), 6.72 (s, 1H), 4.52 (d, 1H), 4.12 (qd, 2H), 3.92 (dd, 1H), 3.49 (d, 1H), 3.18 (dd, 1H), 2.48 (dd, 1H), 1.24 (t, 3H), 1.12 (s, 9H).

The title compounds of Examples 23E through 23H1 were prepared by a procedure analogous to that described in Example 20D.

EXAMPLE 23E

Trans-7-methyl-5-(naphthalen-1-yl)-1-neopentyl-1,2,3,5-tetrahydro-2-oxo-4,1-benzothiazepine-3-acetic acid 81% yield.

MS (PCl): 448 (M+H$^+$).

$^1$H NMR (250 MHz, CDCl$_3$) δ 11.90 (br s, 1H), 7.96 (m, 4H), 7.63–7.26 (m, 4H), 7.15 (dd,1H), 6.64 (d, 2H), 4.47 (d,1H), 3.86 (dd,1H), 3.48 (d,1H), 3.20 (dd,1H), 2.64 (dd, 1H), 2.12 (s, 3H), 1.12 (s, 9H).

EXAMPLE 23F

Trans-7-methoxy-5-(naphthalen-1-yl)-1-neopentyl-1,2,3,5-tetrahydro-2-oxo-4,1-benzothiazepine-3-acetic acid 88% yield.

MS (PCl): 464 (M+H$^+$).

$^1$H NMR (300 MHz, CDCl$_3$) δ 8.00 (d, 2H), 7.89 (d, 2H), 7.60–7.30 (m, 4H), 6.84 (dd, 1H), 6.64 (s, 1H), 6.35 (d, 1H), 4.47 (d, 1H), 3.85 (dd, 1H), 3.55 (s, 3H), 3.40 (d, 1H), 3.13 (dd, 1H), 2.59 (dd, 1H), 1.11 (s, 9H).

EXAMPLE 23G

Trans-7-chloro-5-(4-methoxynaphthalen-1-yl)-1-neopentyl-1,2,3,5-tetrahydro-2-oxo-4,1-benzothiazepine-3-acetic acid 92% yield.

MS (PCl): 498 (M+H$^+$).

$^1$H NMR (250 MHz, CD$_3$OD) δ 12.44 (br s, 1H), 8.28 (d, 1H), 7.79 (m, 3H), 7.51 (m, 3H), 7.15 (d, 1H), 6.64 (d, 1H), 6.39 (s, 1H), 4.26 (d, 1H), 4.04 (s, 3H), 3.62 (m, 2H), 2.83 (dd, 1H), 2.50 (m, 1H), 1.01 (s, 9H).

EXAMPLE 23H

Trans-7-acetyl-5-(naphthalen-1-yl)-1-neopentyl-1,2,3,5-tetrahydro-2-oxo-4,1-benzothiazepine-3-acetic acid 77% yield.

MS (PCl): 476 (M+H$^+$).

$^1$H NMR (300 MHz, CDCl$_3$) δ 8.04 (d, 1H). 7.94 (m, 4H), 7.65–7.39 (m, 5H), 6.70 (s, 1H), 4.53 (d, 1H), 3.79 (dd, 1H), 3.49 (d, 1H), 3.19 (dd, 1H), 2.57 (dd, 1H), 2.28 (s, 3H), 1.11 (s, 9H).

EXAMPLE 23H1

Trans-7-(thiazol-2-yl)-5-(naphthalen-1-yl)-1-neopentyl-1,2,3,5-tetrahydro-2-oxo-4,1-benzothiazepine-3-acetic acid 47% yield.

MS (PCl): 517 (M+H$^+$).

$^1$H NMR (300 MHz, CD$_3$OD) δ 8.08 (d, 1H), 7.96 (m, 3H), 7.88 (s, 3H), 7.66 (m, 2H), 7.44 (m, 3H), 6.67 (s, 1H), 4.43 (d, 1H), 3.87 (dd, 1H),.3.63 (d, 1H), 3.00 (dd, 1H), 2.51 (dd, 1H), 1.11 (s, 9H).

EXAMPLE 23I

Trans-7-bromo-5-(naphthalen-1-yl)-1-neopentyl-1,2,3,5-tetrahydro-2-oxo-4,1-benzothiazepine-3-acetic acid Prepared in a manner similar to that described in Example 20C1, with the addition of the mercaptosuccinic acid taking place in glacial acetic acid followed by concomitant cyclization and epimerization in chlorobenzene in the presence of catalytic p-toluenesulfonic acid and 3 Å seives.

20% yield.

MS (PCl): 514 (M+H$^+$).

$^1$H NMR (250 MHz, CDCl$_3$) δ 7.96 (m, 4H), 7.63–7.28 (m, 5H), 6.95 (d, 1H), 6.63 (s, 1H), 4.48 (d, 1H), 3.81 (dd, 1H), 3.41 (d, 1H), 3.15 (dd, 1H), 2.59 (dd, 1H), 1.11 (s, 9H).

EXAMPLE 24

Methyl ester of N-[trans-7-chloro-5-(1-naphthyl)-1-neopentyl-2-oxo-1,2,3,5-tetrahydro-4,1-benzoxazepin-3-acetyl]-L-proline To a solution of 208 mg (0.46 mmol) trans-7-chloro-5-(1-naphthyl)-1-neopentyl-2-oxo-1,2,3,5-tetrahydro-4,1-benzoxazepin-3-acetic acid and 80 mg (0.48 mmol) L-proline methyl ester hydrochloride in 5 mL dimethylformamide cooled to 0° C. was added 0.08 mL (0.52 mmol) diethyl cyanophosphonate followed by 0.13 mL (0.92 mmol) triethylamine. The reaction mixture was stirred at room temperature for 2 hours, then poured into 50 mL ice water. The resulting mixture was extracted with 3×40 mL ethyl acetate and the combined ethyl acetate extracts were washed sequentially with 50 mL 1N aqueous hydrochloric acid, 50 mL saturated sodium bicarbonate, 3×50 mL water and 50 mL brine. The ethyl acetate solution was dried over anhydrous sodium sulfate, filtered and concentrated in vacuo. The resulting oil was chromatographed- on 200 g silica gel, eluting with 1:1 hexane/ethyl acetate to yield 220 mg (85% yield) of the title compound as a white amorphous solid.

$^1$H NMR (CDCl$_3$): δ 1.03, 1.04 (2s, 9H); 1.8–2.34 (c, 3H); 2.75–3.3 (c, 3H); 3.42–3.78 [c, d at 3.47(1H) and 2s at 3.7, 3.73 (3H), total 6H]; 4.43–4.61 (c, 2H); 4.73 (c, 1H); 6.51 (2d, 1H); 6.6, 6.62 (2s, 1H); 7.28–7.64 (c, 6H); 7.7–7.96 (c and d at 9.91, total 3H).

The title compounds of Examples 24A through 31N were prepared by a procedure analogous to that described in Example 24.

EXAMPLE 24A

Methyl ester of (−)-N-[trans-7-chloro-5-(1-naphthyl)-1-neopentyl-2-oxo-1,2,3,5-tetrahydro-4,1-benzoxazepin-3-acetyl]-L-proline Using the procedure of Example 24 but starting with (−)-trans-7-chloro-5-(1-naphthyl)-1-neopentyl-2-oxo-1,2,3,5-tetrahydro-4,1-benzoxazepin-3-acetic acid (Example 18), the title compound was obtained as a white solid in 59% yield.

$^1$H NMR (CDCl$_3$): δ 1.03 (s, 9H); 1.93–2.26 (c, 3H); 2.82 (q, 1H); 3.23 (q, 1H); 3.47 (d, 1H); 3.7 (c and s, 5H); 4.47 (m, 2H); 4.54 (d, 1H); 4.72 (m, 1H); 6.52 (d, 1H); 6.61 (s, 1H); 7.3–7.56 (c, 5H); 7.61 (t, 1H); 7.92 (d, 3H).

$[\alpha]_D^{20}$ −199° (methanol)

EXAMPLE 25

Ethyl ester of N-[trans-7-chloro-5-(1-naphthyl)-1-neopentyl-2-oxo-1,2,3,5-tetrahydro-4,1-benzoxazepin-3-acetyl]isonipecotic acid 77% yield $^1$H NMR (CDCl$_3$): δ 1.04 (s, 9H); 1.26 (c, 3H); 1.55–2.0 (c, 3H); 2.5 (c, 1H); 2.83 (c, 2H); 3.15 (c, 2H); 3.49 (d, 1H); 3.92 (c, 1H); 4.13 (c, 2H); 4.35 (c, 1H); 4.58 (2d, 1H); 4.7 (c, 1H); 6.52 (s, 1H); 6.61 (s, 1H); 7.3–7.62 (c, 6H); 7.84 (m, 1H); 7.91 (d, 2H).

EXAMPLE 25A

Ethyl ester of (−)-N-[trans-7-chloro-5-(1-naphthyl)-1-neopentyl-2-oxo-1,2,3,5-tetrahydro-4,1-benzoxazepin-3-acetyl]isonipecotic acid Using a procedure analogous to that of Example 24A, the title compound was obtained as a white solid in 73% yield.

$^1$H NMR identical to that of Example 25.

EXAMPLE 26

Ethyl ester of N-[trans-7-chloro-5-(1-naphthyl)-1-neopentyl-2-oxo-1,2,3,5-tetrahydro-4,1-benzoxazepin-3-acetyl]nipecotic acid 77% yield $^1$H NMR (CDCl$_3$); δ 1.04 (s, 9H); 1.25 (c, 3H); 1.55–1.85 (c, 3H); 2.06 (c, 1H); 2.3–3.45 (c, 6H); 3.5 (d, 1H); 3.95 (c, 1H); 4.13 (q, 2H), 4.57 (d, 1H); 4.7 (c, 1H); 6.52 (s, 1H), 6.62 (s, 1H); 7.3–7.62 (c, 6H); 7.84 (b, 1H); 7.92 (d, 2H).

EXAMPLE 27

Methyl ester of N-[trans-7-chloro-5-(1-naphthyl)-1-neoentyl-2-oxo-1,2,3,5-tetrahydro-4,1-benzoxazepin-3-acetyl]-L-S-methylcysteine 58% yield Flash chromatography of 223 mg of the crude product on 50 g silica gel, eluting with 6:4 hexane/ethyl acetate, yielded 67.2 mg of the less polar diastereomer, 46.2 mg of the more polar diastereomer and 33.3 mg of a mixture of the two diastereomers.

Less polar diastereomer $^1$H NMR (CDCl$_3$): δ 1.04 (s, 9H); 2.06 (d, 3H), 2.77–3.07 (m, 4H); 3.47 (d, 1H); 3.72 (s, 3H); 4.51, 4.53, 4.55, 4.58 (2d, 2H); 4.8 (c, 1H); 6.53 (d, 1H); 6.64 (s, 1H); 6.73 (d, 1H); 7.33 (c, 3H); 7.47 (c, 2H); 7.6 (t, 1H); 7.9 (t, 3H).

More polar diastereomer $^1$H NMR (CDCl$_3$): δ 1.04 (s, 9H); 1.97 (s, 3H); 2.77–3.04 (c and d at 2.9, total 4H); 3.48 (d, 1H); 3.76 (s, 3H); 4.58 (c, 2H); 4.81 (c, 1H); 6.53 (d, 1H); 6.63 (s, 1H); 6.77 (d, 1H); 7.36 (c, 3H); 7.42–7.62 (m, 3H); 7.86 (d, 1H); 7.91 (d, 2H).

EXAMPLE 27A

Methyl ester of (−)-N-[trans-7-chloro-5-(1-naphthyl)-1-neopentyl-2-oxo-1,2,3,5-tetrahydro-4,1-benzoxazepin-3-acetyl]-L-S-methylcysteine Using a procedure analogous to Example 24A the title compound was obtained as a white solid in 68% yield.

$^1$H NMR identical to that of less polar diastereomer in Example 27.

$[\alpha]_D^{20}$ −190° (methanol).

EXAMPLE 28

α,β-Dimethyl ester of N-[trans-7-chloro-5-(1-naphthyl)-1-neopentyl-2-oxo-1,2,3,5etrahydro-4,1-benzoxazepin-3-acetyl]-L-aspartic acid 59% yield $^1$H NMR (CDCO$_3$) δ 1.03, 1.04 (2s, 9H); 2.8 (c, 2H); 2.89–3.08 (c, 2H); 3.47 (d, 1H); 3.58, 3.67, 3.69, 3.75 (4s, 6H); 4.56 (c, 2H); 4.86 (c, 1H); 6.52 (s, 1H); 6.62 (s, 1H); 6.83 (m, 1H); 7.35 (c, 3H); 7.47 (m, 2H); 7.6 (c, 1H); 7.85 (m, 1H); 7.91 (d, 2H).

EXAMPLE 29

α,γ-Dimethyl ester of N-[trans-7-chloro-5-(1-naphthyl)-1-neopentyl-2-oxo-1,2,3,5-tetrahydro-4,1-benzoxazepin-3-acetyl]-L-glutamic acid 52% yield $^1$H NMR (CDCl$_3$) δ 1.03 (s, 9H); 1.99 (m, 1H); 2.1–2.45 (c, 3H); 2.77 (q,1H); 2.94 (q, 1H); 3.47 (d, 1H); 3.57, 3.66, 3.69, 3.73 (4s, 6H); 4.58 (c, 3H); 6.51 (d, 1H); 6.52, 6.62 (2d, total 1H); 6.61 (s, 1H); 7.35 (c, 3H); 7.47 (m, 2H); 7.58 (t, 1H); 7.84 (t, 1H); 7.91 (d, 2H).

EXAMPLE 30

β-t-Butyl ester-α-methyl ester of N-[trans-7-chloro-5-(1-naphthyl)-1-neopentyl-2-oxo-1,2,3,5-tetrahydro-4,1-benzoxazepin-3-acetyl]-L-aspartic acid 71% yield Column chromatography of 210 mg of crude product on 200 g silica gel, eluting with 7:3 hexane/ethyl acetate, yielded 41 mg of the less polar diastereomer, 33 mg of the more polar diastereomer and 69 mg of a mixture of the two diastereomers.

EXAMPLE 30A

Less polar diastereomer $^1$H NMR (CDCl$_3$): δ 1.03 (s, 9H); 1.42 (s, 9H); 2.66–3.0 (c, 4H); 3.47 (d, 1H); 3.69 (s, 3H); 4.55 (c, 2H); 4.85 (c, 1H); 6.51 (d, 1H); 6.62 (s, 1H); 6.78 (d, 1H); 7.25–7.5 (c, 6H); 7.59 (t, 1H); 7.9 (c, 3H).

EXAMPLE 30B

More polar diastereomer $^1$H NMR (CDCl$_3$): δ 1.04 (s, 9H); 1.36 (s, 9H); 2.62–3.0 (m, 4H); 3.47 (d, 1H); 3.74 (s, 3H); 4.58 (c, 2H); 4.82 (c, 1H); 6.51 (d, 1H); 6.62 (s, 1H); 6.80 (d, 1H); 7.35 (m, 4H); 7.48 (q, 1H); 7.59 (t, 1H); 7.83 (d, 1H); 7.91 (d, 2H).

EXAMPLE 31

γ-t-Butyl ester-α-methyl ester of N-[trans-7-chloro-5-(1-naphthyl)-1-neopentyl-2-oxo-1,2,3,5-tetrahydro-4,1-benzoxazepin-3-acetyl]-L-glutamic acid 80% yield Column chromatography of 220 mg of crude product on 200 g silica gel, eluting with 7:3 hexane/ethyl acetate, yielded 97 mg of the less polar diastereomer, 70 mg of the more polar diastereomer and 12 mg of a mixture of the two diastereomers.

EXAMPLE 31A

Less polar diastereomer $^1$H NMR (CDCl$_3$): δ 1.04 (s, 9H); 1.44 (s, 9H); 1.95 (m, 1H); 2.18 (m, 1H); 2.3 (m, 2H); 2.77 (q, 1H); 2.94 (q, 1H); 3.47 (d, 1H); 3.69 (s, 3H); 4.57 (c, 3H); 6.51 (s, 1H); 6.54 (d, 1H); 6.61 (s, 1H); 7.29–7.51 (c, 5H); 7.59 (t, 1H); 7.86 (d, 1H); 7.91 (d, 2H).

EXAMPLE 31B

More polar diastereomer:

$^1$H NMR (CDCl$_3$): δ 1.04 (s, 9H); 1.39 (s, 9H); 1.94 (m, 1H); 2.11 (m, 1H); 2.27 (m, 2H); 2.76 (q, 1H); 2.95 (q, 1H); 3.47 (d, 1H); 3.73 (s, 3H); 4.56 (c, 3H); 6.52 (s, 1H); 6.58 (d, 1H); 6.62 (s, 1H); 7.35 (c, 3H); 7.48 (q, 2H); 7.6 (t, 1H); 7.84 (d, 1H); 7.91 (d, 2H).

EXAMPLE 31C

Methyl ester of N-[trans-7-chloro-5-(1-naphthyl)-1-neopentyl-2-oxo-1,2,3,5-tetrahydro-4,1-benzoxazepin-3-acetyl]-1-amino-1-cyclopentanecarboxylic acid 64% yield $^1$H NMR (250 MHz, CDCl$_3$) δ 1.04 (s, 9H); 1.77 (c, 4H); 1.94 (c, 2H); 2.23 (c, 2H); 2.73 (q, 1H); 2.89 (q, 1H); 3.47 (d, 1H); 3.67 (s, 3H), 4.55 (c, 2H); 6.32 (s, 1H); 6.52 (d, 1H); 6.63 (s, 1H); 7.35 (m, 3H); 7.48 (q, 2H); 7.58 (t, 1H); 7.9 (t, 3H).

EXAMPLE 31D

Methyl ester of N-[trans-7-chloro-5-(1-naphthyl)-1-neopentyl-2-oxo-1,2,3,5-tetrahydro-4,1-benzoxazepin-3-acetyl]-1-amino-1-cyclopropanecarboxylic acid 51% yield.

$^1$H NMR (250 MHz, CDCl$_3$) δ 1.04 (s, 9H); 1.6 (c, 4H); 2.73 (q, 1H); 2.93 (q, 1H); 3.48 (d, 1H); 3.66 (s, 3H); 4.56 (d) and 4.58 (m) (total 2H); 6.4 (s, 1H); 6.53 (d, 1H); 6.62 (s, 1H); 7.35 (c, 3H); 7.5 (m, 2H); 7.6 (t, 1H); 7.87 (d, 1H); 7.92 (d, 2H).

EXAMPLE 31E

Ethyl ester of N-[(−)-trans-7-chloro-5-(1-naphthyl)-1-neopentyl-2-oxo-1,2,3,5-tetrahydro-4,1-benzoxazepin-3-acetyl]-L-methionine Less polar diastereomer 32% yield.

$^1$H NMR (250 MHz, CDCl$_3$) δ 1.04 (s, 9H); 1.27 (t, 3H); 1.98 (m, 1H); 2.1 (s) and 2.17 (m) (total 4H); 2.5 (c, 2H); 2.8 (q, 1H); 2.96 (q, 1H); 3.47 (d, 1H); 4.17 (q, 2H); 4.55 (c, 2H); 4.67 (m, 1H); 6.5 (d) and 6.52 (d) (total 2H); 6.62 (s, 1H); 7.3–7.4 (c, 3H); 7.42–7.51 (c, 2H); 7.59 (t, 1H); 7.86 (d, 1H); 7.91 (d, 2H).

EXAMPLE 31F

Methyl ester of N-[trans-7-chloro-5-(1-naphthyl)-1-neopentyl-2-oxo-1,2,3,5-tetrahydro-4,1-benzoxazepin-3-acetyl]-cis-4-hydroxy-D-proline 58% yield.

$^1$H NMR (250 MHz, CDCl$_3$) δ 1.03 (2s, 9H); 2.03–2.4 (c, 2H); 2.85 (q, 1H); 3.17 (q, 1H); 3.46 (d, 1H); 3.65–3.88 (c and 2S at 3.78, 3.79, total 5H); 4.22 (c, 1H); 4.46–4.6 (c, 2H); 4.7 (c, 1H); 6.53 (d, 1H); 6.61 (s, 1H); 7.3–7.65 (c, 6H); 7.74 (d) and 7.9 (c) (total 3H).

EXAMPLE 31G

Methyl ester of N-[trans-7-chloro-5-(1-naphthyl)-1-neopentyl-2-oxo-1,2,3,5-tetrahydro-4,1-benzoxazepin-3-acetyl]trans 4-hydroxy-L-proline 44% yield.

$^1$H NMR (250 MHz, CDCl$_3$) δ 1.02, 1.03 (2s, 9H); 2.28(c, 2H); 2.54 (d, 1H); 2.77, 2.83 (2q, 1H); 3.0, 3.2 (2q, 1H); 3.45, 3.46 (2d, 2H); 3.73 (2s, 3H); 4.6 (c, 3H); 4.7 (c, 1H); 6.52 (s, 1H); 6.61 (s, 1H); 7.3–7.64 (c, 6H); 7.8–7.95 (m, 3H).

EXAMPLE 31H

Methyl ester of N-[trans-7-chloro-5-(1-naphthyl)-1-neopentyl-2-oxo-1,2,3,5-tetrahydro-4,1-benzoxazepin-3-acetyl]4-azetidinecarboxylic acid 25% yield.

$^1$H NMR (250 MHz, CDCl$_3$) δ 1.03 (2s, 9H); 2.6 (q, 1H); 2.68 (d, 1H); 2.8 (q, 1H); 3.47 (d, 1H); 3.71, 3.74 (2s, 3H); 4.17 (c, 2H); 4.35 (c, 2H); 4.47–4.65 (m, 2H); 6.51 (t, 1H); 6.61 (s, 1H); 7.36 (c, 3H); 7.4–7.67 (c, 3H); 7.81 (q; 1H); 7.92 (d, 2H);

EXAMPLE 31I

Methyl ester of (−)-N-[trans-7-chloro-5-(1-naphthyl)-1-neopentyl-2-oxo-1,2,3,5-tetrahydro-4,1-benzoxazepin-3-acetyl]-D-proline Using a procedure similar to that of Example 24A the title compound was obtained as a white solid in 44% yield.

$^1$H NMR (250 MHz, CDCl$_3$) δ 1.04 (s, 9H); 1.8–2.4 (C, 4H); 2.86–3.16 (c and q at 2.95, total 2H); 3.42–3.75 (c and s at 3.72, total 6H); 4.53 (c) and 4.58 (d) (total 2H); 4.72 (c, 1H); 6.5 (d, 1H); 6.62 (s, 1H); 7.28–7.64 (c, 6H); 7.77 (d, 1H); 7.91 (d, 2H).

$[\alpha]_D^{20}$ −135° (c 1.0, $CHCl_3$).

EXAMPLE 31J

Methyl ester of (−)-N-[trans-7-chloro-5-(1-naphthyl)-1-neopentyl-2-oxo-1,2,3,5-tetrahydro-4,1-benzoxazepin-3-acetyl]-L-pipecolinic acid Using a procedure similar to that of Example 24A the title compound was obtained as a white solid in 79% yield.

$^1$H NMR (250 MHz, $CDCl_3$) δ 1.04 (s, 9H); 1.5–1.78 (C, 5H); 2.2 (c, 1H); 2.83 (q, 1H); 3.22 (m, 1H); 3.36 (q, 1H); 3.5 (d, 1H); 3.7 (s, 3H); 3.87 (c, 1H); 4.58 (d, 1H); 4.68 (q, 1H); 5.26 (c, 1H); 6.51 (d, 1H); 6.62 (s, 1H); 7.3–7.64 (c, 6H); 7.92 (d, 3H).

EXAMPLE 31K

Ethyl ester of (−)-N-[trans-7-chloro-5-(1-naphthyl)-1-neopentyl-2-oxo-1,2,3,5-tetrahydro-4,1-benzoxazepin-3-acetyl]-(−)-nipecotic acid Using a procedure similar to that of Example 24A the title compound was obtained as a white solid in 69% yield.

$^1$H NMR (250 MHz, $CDCl_3$) identical to that of Example 26 except for the protons at 1.256 which are a quartet.

$[\alpha]_D^{20}$ −119.6° (c 0.7, MeOH).

EXAMPLE 31L

Ethyl ester of N-[trans-7-trifluoromethyl-5-(1-naphthyl)-1-neopentyl-2-oxo-1,2,3,5-tetrahydro-4,1-benzoxazepin-3-acetyl]nipecotic acid 76% yield.

$^1$H NMR (250 MHz, CDCl3) δ 1.04 (s, 9H); 1.25 (c, 3H); 1.5–1.85 (c, 3H); 2.05 (c, 1H); 2.4–3.5 (c, 6H); 3.58 (d, 1H); 3.82–4.2 (c and q at 4.13, total 3H); 4.65 (d, 1H); 4.68 (c, 1H); 6.66 (s, 1H); 6.82 (d, 1H); 7.32 (c, 1H); 7.46 (t, 2H); 7.6 (s and c, total 3H); 7.87 (t, 1H); 7.92 (d, 2H).

EXAMPLE 31M

Ethyl ester of N-[trans-7-trifluoromethyl-5-(1-naphthyl)-1-neopentyl-2-oxo-1,2,3,5-tetrahydro-4,1-benzoxazepin-3-acetyl]isonipecotic acid 67% yield.

$^1$H NMR (250 MHz, $CDCl_3$) δ 1.04 (s, 9H); 1.25 (c, 3H); 1.52–1.98 (c, 4H); 2.5 (c, 1H); 2.82 (c, 2H); 3.15 (c, 2H); 3.58 (d, 1H); 3.9 (c, 1H); 4.1 (c, 2H); 4.34 (c, 1H); 4.6 (2d, 1H); 4.67 (c, 1H); 6.66 (s, 1H); 6.82 (s, 1H); 7.32 (t, 1H); 7.48 (c, 2H); 7.6 (s and c, total 3H); 7.86 (t, 1H); 7.92 (d, 2H);

EXAMPLE 31N

Methyl ester of N-[trans-7-trifluoromethyl-5-(1-naphthyl)-1-neopentyl-2-oxo-1,2,3,5-tetrahydro-4,1-benzoxazepin-3-acetyl]-L-proline 76% yield.

$^1$H NMR (250 MHz, $CDCl_3$ δ 1.03, 1.04 (2s, 9H); 1.8–2.36 (c, 3H); 2.77–3.3 (c, 3H); 3.5–3.75 [c,d (1H) at 3.55 and 2 s (3H)at 3.69 and 3.72 (total 6H)]; 4.42–4.76 (c, 3H); 6.65 (s, 1H); 6.81 (d, 1H); 7.35 (m, 1H); 7.46 (m, 2H); 7.6 (c, 3H); 7.78–7.95 (c and d at 7.92, total 3H);

EXAMPLE 32

Ethyl ester of N-[trans-7-chloro-5-(naphthalen-1-yl)-1-neopentyl-1,2,3,5-tetrahydro-4,1-benzoxazepine-3-acetyl]isonipecotic acid 4-Dimethylaminopyridine (2.3 mg, 19 μmol), 1-(3-dimethylaminopropyl)-3-ethylcarbodiimide hydrochloride (72 mg, 374 μmol) and ethyl isonipecotate (35 mg, 225 μmol, 35 μL) were added sequentially to a solution of trans-7-chloro-5-(naphthalen-1-yl)-1-neopentyl-1,2,3,5-tetrahydro-4,1-benzoxazepine-3-acetic acid (84 mg, 187 μmol) and methylene chloride (3 mL). After stirring 18 hours at ambient temperature, the reaction mixture was diluted with ethyl acetate, washed with water and saturated aqueous sodium chloride, dried over anhydrous magnesium sulfate, filtered, concentrated under reduced pressure, and purified by flash column chromatography (2:1 hexanes/ethyl acetate) to produce 92 mg (84%) of the title compound as a white solid.

MS (PCl): 577.

$^1$H NMR (250 MHz, $CD_3OD$) δ 8.31 (d, 1H), 7.87 (s, 1H), 7.83 (dd, 1H), 7.57–7.25 (m, 4H), 6.97 (dd, 1H), 6.88 (d, 1H), 6.47 (s, 1H), 6.33 (d, 1H), 4.33 (br t, 1H), 4.03 (m, 2H), 3.57 (m, 2H), 3.52 (d, 1H), 3.06 (m, 1H), 2.89 (d, 1H), 2.52 (m, 2H), 2.26 (m, 2H), 1.99 (m, 1H), 1,83 (m, 1H), 1.57 (m, 1H), 1.46–0.83 (m, 3H), 1.18 (q, 3H), 1.08 (s, 9H).

The title compounds of Examples 32A through 32N were prepared by a procedure analogous to that described in Example 32.

EXAMPLE 32A

Ethyl ester of N-[trans-7-chloro-5-(4-methoxynaphthalen-1-yl)-1-neopentyl-1,2,3,5-tetrahydro-2-oxo-4,1-benzoxazepine-3-acetyl] isonipecotic acid 93% yield.

MS (PCl): 621.

$^1$H NMR (250 MHz, $CDCl_3$) δ 8.35 (d, $_1$H), 8.11 (t, $_1$H), 7.48–7.29 (m, 5H), 6.90 (t, 1H), 6.57 (t, 1H), 6.52 (s, 1H), 4.66 (m, 1H), 4.56 (app d, 1H), 4.36 (brt, 1H), 4.13 (qd, 2H), 4.07 (s, 3H), 3.92 (m, 1H), 3.47 (d, 1H), 3.14 (m, 2H), 2.81 (m, 2H), 2.49 (m, 1H), 1.76 (m, 4H), 1.24 (m, 3H), 1.02 (s, 9H).

EXAMPLE 32B

Ethyl ester of N-[trans-7-chloro-5-(4-methoxynaphthalen-1-yl)-1-neopentyl-1,2,3,5-tetrahydro-2-oxo-4,1-benzoxazepine-3-acetyl] nipecotic acid 95% yield.

MS (PCl): 621.

EXAMPLE 32C

Ethyl ester of N-[trans-7-chloro-5-(4-methoxynaphthalen-1-yl)-1-neopentyl-1,2,3,5-tetrahydro-2-oxo-4,1-benzothiazepine-3-acetyl] isonipecotic acid 94% yield.

MS (PCl): 638 (M+2H$^+$).

$^1$H NMR (300 MHz, $CDCl_3$) δ 6.90 (dd, 1H), 6.80 (d, 1H), 6.54 (s, 1H), 4.05 (s, 3H), 1.08 (s, 9H).

EXAMPLE 32D

Ethyl ester of N-[trans-7-methyl-5-(naphthalen-1-yl)-1-neopentyl-1,2,3,5-tetrahydro-2-oxo-4,1-benzoxazepine-3-acetyl]isonipecotic acid 92% yield.
MS (PCl): 572 (M+2H$^+$).
$^1$H NMR (300 MHz, CDCl$_3$) δ 6.62 (s, 1H), 6.30 (s, 1H), 3.49 (d, 1H), 1.95 (s, 3H), 1.01 (s, 9H).

EXAMPLE 32E

Ethyl ester of N-[trans-7-methyl-5-(naphthalen-1-yl)-1-neopentyl-1,2,3,5-tetrahydro-2-oxo-4,1-benzoxazepine-3-acetyl]nipecotic acid 99% yield.
MS (PCl): 572 (M+2H$^+$).
$^1$H NMR (300 MHz, CDCl$_3$) δ 6.62 (s, 1H), 6.31 (s, 1H), 3.49 (d, 1H),$_1$ 1.96 (s, 3H), 1.01 (s, 9H).

EXAMPLE 32F

Methyl ester of N-[trans-7-methyl-5-(naphthalen-1-yl)-1-neopentyl-1,2,3,5-tetrahydro-2-oxo-4,1-benzoxazepine-3-acetyl]-L-proline 99% yield.
MS (PCl): 544 (M+2H$^+$).
$^1$H NMR (250 MHz, CDCl$_3$, diastereomeric mixture) δ 6.63 and 6.61 (2s, 1H), 6.33 and 6.31 (2d, 1H), 2.01 and 1.99 (2s, 3H), 1.03 (s, 9H).

EXAMPLE 32G

Ethyl ester of N-[trans-7-methyl-5-(naphthalen-1-yl)-1-neopentyl-1,2,3,5-tetrahydro-2-oxo-4,1-benzothiazeine-3-acetyl]isonipecotic acid 89% yield.
MS (PCl): 587 (M+H$^+$).
$^1$H NMR (300 MHz, CDCl$_3$) δ 7.08 (d,1H), 6.65 (s,1H), 6.56 (s,1H), 2.06 (s, 3H), 1.09 (s, 9H).

EXAMPLE 32H

Ethyl ester of N-[trans-7-methyl-5-(naphthalen-1-yl)-1-neopentyl-1,2,3,5-tetrahydro-2-oxo-4,1-benzothiazepine-3-acetyl]nipecotic acid 93% yield.
MS (PCl): 587 (M+H$^+$).
$^1$H NMR (300 MHz, CDCl$_3$) δ 7.08 (d, 1H), 6.65 (s, 1H), 6.56 (s, 1H), 2.06 (s, 3H), 1.09 (s, 9H).

EXAMPLE 32I

Methyl ester of N-[trans-7-methyl-5-(naphthalen-1-yl)-1-neopentyl-1,2,3,5-tetrahydro-2-oxo-4,1-benzothiazepine-3-acetyl]-L-proline 98% yield.
MS (PCl): 560 (M+2H$^+$).
$^1$H NMR (250 MHz, CDCl$_3$, diastereomeric mixture) δ 6.65 (m, 1H), 6.57 (d, 1H), 2.07 and 2.05 (2s, 3H), 1.10 and 1.09 (2s, 9H).

EXAMPLE 32J

Ethyl ester of N-[trans-7-methoxy-5-(naphthalen-1-yl)-1-neopentyl-1,2,3,5-tetrahydro-2-oxo-4,1-benzoxazepine-3-acetyl]isonipecotic acid 69% yield.
MS (PCl): 588 (M+2H$^+$).
$^1$H NMR (300 MHz, CDCl$_3$) δ 6.86 (dd, 1H), 6.63 (s, 1H), 6.06 (t, 1H), 3.46 (s, 3H), 1.03 (s, 9H).

EXAMPLE 32K

Ethyl ester of N-[trans-7-methoxy-5-(naphthalen-1-yl)-1-neopentyl-1,2,3,5-tetrahydro-2-oxo-4,1-benzoxazepine-3-acetyl]nipecotic acid 97% yield.
MS (PCl): 588 (M+2H$^+$).
$^1$H NMR (300 MHz, CDCl$_3$) δ 6.86 (dd, 1H), 6.63 (s, 1H), 6.07 (m, 1H), 3.46 (s, 3H), 1.03 (s, 9H).

EXAMPLE 32L

Methyl ester of N-[trans-7-methoxy-5-(naphthalen-1-yl)-1-neopentyl-1,2,3,5-tetrahydro-2-oxo-4,1-benzoxazepine-3-acetyl]-L-proline 90% yield.
MS (PCl): 560 (M+2H$^+$).
$^1$H NMR (300 MHz, CDCl$_3$) δ 6.84 (dd, 1H), 6.62.(s, 1H), 6.05 (dd, 1H), 1.02 (s, 9H).

EXAMPLE 32M

Ethyl ester of N-[trans-7-methoxy-5-(naphthalen-1-yl)-1-neopentyl-1,2,3,5-tetrahydro-2-oxo-4,1-benzothiazepine-3-acetyl]isonipecotic acid 77% yield.
MS (PCl): 604 (M+2H$^+$).
$^1$H NMR (300 MHz, CDCl$_3$) δ 6.80 (dd, 1H), 6.64 (s, 1H), 6.32 (d, 1H), 3.53 (s, 3H), 1.10 (s, 9H).

EXAMPLE 32N

Ethyl ester of N-[trans-7-acetyl-5-(naphthalen-1-yl)-1-neopentyl-1,2,3,5-tetrahydro-2-oxo-4,1-benzothiazepine-3-acetyl]isonipecotic acid 92% yield.
MS (PCl): 615 (M+H$^+$).
$^1$H NMR (300 MHz, CDCl3) δ 6.70 (s, 1H), 2.27 (s, 3H), 1.09 (s, 9H).

EXAMPLE 33

α,β-Dimethyl ester of N-[trans-7-chloro-5-(1-naphthyl)-1-neopentyl-2-oxo-1,2,3,5-tetrahydro-4,1-benzothiazepin-3-acetyl]-L-aspartic acid 71 % yield The procedure of Example 24 was followed with the exception that trans-7-chloro-5-(1-naphthyl)-1-neopentyl-2-oxo-1,2,3,5-tetrahydro-4,1-benzothiazepin-3-acetic was used in place of trans-7-chloro-5-(1-naphthyl)-1-neopentyl-2-oxo-1,2,3,5-tetrahydro-4,1-benzoxazepin-3-acetic acid.

$^1$H NMR (CDCl$_3$) δ 1.09, 1.10 (2s, 9H); 2.43 (m, 1H); 2.76–2.9 (m, 1H); 2.94–3.12 (m, 2H); 3.38 (d, 1H); 3.66, 3.72, 3.73, 3.77 (4s, 6H); 3.9 (m, 1H); 4.48 (q, 1H); 4.8 (m, 1H); 6.62 (d, 1H); 6.77 (s, 1H); 7.27 (m, 1H); 7.39 (m, 2H); 7.49 (t, 1H); 7.59 (t, 1H); 7.89–8.04 (c and d at 7.92, total 4H).

The title compounds of Examples 34 through 37D were prepared by a procedure analogous to that described in Example 33, with the exception of 35B.

EXAMPLE 34

α,γ-Dimethyl ester of N-[trans-7-chloro-5-(1-naphthyl)-1-neopentyl-2-oxo-1,2,3,5-tetrahydro-4,1-benzothiazebin-3-acetyl]-L-glutamic acid 49% yield $^1$H NMR (CDCl$_3$) δ 1.09, 1.1 (2s, 9H); 1.99 (c, 1H); 2.2 (c, 1H); 2.39 (c, 3H); 3.01 (m, 1H); 3.38 (m, 1H); 3.64, 3.71, 3,73, 3.75 (4s, 6H); 3.9 (m, 1H); 4.48 (q, 1H); 4.57 (c, 1H); 6.42, 6.56 (2d, 1H); 6.62 (d, 1H); 6.77 (d, 1H); 7.27 (m, 1H); 7.39 (m, 2H); 7.49 (t, 1H); 7.59 (t, 1H); 7.92 (d, 3H); 7.98 (c, 1H).

EXAMPLE 35

Ethyl ester of (−)-N-[trans-7-chloro-5-(1-naphthyl)-1-neopentyl-2-oxo-1,2,3,5-tetrahydro-4,1-benzothiazepin-3-acetyl]isonipecotic acid 56% yield $^1$H NMR (CDCl$_3$) δ 1.10(s, 9H); 1.25 (c, 3H); 1.5–2.0 (c, 4H); 2.38 (d, H); 2.5 (c, 1H); 2.83 (c, 1H); 3.05–3.3 (c, 2H); 3.41 (d, 1H); 3.84 (c, 1H); 3.97 (d, 1H); 4.15 (m, 2H); 4.3 (c, 1H); 4.5 (2d, 1H); 6.64 (s, 1H); 6.77 (d, 1H); 7.29 (d, 1H); 7.41 (t, 2H); 7.5 (t, 1H); 7.6 (t, 1H); 7.91, 7.93, 7.96, 8.0, 8.02 (m, 4H).

EXAMPLE 35A

Ethyl ester of (−)-N-[trans-7-chloro-5-(1-naphthyl)-1-neopentyl-2-oxo-1,2,3,5-tetrahydro-4,1-benzothiazepin-3-acetyl]isonipecotic acid The procedure of Example 35 was used except that (−)-trans-7-chloro-5-(1-naphthyl)-1-neopentyl-2-oxo-1,2,3,5-tetrahydro-4,1-benzothiazepin-3-acetic acid (Example 22) was used as starting material.

64% yield $^1$H NMR identical to that of Example 35.

EXAMPLE 35B

Ethyl ester of (−)-N-[trans-7-chloro-5-(1-naphthyl)-1-neopentyl-2-oxo-1,2,3,5-tetrahydro-4,1-benzothiazepin-3-acetyl]isonipecotic acid A solution of 3.37 g (7.20 mmol) of (−)-trans-7-chloro-5-(1-naphthyl)-1-neopentyl-2-oxo-1,2,3,5-tetrahydro-4,1-benzothiazepin-3-acetic acid in 34 mL of dry tetrahydrofuran was cooled to 0° C. and treated with 1.25 mL (8.11 mmol, 1.1 equivalents) of ethyl isonipecotate and 3.6 mL (33 mmol, 4.6 equivalents) of 4-methylmorpholine. A 50% solution of propylphosphonic anhydride in ethyl acetate, 6.5 mL (11 mmol, 1.5 equivalents) was added dropwise over 20 minutes. The reaction mixture was stirred for 1.5 hours at 0° C., quenched by the dropwise addition of 35 mL of water, and allowed to warm to room temperature. The layers were separated, the aqueous layer was washed with ethyl acetate (2×25 mL), and the combined organic phases were washed with brine, and concentrated under vacuum to 4.44 g of a white foam. Recrystallization from isopropanol gave 4.02 g (92% yield) of the title compound as a white solid.

[α]$_D$ −197.2° (c 0.5, methanol).

$^1$H NMR (CDCl$_3$) δ 8.01–7.88 (m, 4H), 7.61–7.36 (m, 4H), 7.27 (dd, J=2.4, 8.6 Hz, 1H), 6.76 (d, J=2.3 Hz, 1H), 6.63 (s, 1H), 4.51–4.44 (m, 1H), 4.34–4.23 (m, 1H), 4.18–4.05 (m, 2H), 4.02–3.93 (m, 1H), 3.85–3.79 (m, 1H), 3.40 (d, J=13.9 Hz, 1H), 3.29–3.02 (m, 2H), 2.86–2.77 (m, 1H), 2.56–2.45 (m, 1H), 2.43–2.33 (m, 1H), 1.98–1.81 (m, 2H), 1.80–1.51 (m, 2H), 1.27–1.17 (m, 3H), 1.09 (s, 9H).

EXAMPLE 36

Ethyl ester of N-[trans-7-chloro-5-(1-naphthyl)-1-neopentyl-2-oxo-1,2,3,5-tetrahydro-4,1-benzothiazepin-3-acetyl]nipecotic acid 81% yield $^1$H NMR (CDCl$_3$) δ 1 10 (s, 9H); 1.25 (c, 3H); 1.35–1.9 (c, 3H); 2.08 (c, 1H); 2.2–3.36 (c, 6H); 3.41 (d, 1H); 3.8 (c, 1H); 3.97 (d, 1H); 4.14 (m, 2H); 4.5 (c, 1H); 6.64 (s, 1H); 6.78 (s, 1H); 7.28 (d, 1H); 7.41 (t, 2H); 7.5 (t, 1H); 7.60 (t, 1H); 7.9–8.05 (m, 4H).

EXAMPLE 37

Methyl ester of (−)-N-[trans-7-chloro-5-(1-naphthyl)-1-neopentyl-2-oxo-1,2,3,5-tetrahydro-4,1-benzothiazepin-3-acetyl]-L-proline A procedure analogous to that of Example 35A was used.

64% yield $^1$H NMR (CDCl$_3$) δ 1.09 (s, 9H); 2.01 (c, 3H); 2.18 (c, 1H); 2.42 (q, 1H); 3.2 (q, 1H); 3.36 (d, 1H); 3.63 (c, 2H); 3.69 (s, 3H); 4.04 (q, 1H); 4.44,4.49, 4.51, 4.52 (m, 2H); 6.63 (s, 1H); 6.77 (d, 1H); 7.25 (q, 1H); 7.38, 7.41, 7.43 (m, 2H); 7.49 (t, 1H); 7.61 (t, 1H); 7.91, 7.93, 7.96, 7.99, 8.00, 8.03 (m, 4H).

EXAMPLE 37A

γ-t-Butyl ester-α-methyl ester of N-[trans-7-chloro-5-(1-naphthyl)-1-neopentyl-2-oxo-1,2,3,5-tetrahydro-4,1-benzothiazepin-3-acetyl]-L-glutamic acid Less polar diastereomer 36% yield.

$^1$H NMR (250 MHz, CDCl$_3$) δ 1.1 (s, 9H); 1.47 (s, 9H); 1.94 (m, 1H); 2.18 (m, 1H); 2.3 (c, 2H); 2.41 (q, 1H); 3.0 (q, 1H); 3.38 (d, 1H); 3.73 (s, 3H); 3.92 (q, 1H); 4.47 (d, 1H); 4.55 (m, 1H); 6.45 (d, 1H);6.62 (s, 1H); 6.78 (d, 1H); 7.27 (c, 1H); 7.35–7.44 (m, 2H); 7.5 (t, 1H); 7.6 (t, 1H); 7.9–8.02 (m, 4H).

More polar diastereomer

34% yield.

$^1$H NMR (250 MHz, CDCl$_3$) δ 1.1 (s, 9H); 1.42 (s, 9H); 1.95 (m, 1H); 2.15 (m, 1H); 2.28 (q, 2H); 2.4 (q, 1H); 3.06 (q, 1H); 3.39 (d, 1H); 3.75 (s, 3H); 3.86 (q, 1H); 4.5 (d) and 4.54 (c) (total 2H); 6.54 (d, 1H); 6.63 (s, 1H); 6.77 (d, 1H); 7.28 (c, 1H); 7.4 (m 2H); 7.5 (t, 1H); 7.6 (t, 1H); 7.9–8.02 (m, 4H).

EXAMPLE 37B

β-t-Butylester-α-methyl ester of N-[trans-7-chloro-5-(1-naphthyl)-1-neopentyl-2-oxo-1,2,3,5-tetrahydro-4,1-benzothiazepin-3-acetyl]-L-aspartic acid Less polar diastereomer 14% yield.

$^1$H NMR (250 MHz, CDCl$_3$) δ 1.1 (s, 9H); 1.46 (s, 9H); 2.46 (q, 1H); 2.69 (q, 1H); 2.93 (q, 1H); 3.03 (q, 1H); 3.39 (d, 1H); 3.73 (s, 3H); 3.93 (q, 1H); 4.46 (d, 1H); 4.79 (m, 1H); 6.62 (s, 1H); 6.65 (d, 1H); 6.78 (d, 1H); 7.28 (c, 1H); 7.4 (m, 2H); 7.49 (t, 1H); 7.6 (t, 1H); 7.92 (d, 3H); 8.0 (t, 1H).

EXAMPLE 37C

Methyl ester of (−)-N-[trans-7-chloro-5-(1-naphthyl)-1-neopentyl-2-oxo-1,2,3,5-tetrahydro-4,1-benzothiazepin-3-acetyl]-D-proline A procedure similar to that described in Example 36 was used.

72% yield.

$^1$H NMR (250 MHz, CDCl$_3$) δ 1.09 (s, 9H); 1.8–2.4 (c, 5H); 2.5, 3.02, 3.18 (3q, total 2H); 3.39 (q, 1H); 3.52 (c, 1H); 3.72, 3.73 (2s, 3H); 4.0 (c, 1H); 4.45 (d and c); 4.61 (c) (total 2H); 6.63 (d, 1H); 6.76 (2d, 1H); 7.27 (m, 1H); 7.4 (c, 2H); 7.49 (t, 1H); 7.6 (c, 1H); 7.9,.7.93, 7.95, 7.98, 8.0, 8.03 (m, 4H).

$[\alpha]_D^{20}$ −200° (c 1.0, CHCl$_3$).

EXAMPLE 37D

Methyl ester of (−)-N-[trans-7-chloro-5-(1-naphthyl)-1-neopentyl-2-oxo-1,2,3,5-tetrahydro-4,1-benzothiazepin-3-acetyl]-(R)-thiazolidine-4-carboxylic acid A procedure similar to that described in Example 36 was used.

35% yield.

$^1$H NMR (250 MHz, CDCl$_3$) δ 1.09 (s, 9H); 2.49 (q, 1H); 3.15–3.32 (c, 3H); 3.38 (d, 1H); 3.72 (s, 3H); 4.0 (q, 1H); 4.45 (d, 1H); 4.54 (d, 1H); 4.75 (d, 1H); 5.1 (m, 1H); 6.64 (s, 1H); 6.78 (d, 1H); 7.28 (c, 1H); 7.40 (m, 2H); 7.5 (t, 1H); 7.61 (t, 1H); 7.9–8.02 (m, 4H).

EXAMPLE 38

N-[trans-7-chloro-5-(1-naphthyl)-1-neopentyl-2-oxo-1,2,3,5-tetrahydro-4,1-benzoxazepin-3-acetyl]-L-proline A solution of 94 mg (0.68 mmol) potassium carbonate in 2 mL water was added to a solution of 190 mg (0.34 mmol) methyl ester of N-[trans-7-chloro-5-(1-naphthyl)-1-neopentyl-2-oxo-1,2,3,5-tetrahydro-4,1-benzoxazepin-3-acetyl]-L-proline in 10 mL methanol. The resulting solution was heated at 6° C. for 3 hours, cooled to room temperature and then concentrated in vacuo. Water (30 ml) was added to the residue and the mixture was acidified with 1N aqueous hydrochloric acid then extracted with 2×40 mL ethyl acetate. The combined ethyl acetate extracts were washed with 50 mL brine, dried over anhydrous sodium sulfate, filtered and concentrated in vacuo to yield 160 mg of the title compound as an amorphous white solid (86% yield).

$^1$H NMR (CDCl$_3$): δ 1.03, 1.05 (2s, 9H); 1.81–2.07 (c, 3H); 2.88–3.18 (m, 3H); 3.38–3.79 (c, 3H); 4.5–4.65 (c and d at 4.56, total 2H); 4.68 (c, 1H); 6.54 (s, 1H); 6.62 (d, 1H); 7.3–7.65 (c, 6H); 7.73–7.97 (c and d at 7.93, total 3H).

The title compounds of Examples 38A through 54R were prepared by a procedure analogous to that described in Example 38.

EXAMPLE 38A (−)-N-[trans-7-chloro-5-(1-naphthyl)-1-neopentyl-2-oxo-1,2,3,5-tetrahydro-4,1-benzoxazepin-3-acetyl]-L-proline 53% yield $^1$H NMR (CDCl$_3$) δ 1.05 (s, 9H); 2.0 (c, 3H); 2.51 (c, 1H); 2.93 (q, 1H); 3.14 (q, 1H); 3.51 (d, 1H); 3.64 (c, 2H); 4.56 (d, 1H); 4.62 (c, 1H); 4.69 (t, 1H); 6.54 (d, 1H); 6.63 (s, 1H); 7.32–7.56 (c, 5H); 7.61 (t, 1H); 7.81 (d, 1H); 7.92 (d, 2H).

EXAMPLE 39

N-[Trans-7-chloro-5-(1-naphthyl)-1-neopentyl-2-oxo-1,2,3,5-tetrahydro-4,1-benzoxazepin-3-acetyl] isonipecotic acid 69% yield $^1$H NMR (CDCl$_3$): δ 1.04 (s, 9H); 1.5–2.0 (c, 4H); 2.57 (c, 1H); 2.88 (c, 2H); 3.17 (c, 2H); 3.5 (d, 1H); 3.93 (c, 1H); 4.36 (c, 1H); 4.57 (q, 1H); 4.69 (c 1H); 6.52 (s, 1H); 6.61 (s, 1H); 7.3–7.62 (c, 6H); 7.83 (t, 1H); 7.91 (d, 2H).

EXAMPLE 39A (−)-N-[trans-7-chloro-5-(1-naphthyl)-1-neopentyl-2-oxo-1,2,3,5-tetrahydro-4,1-benzoxazepin-3-acetyl] isonipectoic acid 99% yield 1H NMR identical to that of Example 39.

$[\alpha]_D^{20}$ −161° (methanol)

EXAMPLE 40

N-[Trans-7-chloro-5-(1-naphthyl)-1-neopentyl-2-oxo-1,2,3,5-tetrahydro-4,1-benzoxazepin-3-acetyl] nipecotic acid 69% yield $^1$H NMR (CDCl$_3$): δ 1.04 (s, 9H); 1.3–1.85 (c, 3H); 2.06 (c, 1H); 2.37–3.31 (c, 6H); 3.5 (d, 1H); 3.92 (C, 2H); 4.57 (d, 1H); 4.68 (c, 1H); 6.52 (s, 1H); 6.61 (s, 1H); 7.3–7.62 (c, 6H); 7.83 (d, 1H); 7.91 (d, 1H).

EXAMPLE 41

N-[Trans-7-chloro-5-(1-naphthyl)-1-neopentyl-2-oxo-1,2,3,5-tetrahydro-4,1-benzoxazepin-3-acetyl]-L-S-methylcysteine From the less polar ester of the title compound.

68% yield $^1$H NMR (CDCl$_3$): δ 1.04 (s, 9H); 1.9, 2.0 (2s, ratio 1:4, total 3H); 2.78–3.07 (c, 4H); 3.48 (d 1H); 4.48–4.61 (c, 2H); 4.71 (c, 1H); 6.54 (d, 1H), 6.67 (s, 1H); 7.00, 7.1 (2d, ratio 4:1, total 1H); 7.29–7.52 (c, 5H); 7.59 (t, 1H); 7.82–7.95 (c, 3H).

EXAMPLE 41A (−)-N-[trans-7-chloro-5-(1-naphthyl)-1-neopentyl-2-oxo-1,2,3,5-tetrahydro-4,1-benzoxazepin-3-acetyl]-L-S-methylcysteine 64% yield $^1$H NMR identical to that of Example 41.

$[\alpha]_D^{20}$ −174° (methanol).

EXAMPLE 42

N-[Trans-7-chloro-5-(1-naphthyl)-1-neopentyl-2-oxo-1,2,3,5-tetrahydro-4,1-benzoxazepin-3-acetyl]-L-aspartic acid 91 % yield $^1$H NMR (CDCl$_3$) δ 0.98 (s, 9H); 2.75 (c, 2H); 3.0 (c, 2H); 3.43 (d, 1H); 4.45–4.6 (c, 2H); 4.83 (c, 1H); 6.41 (d, 1H); 6.56 (s, 1H); 7.25–7.5 (c, 5H); 7.54 (t, 1H); 7.75–7.9 (c, 3H).

EXAMPLE 43

N-[Trans-7-chloro-5-(1-naphthyl)-1-neopentyl-2-oxo-1,2,3,5-tetrahydro-4,1-benzoxazepin-3-acetyl]-L-glutamic acid 73% yield $^1$H NMR (CDCl$_3$) δ 1.02 (s, 9H); 2.18 (c, 2H); 2.42 (c 2H); 2.79 (c, 1H); 2.98 (m, 1H); 3.46 (c, 1H); 4.49–4.65 (c, 3H); 6.52 (s, 1H); 6.60 (s, 1H); 6.88, 6.98 (2d, 1H); 7.26–7.64 (c, 6H); 7.8 (m, 1H); 7.9 (m, 2H).

EXAMPLE 44

N-[Trans-7-chloro-5-(1-naphthyl)-1-neopentyl-2-oxo-1,2,3,5-tetrahydro-4,1-benzoxazepin-3-acetyl]-5-aminosalicylic acid 85% yield $^1$H NMR (CDCl$_3$) δ 0.97 (s, 9H); 2.89 (2q, 2H); 3.41 (d, 1H); 4.5 (d, 1H); 4.58 (t, 1H); 6.43 (d, 1H); 6.55 (s, 1H); 6.82 (d, 1H); 7.22–7.5 (c, 7H); 7.61 (q, 1H); 7.76 (d, 1H); 7.83 (q, 2H); 7.93 (d, 1H); 8.76 (s, 1H); 11.02 (s, 1H).

EXAMPLE 45

N-[Trans-7-chloro-5-(1-naphthyl)-1-neopentyl-2-oxo-1,2,3,5-tetrahydro-4,1-benzoxazepin-3-acetyl]-4-aminosalicylic acid 80% yield $^1$H NMR (CDCl$_3$) δ 1.02 (s, 9H); 2.9 (q, 1H); 3.02 (q, 1H); 3.46 (d, 1H); 4.55 (m, 2H); 6.5 (d, 1H); 6.61 (s, 1H); 7.01 (d, 1H); 7.21 (d, 1H); 7.27–7.55 (c, 7H); 7.78 (t, 2H); 7.88 (d, 2H); 8.68 (s, 1H).

EXAMPLE 46

N-[trans-7-chloro-5-(naphthalen-1-yl)-1-neopentyl-1,2,3,5-tetrahydro-4,1-benzoxazepine-3-acetyl] nipecotic acid 75% yield.

MS (PCl): 549.

$^1$H NMR (300 MHz, (CD$_3$)$_2$SO) δ 8.31 (d, 1H), 7.92 (d, 2H), 7.66 (d, 1H), 7.48 (m, 2H), 7.29 (t,1H), 7.00 (s, 2H), 6.42 (s,1H), 6.35 (s, 1H), 4.87 (br d, 1H), 4.22 (br d, 1H), 3.78 (br d, 1H), 3.54 (d, 1H), 3.03 (m, 1H), 2.84 (d, 1H), 2.70 (m, 1H), 2.09–1.24 (c, 6H), 1.06 (s, 9H).

EXAMPLE 47

N-[trans-7-chloro-5-(naphthalen-1-yl)-1-neopentyl-1,2,3,5-tetrahydro-4,1-benzoxazepine-3-acetyl] isonipecotic acid 81% yield.

MS (PCl): 549.

$^1$H NMR (300 MHz, (CD$_3$)$_2$SO) δ 8.31 (d,1H), 7.92 (d, 2H), 7.65 (d, 1H), 7.48 (m, 2H), 7.28 (t, 1H), 7.00 (s, 2H), 6.42 (s, 1H), 6.34 (s, 1H), 4.86 (br d, 1H), 4.40 (br d, 1H), 3.72 (m, 2H), 3.54 (d, 1H), 2.84 (d, 1H), 2.70–1.24 (c, 10H), 1.06 (s, 9H).

EXAMPLE 48

N-[trans-7,8-trimethylene-5-(naphthalen-1-yl)-1-neopentyl-1,2,3,5-tetrahydro-2-oxo-4,1-benzoxazepine-3-acetyl]nipecotic acid 77% yield.

MS (PCl): 570 (M+H$^+$).

$^1$H NMR (300 MHz, (CD$_3$)$_2$SO) δ 7.99 (t, 2H), 7.83 (t, 1H), 7.61 (m, 2H), 7.49 (m, 2H), 7.38 (m, 1H), 6.45 (s, 1H), 6.21 (s, 1H), 4.36 (m, 2H), 4.14 (brt, 1H), 3.86 (brs, 1H), 3.70 (d, 1H), 3.10–2.50 (c, 7H), 1.87 (m, 4H), 1.48 (m, 4H), 0.98 (s, 9H).

EXAMPLE 49

N-[trans-7,8-trimethylene-5-(naphthalen-1-yl)-1-neopentyl-1,2,3,5-tetrahydro-2-oxo-4,1-benzoxazepine-3-acetyl]isonipecotic acid 85% yield.

MS (PCl): 570 (M+H$^+$).

$^1$H NMR (300 MHz, (CD$_3$)$_2$SO) δ 8.00 (m, 2H), 7.82 (m, 1H), 7.64 (m, 2H), 7.48 (m, 2H), 7.38 (m, 1H), 6.45 (s, 1H), 6.21 (s, 1H), 4.36 (m, 2H), 4.31 (d, 1H), 3.85 (m, 2H), 3.71 (d, 1H), 3.01–2.50 (c, 6H), 1.92 (m, 3H), 1.60 (m, 5H), 0.98 (s, 9H).

EXAMPLE 49A

N-[trans-7-chloro-5-(4-methoxynaphthalen-1-yl)-1-neopentyl-1,2,3,5-tetrahydro-2-oxo-4,1-benzoxazepine-3-acetyl]isonipecotic acid 84% yield.

MS (PCl): 593.

$^1$H NMR (250 MHz, CDCl$_3$) δ 8.35 (d, 1H), 7.72 (t, 1H), 7.67–7.29 (m, 5H), 6.89 (dd, 1H), 6.57 (d, 1H), 6.52 (s, 1H), 4.66 (m, 1H), 4.56 and 4.55 (rotamers, d, 1H), 4.37 (br t, 1H), 4.05 and 4.04 (rotamers, s, 3H), 3.93 (m, 1H), 3.47 (d, 1H), 3.13 (m, 2H), 2.85 (m, 2H), 2.52 (m, 1H), 1.96–1.53 (m, 4H), 1.02 (s, 9H).

EXAMPLE 49B

N-[trans-7-chloro-5-(4-methoxynaphthalen-1-yl)-1-neopentyl-1,2,3,5-tetrahydro-2-oxo-4,1-benzoxazepine-3-acetyl]nipecotic acid 78% yield.

MS (PCl): 593.

$^1$H NMR (250 MHz, CDCl$_3$, major rotamer or diastereomer) δ 8.35 (d, 1H), 7.70 (d, 1H), 7.48–7.29 (m, 5H), 6.90 (d, 1H), 6.57 (m, 1H), 6.52 (s, 1H), 4.66 (dd, 1H), 4.55 (d, 1H), 4.05 (s, 3H), 3.93 (m, 1H), 3.47 (d, 1H), 3.14–2.83 (m, 5H), 2.06 (m, 1H), 1.72–1.25 (m, 4H), 1.02 (s, 9H).

EXAMPLE 49C

N-[Trans-7-chloro-5-(4-methoxynaphthalen-1-yl)-1-neopentyl-1,2,3,5-tetrahydro-2-oxo-4,1-benzothiazepine-3-acetyl]isonipecotic acid 76% yield.

MS (PCl): 610 (M+2H$^+$).

$^1$H NMR (300 MHz, CD$_3$OD) δ 7.13 (d, 1H), 6.60 (d, 1H), 6.36 (s, 1H), 4.01 (s, 3H), 0.98 (s, 9H).

EXAMPLE 49D

N-[Trans-7-chloro-5-(4-methoxynaphthalen-1-yl)-1-neopentyl-1,2,3,5-tetrahydro-2-oxo-4,1-benzothiazepine-3-acetyl]-L-proline Purification by flash column chromatography (ether) of the methyl ester of N-[trans-7-chloro-5-(4- methoxynaphthalen-1-yl)-1-neopentyl-1,2,3,5-tetrahydro-2-oxo-4,1-benzothiazepine-3-acetyl]-L-proline gave separation of the two diastereomers.

Hydrolysis of the higher Rf diastereomer:
77% yield.
MS (PCl): 596 (M+2H$^+$).
$^1$H NMR (250 MHz, CDCl$_3$) δ 6.92 (d, 1H), 6.82 (d, 1H), 6.55 (s, 1H), 4.07 (s, 3H), 1.09 (s, 9H).

Hydrolysis of the lower R$_f$ diastereomer:
99% yield.
MS (PCl): 596 (M+2H$^+$).
$^1$H NMR (250 MHz, CDCl$_3$) δ 6.91 (d, 1H), 6.82 (d, 1H), 6.55 (s, 1H), 4.06 (s, 3H), 1.08 (s, 9H).

EXAMPLE 49E

N-[Trans-7-chloro-5-(4-methoxynaphthalen-1-yl)-1-neopentyl-1,2,3,5-tetrahydro-2-oxo-4,1-benzothiazepine-3-acetyl]-D-proline Purification by flash column chromatography (4:1 ether/hexanes) of the methyl ester of N-[trans-7-chloro-5-(4-methoxynaphthalen-1-yl)-1-neopentyl- 1,2,3,5-tetrahydro-2-oxo-4,1-benzothiazepine-3-acetyl]-D-proline gave separation of the two diastereomers.

Hydrolysis of the higher R$_f$ diastereomer:
86% yield.
$^1$H NMR (250 MHz, CDCl$_3$) δ 6.92 (d, 1H), 6.82 (d, 1H), 6.55 (s, 1H), 4.06 (s, 3H), 1.09 (s, 9H).

Hydrolysis of the lower R$_f$ diastereomer:
78% yield.
$^1$H NMR (250 MHz, CDCl$_3$) δ 6.91 (d, 1H), 6.82 (d, 1H), 6.56 (s, 1H), 4.06 (s, 3H), 1.08 (s, 9H).

EXAMPLE 49F

N-[Trans-7-methyl-5-(naphthalen-1-yl)-1-neopentyl-1,2,3,5-tetrahydro-2-oxo-4,1-benzoxazepine-3-acetyl]isonipecotic acid 94% yield.
MS (PCl): 544 (M+2H$^+$).
$^1$H NMR (300 MHz, CDCl$_3$) δ 6.62 (s, 1H), 6.32 (s, 1H), 3.51 (d, 1H), 2.00 (s, 3H), 1.03 (s, 9H).

EXAMPLE 49G

N-[Trans-7-methyl-5-(naphthalen-1-yl)-1-neopentyl-1,2,3,5-tetrahydro-2-oxo-4,1-benzoxazepine-3-acetyl]nipecotic acid 90% yield.
MS (PCl): 544 (M+2H$^+$).
$^1$H NMR (300 MHz, CDCl$_3$) δ 6.31 (s, 1H), 3.50 (d, 1H), 1.99 (s, 3H), 1.01 (s, 9H).

EXAMPLE 49H

N-[Trans-7-methyl-5-(naphthalen-1-yl)-1-neopentyl-1,2,3,5-tetrahydro-2-oxo-4,1-benzoxazepine-3-acetyl]-L-proline 77% yield.
MS (PCl): 529 (M+H$^+$).
$^1$H NMR (250 MHz, CDCl$_3$) δ 6.63 (d, 1H), 6.34 (s,1H), 2.03 (s, 3H), 1.03 (s, 9H).

EXAMPLE 49I

N-[Trans-7-methyl-5-(naphthalen-1-yl)-1-neopentyl-1,2,3,5-tetrahydro-2-oxo-4,1-benzothiazepine-3-acetyl]isonipecotic acid 93% yield.
MS (PCl): 559 (M+H$^+$).
$^1$H NMR (250 MHz, CDCl$_3$) δ 7.10 (dd, 1H), 6.66 (s, 1H), 6.58 (d, 1H), 2.07 (s, 3H), 1.10 (s, 9H).

EXAMPLE 49J

N-[Trans-7-methyl-5-(naphthalen-1-yl)-1-neopentyl-1,2,3,5-tetrahydro-2-oxo-4,1-benzothiazepine-3-acetyl]nipecotic acid 99% yield.
MS (PCl): 559 (M+H$^+$).
$^1$H NMR (250 MHz, CDCl$_3$) δ 7.10 (d, 1H), 6.65 (s, 1H), 6.57 (s, 1H), 2.07 (s, 3H), 1.10(s,9H).

EXAMPLE 49K

N-[Trans-7-methyl-5-(naphthalen-1-yl)-1-neorentyl-1,2,3,5-tetrahydro-2-oxo-4,1-benzothiazepine-3-acetyl]-L-proline 66% yield.
MS (PCl): 545 (M+H$^+$).
$^1$H NMR (250 MHz, CDCl$_3$) δ 6.66 (s, 1H), 6.59 (s,$_1$H), 2.08 (s, 3H), 1.10 (s, 9H).

EXAMPLE 49L

N-[Trans-7-methoxy-5-(naphthalen-1-yl)-1-neopentyl-1,2,3,5-tetrahydro-2-oxo-4,1-benzoxazepine-3-acetyl]isonipecotic acid 92% yield.
MS (PCl): 559 (M+H$^+$).
1H NMR (300 MHz, CDCl$_3$) δ 6.86 (dd, 1H), 6.62 (s, 1H), 6.06 (t, 1H), 3.44 (s, 3H), 1.03 (s, 9H).

EXAMPLE 49M

N-[Trans-7-methoxy-5-(naphthalen-1-yl)-1-neopentyl-1,2,3,5-tetrahydro-2-oxo-4,1-benzoxazepine-3-acetyl]nipecotic acid 98% yield.
MS (PCl): 559 (M+H$^+$).
$^1$H NMR (300 MHz, CDCl$_3$) δ 6.86 (d, 1H), 6.62 (s, 1H), 6.06 (m, 1H), 3.44 (s, 3H), 1.02 (s, 9H).

EXAMPLE 49N

N-[Trans-7-methoxy-5-(naphthalen-1-yl)-1-neopentyl-1,2,3,5-tetrahydro-2-oxo-4,1-benzoxazepine-3-acetyl]-L-proline 74% yield.
MS (PCl): 545 (M+H$^+$).
$^1$H NMR (300 MHz, CDCl$_3$) δ 6.88 (dd, 1H), 6.63 (d, 1H), 6.07 (t, 1H), 3.45 (s, 3H), 1.03 and 1.02 (2s, 9H).

EXAMPLE 49O

N-[Trans-7-methoxy-5-(naphthalen-1-yl)-1-neopentyl-1,2,3,5-tetrahydro-2-oxo-4,1-benzothiazepine-3-acetyl]isonipecotic acid quantitative yield.
MS (PCl): 575 (M+H$^+$).

¹H NMR (300 MHz, CDCl₃) δ 6.81 (dd, 1H), 6.64 (s, 1H), 6.32 (d, 1H), 3.53 (s, 3H), 1.09 (s, 9H).

EXAMPLE 49P

N-[Trans-7-acetyl-5-(naphthalen-1-yl)-1-neopentyl-1,2,3,5-tetrahydro-2-oxo-4,1-benzothiazepine-3-acetyl]isonipecotic acid 83% yield.

¹H NMR (300 MHz, CDCl₃) δ 6.70 (s, 1H), 2.27 (s, 3H), 1.09 (s, 9H).

EXAMPLE 50

N-[Trans-7-chloro-5-(1-naphthyl)-1-neopentyl-2-oxo-1,2,3,5-tetrahydro-4,1-benzothiazepin-3-acetyl]-L-aspartic acid 100% yield ¹H NMR (CDCl₃): δ 1.05 (s, 9H); 2,47 (c, 1H); 2.85 (c, 1H); 3.08 (c, 2H); 3.37 (d, 1H); 3.92 (c, 1H); 4.4 (d,1H); 4.85 (c, ₁H); 6.55 (d, 1H); 6.75 (s, ₁H); 7.2–7.6 (c, 5H); 7.82–8.0 (c, 4H).

EXAMPLE 51

N-[Trans-7-chloro-5-(1-naphthyl)-1-neopentyl-2-oxo-1,2,3,5-tetrahydro-4,1-benzothiazepin-3-acetyl]-L-glutamic acid 96% yield ¹H NMR (CDCl₃) δ 1.08 (s, 9H); 2.2 (c, 2H); 2.4–2.56 (c, 3H); 3.06 (c, 1H); 3.38(q, 1H); 3.91 (m, 1H); 4.46 (q, 1H); 4.6 (c, 1H); 6.59 (s, 1H); 6.77 (s, 1H); 6.9, 7.07 (2d, 1H); 7.24–7.62 (c, 5H); 7.86–8.0 (c, 4H).

EXAMPLE 52

N-[Trans-7-chloro-5-(1-naphthyl)-1-neopentyl-2-oxo-1,2,3,5-tetrahydro-4,1-benzothiazepin-3-acetyl] isonipecotic acid 93% yield ¹H NMR (CDCl₃) δ 1.10(s, 9H); 1.5–2.05 (c, 4H); 2.38 (d, 1H); 2.58 (c, 1H); 2.87 (c, 1H); 3.05–3.32 (c, 2H); 3.41 (d, 1H); 3.85 (c, ₁H); 3.98 (d, 1H); 4.3 (c, 1H); 4.49 (2d, 1H); 6.64 (s, 1H); 6.77 (d, 1H); 7.3 (d, 1H); 7.41 (t, 2H); 7.5 (t, 1H); 7.6 (t, 1H); 7.91, 7.93, 7.96, 8.0, 8.02 (m, 4H).

EXAMPLE 52A

N-[(−)-trans-7-chloro-5-(1-naphthyl)-1-neopentyl-2-oxo-1,2,3,5-tetrahydro-4,1-benzothiazepin-3-acetyl] isonipecotic acid 97% yield ¹H NMR identical to that of Example 52.

[α]_D²⁰ −189° (methanol)

EXAMPLE 53

N-[Trans-7-chloro-5-(1-naphthyl)-1-neopentyl-2-oxo-1,2,3,5-tetrahydro-4,1-benzothiazepin-3-acetyl] nipecotic acid 84% yield ¹H NMR (CDCl₃) δ 1.1(s, 9H); 1.35–1.92 (C, 3H); 2.1 (c, 1H); 2.32–3.35 (c, 6H); 3.41 (d, 1H); 3.8 (c, 1H); 3.98 (d, 1H); 4.48 (d, 1H); 6.64 (s, 1H); 6.77 (s, 1H); 7.28 (d, 1H); 7.4 (c, 2H); 7.5 (t, 1H); 7.6 (t, 1H); 7.88–8.06 (c, 4H).

EXAMPLE 54

N-[(−)-trans-7-chloro-5-(1-naphthyl)-1-neopentyl-2-oxo-1,2,3,5-tetrahydro-4,1-benzothiazepin-3-acetyl]-L-proline 97% yield ¹H NMR (CDCl₃) δ 1.10(s, 9H); 2.04 (c, 3H); 2.3–2.5 (c, 2H); 3.2 (q, 1H); 3.41 (d, 1H); 3.6 (c, 2H); 4.0 (d, 1H); 4.46 (d, 1H); 4.57 (d, 1H); 6.64 (s, 1H); 6.79 (d, 1H); 7.3 (q, 1H); 7.41 (q, 2H); 7.50 (t, 1H); 7.61 (t, 1H); 7.92, 7.94, 7.99, 8.02 (m, 4H).

EXAMPLE 54A

Trans-7-methylthio-5-(1-naphthyl)-1-neopentyl-2-oxo-1,2,3,5-tetrahydro-4,1-benzoxazepin-3-acetic acid 94% yield.

¹H NMR (250 MHz, CDCl₃) δ 1.04 (s, 9H), 2.07 (s, 3H); 2.93 (q, 1H); 3.12 (q, 1H); 3.5 (d, 1H); 4.52 (c) and 4.57 (d) (total 2H); 6.4 (d, 1H); 6.63 (s, 1H); 7.24 (m, 1H); 7.32 (m, 2H); 7.47 (m, 2H); 7.58 (t, 1H); 7.84 (d, 1H); 7.89 (d, 2H).

EXAMPLE 54B

Trans-7-trifluoromethoxy-5-(1-naphthyl)-1-neopentyl-2-oxo-1,2,3,5-tetrahydro-4,1-benzoxazepin-3-acetic acid 97% yield.

¹H NMR (250 MHz, CDCl₃) δ 1.04 (s, 9H); 2.94 (q, 1H); 3.17 (q, 1H); 3.52 (d, 1H); 4.52 (q, 1H); 4.6 (d, 1H); 6.39 (d, 1H); 6.63 (s, 1H); 7.25 (c, 1H); 7.31 (t, 1H); 7.47 (q, 3H); 7.59 (t, 1H); 7.85 (d, 1H); 7.92 (d, 2H).

EXAMPLE 54C

Trans-7,8-ethylenedioxy-5-(1-naphthyl)-1-neopentyl-2-oxo-1,2,3,5-tetrahydro-4,1-benzoxazepin-3-acetic acid 49% yield.

¹H NMR (250 MHz, CDCl₃) δ 1.06 (s, 9H); 2.93 (q, 1H); 3.1 (q, 1H); 3.4 (d, 1H); 4.12 (c, 2H); 4.2 (c, 2H); 4.5 (c, 1H); 4.55 (c, 1H); 6.05 (s, 1H); 6.59 (s, 1H); 6.94 (s, 1H); 7.32 (m, 1H); 7.44 (t, 1H); 7.56 (t, 2H); 7.86 (q, 3H).

EXAMPLE54D

Trans-7-trifluoromethyl-5-(1-naphthyl)-1-neopentyl-2-oxo-1,2,3,5-tetrahydro-4,1-benzoxazepin-3-acetic acid 85% yield.

¹H NMR (250 MHz, CDCl₃) δ 1.05 (s, 9H); 2.94 (q, 1H); 3.18 (q, 1H); 3.59 (d, 1H); 4.5 (q, 1H); 4.62 (d, 1H); 6.67 (s, 1H); 6.84 (s, 1H); 7.31 (t, 1H); 7.45 (2d, 2H); 7.62 (m, 3H); 7.87 (d, 1H); 7.93 (d, 2H).

EXAMPLE 54E

N-[Trans-7-chloro-5-(1-naphthyl)-1-neopentyl-2-oxo-1,2,3,5-tetrahydro-4,1-benzoxazepin-3-acetyl]-1-amino-1-cyclopentanecarboxylic acid 58% yield.

¹H NMR (250 MHz, DMSO-d₆) δ 0.96 (s, 9H); 1.66 (c, 4H); 1.93 (c, 4H); 2.56, 2.68 (2q, 2H); 3.43 (m, 1H); 3.71 (d,

1H); 4.38 (c, 2H); 6.23 (d, 1H); 6.45 (s, 1H); 7.4 (c, 2H); 7.48–7.64 (c, 3H); 7.82 (d, 2H); 8.02 (c, 2H).

EXAMPLE 54F

N-[Trans-7-chloro-5-(1-naphthyl)-1-neopentyl-2-oxo-1,2,3,5-tetrahydro-4,1-benzoxazepin-3-acetyl-1-amino-1-cyclopropanecarboxylic acid 12% yield.

$^1$H NMR (250 MHz, CDCl$_3$) δ 1.03 (s, 9H); 1.22 (c, 2H); 1.6 (c, 2H); 2.73 (q, 1H); 2.95 (q, 1H); 3.47 (d, 1H); 4.54 (c, 2H); 6.52 (d, 1H); 6.61 (s, 1H); 6.67 (s, 1H); 7.36 (c, 3H); 7.47 (t, 2H); 7.59 (t, 1H); 7.85 (d, 1H); 7.92 (d, 2H).

EXAMPLE 54G (−)-N-[Trans-7-chloro-5-(1-naphthyl)-1-neopentyl-2-oxo-1,2,3,5-tetrahydro-4,1-benzoxazepin-3-acetyl]-L-methioninre 55% yield.

$^1$H NMR (250 MHz, CDCl$_3$) δ 1.04 (s, 9H); 1.92–2.28 (c, 5H); 2.54 (c, 2H); 2.81 (q, 1H); 2.97 (q, 1H); 3.48 (d, 1H); 4.54 (m, 2H); 4.66 (m, 1H); 6.53 (d, 1H); 6.62 (s, 1H); 6.69 (d, 1H); 7.3–7.41 (c, 3H); 7.46 (t, 2H); 7.59 (t, 1H); 7.84 (d, 1H); 7.91 (d, 2H);

$[\alpha]_D^{21}$ −158.4° (c 1.0, MeOH).

EXAMPLE 54H

N-[Trans-7-chloro-5-(1-naphthyl)-1-neopentyl-2-oxo-1,2,3,5-tetrahydro-4,1-benzoxazepin-3-acetyl]-cis-4-hydroxy-D-proline 79% yield.

$^1$H NMR (250 MHz, CDCl$_3$) δ 1.02, 1.04 (2s, 9H); 1.95–2.3 (c, 1H); 2.5 (q, 1H); 2.9 (q, 1H); 3.14 (q, 1H); 3.47 (d, 1H); 3.56–3.82 (c, 2H); 4.13 (m, 1H); 4.54 (q, 1H); 4.67 (t, 2H); 6.54 (t, 1H); 6.61 (d, 1H); 7.3–7.64 (c, 6H); 7.7 (d), 7.84 (d) (total 1H); 7.92 (d, 2H).

EXAMPLE 54I

N-[Trans-7-chloro-5-(1-naphthyl)-1-neopentyl-2-oxo-1,2,3,5-tetrahydro-4,1-benzoxazepin-3-acetyl]-trans-4-hydroxy-L-proline 80% yield.

$^1$H NMR (250 MHz, CDCl$_3$ δ 1.03 (s, 9H); 2.24 (c, 1H); 2.5 (c, 1H); 2.88 (q, 1H); 3.0 (c, 1H); 3.18 (q, 1H); 3.49 (d, 2H); 4.5 (c, 2H); 4.7 (c, 2H); 6.54 (s, 1H); 6.62 (s, 1H); 7.3–7.64 (c, 6H); 7.81 (t, 1H); 7.92 (d, 2H).

EXAMPLE 54J

N-[Trans-7-chloro-5-(1-naphthyl)-1-neopentyl-2-oxo-1,2,3,5-tetrahydro-4,1-benzoxazepin-3-acetyl]-4-azetidinecarboxylic acid 86% yield.

$^1$H NMR (250 MHz, CDCl3) δ 1.03, 1.04 (2s, 9H); 2.62 (q), 2.7 (c), 2.8 (q) (total 3H); 3.47 (d, 1H); 4.04.68 (c, 6H); 6.51 (s, 1H); 6.61 (s, 1H); 7.35 (c, 3H); 7.4–7.64 (c, 3H); 7.8 (q, 1H); 7.9 (c, 2H).

EXAMPLE 54K

N-[Trans-7-chloro-5-(1-naphthyl)-1-neopentyl-2-oxo-1,2,3,5-tetrahydro-4,1-benzoxazepin-3-acetyl]-D-proline 96% yield.

$^1$H NMR (250 MHz, CDCl$_3$) δ 1.04 (s, 9H); 1.8–2.1 (c, 3H); 2.46 (c, 1H); 3.0 (m, 2H); 3.44–3.6 (c and d at 3.49, 2H); 3.75 (c, 1H); 4.56 (d) and 4.6 (c) (total 2H); 4.7 (t, 1H); 6.54 (d, 1H); 6.61 (s, 1H); 7.32–7.6 (c, 6H); 7.76 (d, 1H); 7.93 (d, 2H).

EXAMPLE 54L (−)-N-[Trans-7-chloro-5-(1-naphthyl)-1-neopentyl-2-oxo-1,2,3,5-tetrahydro-4,1-benzoxazepin-3-acetyl]-L-pipecolinic acid 81% yield.

$^1$H NMR (250 MHz, CDCl$_3$) δ 1.04 (s, 9H); 1.4–1.8 (c, 5H); 2.25 (c, 1H); 2.86 (q, 1H); 3.2 (m, 1H); 3.32 (q, 1H); 3.51 (d, 1H); 3.9 (c, 1H); 4.57 (d, 1H); 4.68 (q, 1H); 5.28 (c, 1H); 6.52 (d, 1H); 6.62 (s, 1H); 7.3–7.65 (c, 6H); 7.9 (c, 3H).

$[\alpha]_D^{20}$ −195.6° (c 0.91, CHCl$_3$).

EXAMPLE 54M (−)-N-[Trans-7-chloro-5-(1-naphthyl)-1-neopentyl-2-oxo-1,2,3,5-tetrahydro-4,1-benzoxazepin-3-acetyl]-(−)-nipecotic acid 62% yield.

$^1$H NMR (250 MHz, CDCl$_3$) identical to that of Example 40.

EXAMPLE 54N

N-[Trans-7-trifluoromethyl-5-(1-naphthyl)-1-neopentyl-2-oxo-1,2,3,5-tetrahydro-4,1-benzoxazepin-3-acetyl]nipecotic acid 78% yield.

$^1$H NMR (250 MHz, CDCl$_3$) δ 1.04 (s, 9H); 1.5–1.85 (c, 3H); 2.05 (c, 1H); 2.4–3.5 (c, 6H); 3.58 (d, 1H); 3.9 (c, 1H); 4.6 (d, 1H); 4.66 (c, 1H); 6.65 (s, 1H); 6.81 (d, 1H); 7.32 (c, 1H); 7.46 (t, 2H); 7.6 (s and c, 3H); 7.86 (t, 1H); 7.92 (d, 2H).

EXAMPLE 54O

N-[Trans-7-trifluoromethyl-5-(1-naphthyl)-1-neopentyl-2-oxo-1,2,3,5-tetrahydro-4,1-benzoxazepin-3-acetyl]isonipecotic acid 84% yield.

$^1$H NMR (250 MHz, CDCl$_3$) δ 1.04 (s, 9H); 1.46–2.0 (c, 4H); 2.56 (c, 1H); 2.87 (c, 2H); 3.17 (c, 2H); 3.58 (d, 1H); 3.92 (c, 1H); 4.34 (c, 1H); 4.6 (2d, 1H); 4.66 (c, 1H); 6.65 (s, 1H); 6.82 (s, 1H); 7.32 (t, 1H); 7.48 (c, 2H); 7.6 (s and c, 3H); 7.85 (t, 1H); 7.92 (d, 2H).

EXAMPLE 54P

N-[Trans-7-trifluoromethyl-5-(1-naphthyl)-1-neopentyl-2-oxo-1,2,3,5-tetrahydro-4,1-benzoxazepin-3-acetyl]-L-proline 80% yield.

$^1$H NMR (250 MHz, CDCl$_3$) δ 1.04,1.05 (2s, 9H); 1.8–2.1 (c, 3H); 2.86–3.23 (m, 3H); 3.4–3.8 (c, 3H); 4.59 (d and c, 2H); 4.69 (c, 1H); 6.66 (d, 1H); 6.84 (s, 1H); 7.34 (c, 1H); 7.48 (c, 2H); 7.62 (c, 3H); 7.8 (q, 1H); 7.93 (d, 2H).

EXAMPLE 54Q (−)-N-[Trans-7-chloro-5-(1-naphthyl)-1-neopentyl-2-oxo-1,2,3,5-tetrahydro-4,1-benzothiazepin-3-acetyl]-D-proline 99% yield.

¹H NMR (250 MHz, CDCl₃) δ 1.1 (s, 9H); 2.03 (c, 3H); 2.42–2.56 (c, 2H); 3.22 (q, 1H); 3.4–3.6 (c and d at 3.42, 2H); 3.82 (c, 1H); 4.0 (q, 1H); 4.43 (d, 1H); 4.56 (d, 1H); 6.64 (s, 1H); 6.79 (d, 1H); 7.3 (q, 1H); 7.41 (q, 2H); 7.51 (t, 1H); 7.6 (t, 1H); 7.92, 7.94, 7.97, 7.98 and 8.0 (m, 4H);

EXAMPLE 54R (−)-N-[Trans-7-chloro-5-(1-naphthyl)-1-neopentyl-2-oxo-1,2,3,5-tetrahydro-4,1-benzothiazepin-3-acetyl]-(R)-thiazolidine-carboxylic acid 78% yield.

¹H NMR (250 MHz, CDCl₃) δ 1.1 (s, 9H); 2.5 (q, 1H); 3.2–3.5 (c, 4H); 4.0 (q, 1H); 4.45 (d, 1H); 4.51 (d, 1H); 4.75 (d, 1H); 5.04 (c, 1H); 6.64 (s, 1H); 6.79 (d, 1H); 7.3 (c, 1H); 7.38 (m, 2H); 7.5 (t, 1H); 7.61 (t, 1H); 7.9–8.02 (m,4H).

EXAMPLE 55

(−)-N-[trans-7-chloro-5-(1-naphthyl)-1-neopentyl-2-oxo-1,2,3,5-tetrahydro-4,1-benzoxazepin-3-acetyl]-L-aspartic acid-α-methyl ester Trifluoroacetic acid (1.5 ml) was added to a solution of 68 mg (0.1 mmol) of the less polar diastereomer of β-t-butyl ester-α-methyl ester of N-[trans-7-chloro-5-(1-naphthyl)-1-neopentyl-2-oxo-1,2,3,5-tetrahydro-4,1-benzoxazepin-3-acetyl]-L-aspartic acid in 1.5 mL dichloromethane at room temperature. The resulting solution was stirred at room temperature for 3 hours, then concentrated in vacuo. The residue was triturated 4× with hexane and filtered to yield 41 mg (71 % yield) of the title compound as a white solid.

¹H NMR (CDCl₃) δ 1.02 (s, 9H); 2.82 (c, 2H); 3.07 (c, 3H); 3.47 (d, 1H); 3.67 (s, 3H); 4.55 (c, 2H); 4.86 (c, 1H); 6.53 (d, 1H); 6.59 (s, 1H); 7.29–7.5 (c, 5H); 7.6 (t, 1H); 7.86 (d, 1H); 7.92 (d, 2H).

EXAMPLE 56

(+)-N-[trans-7-chloro-5-(1-naphthyl)-1-neopentyl-2-oxo-1,2,3,5-tetrahydro-4,1-benzoxazepin-3-acetyl]-L-aspartic acid-α-methyl ester Following a procedure analogous to that described in Example 55 but using the more polar diastereomer as starting material, the title compound was obtained as white solid in 82% yield.

¹H NMR (CDCl₃) δ 1.03 (s, 9H); 2.81 (c, 2H); 3.0 (c, 2H); 3.48 (d, 1H); 3.72 (s, 3H): 4.54 (c, 2H); 4.81 (c, 1H); 6.52 (d, 1H); 6.6 (s, 1H); 7.27–7.51 (c, 5H); 7.58 (t, 1H); 7.81 (d, 1H); 7.9 (d, 2H).

EXAMPLE 57

(−)-N-[trans-7-chloro-5-(1-naphthyl)-1-neopentyl-2-oxo-1,2,3,5-tetrahydro-4,1-benzoxazepin-3-acetyl]-L-glutamic acid-α-methyl ester Following a procedure analogous to that described in Example 55 but using the less polar diastereomer of γ-t-butyl ester-α-methyl ester of N-[trans-7-chloro-5-(1-naphthyl)-1-neopentyl-2-oxo-1,2,3,5-tetrahydro-4,1-benzoxazepin-3-acetyl]-L-glutamic acid, the title compound was obtained as a white solid in 88% yield.

¹H NMR (CDCl₃) δ 1.03 (s, 9H); 1.97 (m, 1H); 2.24 (c, 1H); 2.44 (c, 2H); 2.8 (q, 1H); 2.98 (q, 1H); 3.48 (d, 1H); 3.69 (s, 3H); 4.59 (c, 3H); 6.52 (d, 1H); 6.60 (s, 1H); 6.74 (d, 1H); 7.3–7.5 (c, 5H); 7.59 (d, 1H); 7.84 (d, 1H); 7.91 (d, 2H).

EXAMPLE 58

(+)-N-[trans-7-chloro-5-(1-naphthyl)-1-neopentyl-2-oxo-1,2,3,5-tetrahydro-4,1-benzoxazepin-3-acetyl]-L-glutamic acid-a methyl ester Following a procedure analogous to that described in Example 55 but using the more polar diastereomer of γ-t-butyl ester-α-methyl ester of N-[trans-7-chloro-5-(1-naphthyl)-1-neopentyl-2-oxo-1,2,3,5-tetrahydro-4,1-benzoxazepin-3-acetyl]-L-glutamic acid, the title compound was obtained as a white solid in 96% yield.

¹H NMR (CDCl₃) δ 1.03 (s, 9H); 1.93 (m, 1H); 2.18 (m, 1H); 2.36 (c, 2H); 2.82 (q, 1H); 2.98 (q, 1H); 3.48 (d, 1H); 3.72 (s, 3H); 4.58 (c, 3H); 6.53 (d, 1H); 6.62 (s, 1H); 7.01 (d, 1H); 7.3–7.52 (c, 5H); 7.59 (t, 1H); 7.83 (d, 1H); 7.90 (d, 2H).

EXAMPLE 58A (−)-N-[Trans-7-chloro-5-(1-naphthyl)-1-neopentyl-2-oxo-1,2,3,5-tetrahydro-4,1-benzothiazepin-3-acetyl]-L-glutamic acid-α-methyl ester A procedure similar that described in Example 55 was used using the less polar diastereomer from Example 37A.

78% yield.

¹H NMR (250 MHz, CDCl₃) δ 1.09 (s, 9H); 1.97 (c, 1H); 2.28 (c, 1H);, 2.48 (c, 3H); 3.0 (q, 1H); 3.38 (d, 1H); 3.74 (s, 3H); 3.96 (c, 1H); 4.45 (d, 1H); 4.6 (c, 1H); 6.6 (s, 1H); 6.65 (d, 1H); 6.78 (d, 1H); 7.28(c, 1H); 7.39 (m, 2H); 7.5 (t, 1H); 7.59 (t, 1H); 7.88–8.0 (c, 4H);

$[\alpha]_D^{20}$ −190° (c 1.0, CHCl₃).

EXAMPLE 58B (+)-N-[Trans-7-chloro-5-(1-naphthyl)-1-neopentyl-2-oxo-1,2,3,5-tetrahydro-4,1-benzothiazepin-3-acetyl]-L-glutamic acid-α-methyl ester A procedure similar to that described in Example 56 was used using the more polar diastereomer from Example 37A.

75% yield.

¹H NMR (250 MHz, CDCl₃) δ 1.09 (s, 9H); 2.0 (c, 1H); 2.2 (c, 1H); 2.46 (c, 3H); 3.07 (q, 1H); 3.39 (d, 1H); 3.75 (s, 3H); 3.87 (c, 1H); 4.47 (d, 1H); 4.58 (c, 1H); 6.61 (s, 1H); 6.77 (d, 1H); 6.94 (d, 1H); 7.27 (c, 1H); 7.3–7.45 (m, 2H); 7.49 (t, 1H); 7.58 (t, 1H); 7.88–8.02 (c, 4H).

$[\alpha]_D^{20}$ −184.70 (c 1.0, CHCl₃).

EXAMPLE 58C (−)-N-[Trans-7-chloro-5-(1-naphthyl)-1-neopentyl-2-oxo-1,2,3,5-tetrahydro-4,1-benzothiazepin-3-acetyl]-L-aspartic acid-α-methyl ester A procedure similar that described in Example 55 was used using Example 37B as starting material.

69% yield.

¹H NMR (250 MHz, CDCl₃) δ 1.1 (s, 9H); 2.48 (q, 1H); 2.8 (q, 1H); 3.13 (c, 2H); 3.4 (d, 1H); 3.73 (s, 3H); 4.04 (q, 1H); 4.42 (d, 1H); 4.87 (c, 1H); 6.58 (s, 1H); 6.8 (d, 1H); 7.25–7.47 (c, 3H); 7.5 (t, 1H); 7.6 (t, 1H); 7.92 (d, 3H); 7.99 (t, 1H).

EXAMPLE 59

Methyl ester of N-[trans-7-chloro-5-(1-naphthyl)-1-neopentyl-2-oxo-1,2,3,5-tetrahydro-4,1-benzoxazepin-3-acetyl]-5-aminosalicylic acid To a mixture of 129 mg (0.51 mmol) 2-chloro-1-methylpyridinium iodide in 10 mL dichloromethane was added 208 mg (0.46 mmol) trans-7-chloro-5-(1-naphthyl)-1-neopentyl-2-oxo-1,2,3,5-tetrahydro-4,1-benzoxazepin-3-acetic acid, 92 mg (0.55 mmol) methyl 5-amino salicylate and 0.064 mL (0.46 mmol) triethylamine. The reaction mixture was refluxed under nitrogen for 7 hr and the resulting solution was cooled to room temperature and concentrated in vacuo. The residue was partitioned between 20 mL water and 60 mL ethyl acetate and the ethyl acetate layer was washed with 25 mL 1N aqueous hydrochloric acid, 25 mL water and 25 mL brine. The ethyl acetate solution was dried over anhydrous sodium sulfate, filtered and concentrated in vacuo. The residue was chromatographed on 100 g silica gel, eluting with 3:2 hexane/ethyl acetate to yield 132 mg (49% yield) of the title compound as a white solid.

$^1$NMR (CDCl$_3$): δ 1.05 (s, 9H); 2.9 (q, 1H); 3.03 (q, 1H); 3.48 (d, 1H); 3.94 (s, 3H), 4.55, 4.58, 4.6, 4.62 ( 2d, 2H); 6.53 (d, 1H); 6.65 (s, 1H); 6.94 (d, 1H); 7.38–7.58 (c, 7H); 7.73 (s, 1H); 7.82 (d, 1H); 7.92 (d, 2H); 8.04 (d, 1H).

EXAMPLE 60

Methyl ester of N-[trans-7-chloro-5-(1-naphthyl)-1-neopentyl-2-oxo-1,2,3,5-tetrahydro-4,1-benzoxazepin-3-acetyl]4-aminosalicylic acid Using a procedure analogous to that described in Example 59 except that methyl 4-amino salicylate was used as starting material, the title compound was obtained as a white solid in 36% yield.

$^1$H NMR (CDCl$_3$) δ 1.05 (s, 9H); 2.91 (q, 1H); 3.06 (q, 1H); 3.48 (d, 1H); 3.93 (s, 3H); 4.58 (c, 2H); 6.54 (s, 1H); 6.65 (s, 1H); 7.03 (d, 1H); 7.18 (d, 1H); 7.3–7.64 (c, 6H); 7.75, 7.78, 7.81, 7.83 (m, 2H); 7.92 (d, 2H); 8.06 (s, 1H); 10.82 (s, 1H).

EXAMPLE 61

N-(Trans-7-chloro-5-(1-naphthyl)-1-neopentyl-2-oxo-1,2,3,5-tetrahydro-4,1-benzothiazepin-3-acetyl) methane sulfonamide To a stirred solution of 190 mg (0.41 mmol) trans-7-chloro-5-(1-naphthyl)-1-neopentyl-2-oxo-1,2,3,5-tetrahydro-4,1-benzothiazepin-3-acetic acid in 10 mL dichloromethane at room temperature was added 49 mg (0.52 mmol) methane sulfonamide, 63 mg (0.52 mmol) 4-dimethylaminopyridine and 213 mg (0.518 mmol) 1-cyclohexyl-3-(2-morpholinoethyl)carbodiimide metho-p-toluenesulfonate and the reaction mixture was stirred at room temperature overnight. Dichloromethane (20 ml) was added and the resulting solution was washed with 15 mL of 2N aqueous hydrochloric acid, dried over anhydrous sodium sulfate, filtered and concentrated in vacuo. The residue (200 mg) was chromatographed on 100 g silica gel, eluting with 9:1 ethyl acetate/methanol to yield 81 mg (37% yield) of the title compound as a white solid.

$^1$H NMR (CDCl$_3$) δ 1.08 (s, 9H); 2.6 (m, 1H); 3.02 (t, 1H); 3.2 (s, 3H); 3.4 (d, 1H); 3.91 (m, 1H); 4.5 (d, 1H); 6.6 (s, 1H); 6.78 (d, 1H); 7.25–7.61 (m, 5H); 7.91 (m, 4H).

EXAMPLE 62

N-[trans-7-chloro-5-(naphthalen-1-yl)-1-neopentyl-1,2,3,5-tetrahydro-2-oxo-4,1-benzoxazepine-3-acetyl]methyl sulfonamide The title compound was prepared in a manner analogous to that described in example 61 except 1-(3-dimethylaminopropyl)-3-ethylcarbodiimide hydrochloride was used as the carbodiimide.

68% yield.

MS (PCl): 547 (M+NH$_4^+$).

$^1$H NMR (250 MHz, (CD$_3$)$_2$SO) δ 8.05 (d, 2H), 7.84 (m, 2H), 7.68–7.43 (m, 5H), 6.46 (s, 1H), 6.27 (d, 1H), 4.47 (t, 1H), 4.35 (d, 1H), 3.75 (d, 1H), 3.22 (s, 3H), 2.86 (d, 2H), 0.97 (s, 9H).

EXAMPLE 63

Trans-7-chloro-5-(naphthalen-1-yl)-1-neopentyl-3-(1H-tetrazol-5-ylmethyl)-1,2,3,5-tetrahydro-4,1-benzothiazepin-2-one

EXAMPLE 63A

Trans-7-chloro-5-(naphthalen-1-yl)-1-neopentyl-1,2,3,5-tetrahydro-2-oxo-4,1-benzothiazepine-3-acetamide A solution of trans-7-chloro-5-(naphthalen-1-yl)-1-neopentyl-1,2,3,5-tetrahydro-2-oxo-4,1-benzothiazepine-3-acetic acid (200 mg, 426 μmol), 1,1'-carbonyldiimidazole (143 mg, 853 μmol) and tetrahydrofuran (5 mL) was heated at reflux for 1.5 hours. The resulting reaction mixture was cooled to 0° C. and a solution of tetrahydrofuran saturated with anhydrous ammonia (5 mL) was added. After 0.5 hours the reaction mixture was warmed to ambient temperature, concentrated under reduced pressure and purified by flash column chromatography (1:1 hexanes/ethyl acetate) to provide 200 mg (quantitative) of the title compound as a white powder.

MS (PCl): 467 (M+H$^+$).

$^1$H NMR (300 MHz, CDCl$_3$) δ 7.96 (m, 4H), 7.60 (t, 1H), 7.52–7.29 (m, 4H), 6.79 (d, 1H), 6.62 (s, 1H), 5.80 (br s, 1H), 5.34 (br s, 1H), 4.48 (d, 1H), 3.94 (dd, 1H), 3.39 (d, 1H), 2.98 (dd, 1H), 2.40 (dd, 1H), 1.10 (s, 9H).

EXAMPLE 63B

Trans-7-chloro-5-(naphthalen-1-yl)-1-neopentyl-1,2,3,5-tetrahydro-2-oxo-4,1-benzothiazepine-3-acetonitrile Trifluoroacetic anhydride (441 mg, 210 mmol, 296 μL) was added to a solution of trans-7-chloro-5-(naphthalen-1-yl)-1-neopentyl-1,2,3,5-tetrahydro-2-oxo-4,1-benzothiazepine-3-acetamide (98 mg, 210 μmol) and pyridine (2.1 mL) at 0° C. After 1.5 h, the reaction mixture was diluted with ether, washed with water (2x) and 0.5 N aqueous hydrochloric acid, dried over anhydrous sodium sulfate, concentrated under reduced pressure and purified by flash column chromatography (methylene chloride) to give 88 mg (93%) of the title compound as a white solid.

MS (PCl): 449 (M+H$^+$).

$^1$H NMR (250 MHz, CDCl$_3$) δ 7.98 (m, 4H), 7.64–7.26 (m, 5H), 6.83 (s, 1H), 6.07 (s, 1H), 4.52 (d, 1H), 3.72 (t, 1H), 3.40 (d, 1H), 3.03 (dd, 1H), 2.71 (dd, 1H), 1.12 (s, 9H).

EXAMPLE 63C

Trans-7-chloro-5-(naphthalen-1-yl)-1-neopentyl-3-(1H-tetrazol-5-ylmethyl)-1,2,3,5-tetrahydro-4,1-benzothiazepin-2-one A heterogeneous mixture of trans-7-chloro-5-(naphthalen-1-yl)-1-neopentyl-1,2,3,5-tetrahydro-2-oxo-4,1-benzothiazepine-3-acetonitrile (75 mg, 167 μmol), trimethyltin azide (70 mg, 334 μmol) and toluene (2 mL) was heated at reflux for 18 hours. Reaction mixture concentrated under reduced pressure and purified by flash column chromatography (80:15:1 chloroform/methanol/ammonium hydroxide) to yield a clear oil which was taken up in ethyl acetate, washed with 0.5 N hydrochloric acid, dried over anhydrous sodium sulfate and concentrated under reduced pressure to provide 58.5 mg (71 %) of the title compound as a white powder.

MS (PCl): 492 (M+H$^+$).

$^1$H NMR (250 MHz, CDCl$_3$) δ 7.93 (m, 4H), 7.61–7.29 (m, SH), 6.81 (s, 1H), 6.60 (s, 1H), 4.48 (d, 1H), 3.98 (dd, 1H), 3.64 (dd, 1H), 3.34 (m, 2H), 1.10 (s, 9H).

EXAMPLE 64

Trans-7-chloro-5-(naphthalen-1-yl)-1-neopentyl-3-{2-oxo-2-[4-(1H-tetrazol-5-yl)-piperidin-1-yl]-ethyl}-1,2,3,5-tetrahydro-4,1-benzothiazepin-2-one Prepared as described in example 63. From N-[trans-7-chloro-5-(naphthalen-1-yl)-1-neopentyl-1,2,3,5-tetrahydro-2-oxo-4,1-benzothiazepine-3-acetyl]isonipecotic acid.

60% yield.

$^1$H NMR (250 MHz, DMSO-d$_6$) δ 6.58 (d, 1H), 6.49 (s, 1H), 1.02 (s, 9H).

EXAMPLE 65

4'-Trifluoromethyl-2,2-dimethylpropionanilide

To a stirred solution of 4-trifluoromethylaniline (25 g, 0.155 mol) and pyridine (62 ml, 0.775 mol) in dichloromethane (300 ml) cooled to 0° C. under nitrogen was added dropwise pivaloyl chloride (19 ml, 0.155 mol). The reaction mixture was stirred at room temperature for 3.5 hr, then diluted with dichloromethane (300 ml). The resulting solution was washed sequentially with 1N aqueous hydrochloric acid solution (2×), saturated aqueous sodium bicarbonate solution, water and brine, dried (anhydrous sodium sulfate)and concentrated in vacuo to yield the title compound as a white solid (37 g, 97% yield).

$^1$H NMR (250 MHz, CDCl$_3$) δ 1.33 (s, 9H); 7.74 (b, 1H); 7.57 (d, 2H); 7.67 (d, 2H).

EXAMPLE 66

2'-[α-Hydroxy-(1-naphthyl)methyl]-4'-trifluoromethyl-2,2-dimethylpropionanilide

To a stirred solution of 4'-trifluoromethyl-2,2-dimethylpropionanilide (37 g, 0.15 mol) in anhydrous tetrahydrofuran (400 ml) cooled to 0° C. under nitrogen was added slowly a solution of n-butyllithium (160 mL of 2.5M solution in hexane, 0.4 mol). The reaction mixture was stirred at 0° C. for 2 hr, then a solution of 1-naphthaldehyde (40.7 ml, 0.3 mol) in tetrahydrofuran (50 ml) was slowly added. The resulting solution was stirred at room temperature overnight, quenched with water, diluted with ethyl acetate and separated. The aqueous phase was extracted with ethyl acetate (2×) and the combined ethyl acetate extracts were washed with water and brine, dried (anhydrous sodium sulfate) and concentrated. in vacuo to an oil (74 g). The crude product was chromatographed on 2 kg silica gel, eluting with 8:2 hexane/ethyl acetate to yield the title compound as a tan solid (31 g, 52% yield).

$^1$H NMR (250 MHz, CDCl$_3$) δ 1.12 (s, 9H); 3.05 (d, 1H); 6.65 (d, 1H); 7.33 (d, 1H); 7.45 (t, 1H); 7.56 (c, 3H); 7.92 (c, 2H); 8.04 (q, 1H); 8.4 (d, 1H); 9.11 (b, 1H).

EXAMPLE 67

[2-Neopentylamino)-5-trifluoromethylphenyl]-(1-naphthyl)methanol

To a stirred solution of 2-[α-hydroxy-(1-naphthyl)methyl] 4-trifluoromethyl-2,2-dimethylpropioanilide (5 g, 12.5 mmol) in anhydrous tetrahydrofuran (50 ml) under nitrogen was slowly added borane-tetrahydrofuran complex (12.5 mL of a 1.0M solution in tetrahydrofuran, 12.5 mmol). The reaction mixture was stirred at room temperature for 1 hr, then heated at reflux for 1.5 hr. Additional borane-tetrahydrofuran complex (12.5 mL of a 1.0M solution in tetrahydrofuran, 12.5 mmol) was added at room temperature and the resulting solution was heated at reflux for 1 hr. The reaction mixture was then cooled to room temperature, 2 mL methanol was added and after 5 minutes the solution was acidified with 2N aqueous hydrochloric acid solution. After 10 minutes the solution was basified with aqueous ammonium hydroxide solution, diluted with water and extracted with ethyl acetate (3×). The ethyl acetate extracts were washed sequentially with water and brine, dried (anhydrous sodium sulfate) and concentrated in vacuo to an oil. The crude product was chromatographed on silica gel, eluting with 85:15 hexane/ethyl acetate to yield the title compound as a white solid (2.4 g, 50% yield).

$^1$H NMR (250 MHz, CDCl$_3$) δ 0.81 (S, 9H); 2.36 (d, 1H); 2.89 (d, 2H); 4.81 (b, 1H); 6.56 (d, 1H); 6.72 (d,1H); 7.29 (d, 1H); 7.42–7.57 (c, 5H); 7.9 (c, 2H); 8.08 (m, 1H).

It should be understood that the invention is not limited to the particular embodiments shown and described herein, but that various changes and modifications may be made without departing from the spirit and scope of this novel concept as defined by the following claims.

We claim:

1. A compound of Formula I

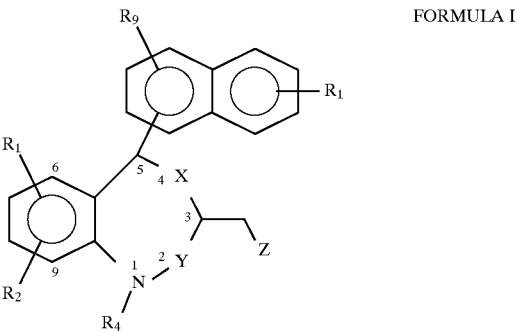

FORMULA I and the pharmaceutically acceptable cationic and anionic salts, prodrugs and stereoisomers thereof wherein X is oxy, thio,—S(O)— or —S(O)$_2$—;

Y is carbonyl or methylene;

R$_1$, R$_2$, R$_3$ and R$_9$ are each independently hydrogen, halo, hydroxyl, trifluoromethyl, (C$_1$–C$_4$)alkyl, fluorinated (C$_1$–C$_4$)alkyl having from 1 to 9 fluorines, (C$_1$–C$_4$) alkoxy, fluorinated (C$_1$–C$_4$)alkoxy having from 1 to 9 fluorines, (C$_1$–C$_4$)alkylthio, (C$_1$–C$_4$)alkylsulfinyl, (C$_1$–C$_4$)alkylsulfonyl, phenyl, amino, morio-N- or di-N,N-(C$_1$–C$_4$)alkylamino, carboxyl, (C$_1$–C$_4$) alkoxycarbonyl, carbamoyl, mono-N- or di-N,N-(C$_1$–C$_4$)alkylcarbamoyl, (C$_1$–C$_4$)alkanoylamino, fluorinated (C$_1$–C$_4$)alkanoylamino having from 1 to 9 fluorines, (C$_1$–C$_4$)alkylsulfonylamino or fluorinated (C$_1$–C$_4$)alkylsulfonylamino having from 1 to 9 fluorines, (C$_1$–C$_6$)alkanoyl, (C$_1$–C$_6$)alkanoyl(C$_1$–C$_6$)

alkyl, oxazolyl, thiazolyl, isoxazolyl, pyrazolyl or isothiazolyl wherein said preceding heterocycles are carbon linked and wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

$R_4$ is $(C_1-C_7)$alkyl or $(C_3-C_4)$cycloalkylmethyl;

Z is carboxyl, $(C_1-C_4)$alkoxycarbonyl, aminocarbonyl, cyano, hydroxyarninocarbonyl, —C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4-yl-aminocarbonyl,

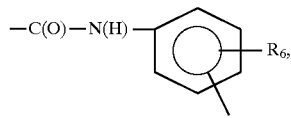

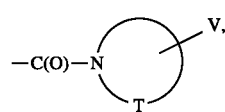

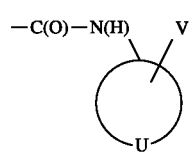

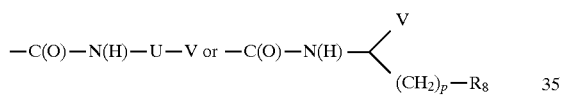

$R_5$ is amino or mono-N- or di-N,N-$(C_1-C_4)$alkylamino; $(C_1-C_4)$alkyl optionally substituted with 1 to 9 fluorines, amino, mono-N- or di-N,N-$(C_1-C_4)$alkylamino, carboxyl, $(C_1-C_4)$alkoxycarbonyl, carbamoyl or mono-N- or di-N,N-$(C_1-C_4)$alkylcarbamoyl; phenyl optionally mono- or di-substituted independently with methyl, methoxyl, fluoro, trifluoromethoxyl, carboxyl, $(C_1-C_4)$alkoxycarbonyl, methylthio, methylsulfinyl, methylsulfonyl, $(C_1-C_4)$alkylsulfonylamino or mono-N- or di-N,N-$(C_1-C_4)$alkylaminosulfonyl; or thiazolyl, isothiazolyl, thienyl, furyl, pyridinyl or such heterocycles optionally mono-substituted by carboxyl, or mono- or di-substituted with methyl;

$R_6$ is hydrogen, hydroxyl or methoxyl;

T forms a five to seven membered mono-aza, saturated ring, said ring optionally containing thia and said ring optionally mono-substituted on carbon with hydroxyl;

U forms a three to seven membered saturated carbocyclic ring;

V is —CO$_2$R$_7$, aminocarbonyl, cyano, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl; $R_7$ is hydrogen or $(C_1-C_4)$alkyl;

p is 1, 2, 3 or 4;

$R_8$ is hydroxyl, thiol, carboxyl, $(C_1-C_4)$alkoxycarbonyl, carbamoyl, amino, sulfamoyl, $(C_1-C_4)$alkoxy, fluorinated $(C_1-C_4)$alkoxy having from 1 to 9 fluorines, $(C_1-C_4)$alkylthio, $(C_1-C_4)$alkylsulfonyl, $(C_1-C_4)$alkylsulfinyl, mono-N- or di-N,N-$(C_1-C_4)$alkylcarbamoyl, mono-N- or di-N,N-$(C_1-C_4)$alkylamino, $(C_1-C_4)$alkylsulfonylamino, fluorinated $(C_1-C_4)$alkylsulfonylamino having from 1 to 9 fluorines, $(C_1-C_4)$alkanoylamino, fluorinated $(C_1-C_4)$alkanoylamino having from 1 to 9 fluorines, mono-N- or di-N,N-$(C_1-C_4)$alkylaminosulfonyl, ureido, mono-N- or di-N,N-$(C_1-C_4)$ureido, imidazolyl or pyridyl; and W is pyridyl, pyrimidyl, 1,3,4-oxadiazolyl, 1,3,4-thiadiazolyl, thiazolyl, 1,3,4-triazolyl or oxazolyl.

2. A compound as recited in claim 1 wherein $R_1$, $R_2$, $R_3$ and $R_9$ are each independently hydrogen, halo, hydroxyl, trifluoromethyl, $(C_1-C_4)$alkyl, fluorinated $(C_1-C_4)$alkyl having from 1 to 9 fluorines, $(C_1-C_4)$alkoxy, fluorinated $(C_1-C_4)$alkoxy having from 1 to 9 fluorines, $(C_1-C_4)$alkylthio, $(C_1-C_4)$alkylsulfinyl, $(C_1-C_4)$alkylsulfonyl, phenyl, amino, mono-N- or di-N,N-$(C_1-C_4)$alkylamino, carboxyl, $(C_1-C_4)$alkoxycarbonyl, carbamoyl, mono-N- or di-N,N-$(C_1-C_4)$alkylcarbamoyl, $(C_1-C_4)$alkanoylamino, fluorinated $(C_1-C_4)$alkanoylamino having from 1 to 9 fluorines, $(C_1-C_4)$alkylsulfonylamino or fluorinated $(C_1-C_4)$alkylsulfonylamino having from 1 to 9 fluorines, wherein $R_1$ and $R_2$ can be taken together to form a five, six or seven membered carbocyclic ring or can be taken together to form methylenedioxyl, ethylenedioxyl or propylenedioxyl and such rings formed by taking $R_1$ and $R_2$ together are fused at the 7 and 8 positions;

Z is carboxyl, $(C_1-C_4)$alkoxycarbonyl, hydroxyaminocarbonyl, -C(O)N(H)SO$_2$R$_5$, tetrazol-5-yl, 4,5-dihydro-5-oxo-1,2,4-oxadiazol-3-yl, tetrazol-5-yl-aminocarbonyl, 3-oxoisoxazolidin-4yl-aminocarbonyl,

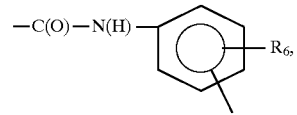

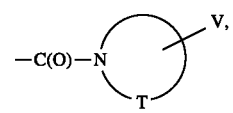

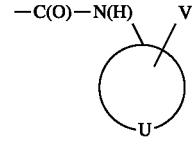

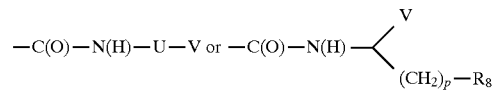

T forms a five to seven membered mono-aza, saturated ring optionally substituted with hydroxyl; and V is —CO$_2$R$_7$, tetrazol-5-yl, 4,5-dihydro-5-oxo-1,2,4-oxadiazol-3-yl, tetrazol-5-yl-aminocarbonyl or 3-oxoisoxazolidin-4-yl-aminocarbonyl.

3. A compound as recited in claim 2 wherein the $C^3$ and $C^5$ substituents are trans;

$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;

$R_3$ and $R_9$ are H;

X is oxy;

Y is carbonyl;

V is $-CO_2R_7$; and

Z is carboxyl, tetrazol-5-yl,

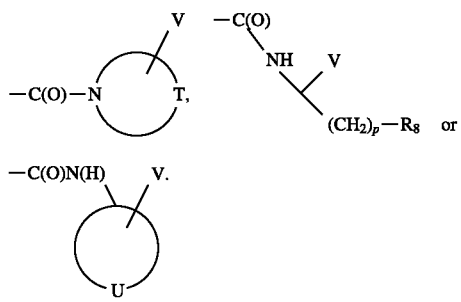

4. A compound as recited in claim 3 wherein $R_1$ and $R_2$ are each independently hydrogen, halo, $(C_1-C_4)$alkyl, $(C_1-C_4)$alkoxy, hydroxy or trifluoromethyl; and Z is carboxyl,

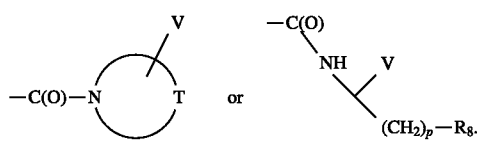

5. A compound as recited in claim 4 wherein

T forms a piperidin-1-yl ring; and $R_8$ is carboxyl or alkylthio.

6. The compound as recited in claim 5 wherein $R_4$ is neopentyl;

$R_1$ is 7-chloro;

$R_2$ is H; and

Z is carboxyl.

7. The compound as recited in claim 6 wherein the stereoisomer is (−)-trans-7-chloro-5-(1-naphthyl)-1-neopentyl-2-oxo-1,2,3,5-tetrahydro-4,1-benzoxazepin-3-acetic acid.

8. The compound as recited in claim 5 wherein $R_4$ is neopentyl;

$R_1$ is 7-chloro;

$R_2$ is H; and

Z is 4-carboxylpiperidin-1-yl-carbonyl.

9. The compound as recited in claim 8 wherein the stereoisomer is (−)-N-(trans-7-chloro-5-(1-naphthyl)-1-neopentyl-2-oxo-1,2,3,5-tetrahydro-4,1-benzoxazepin-3-acetyl)-isonipecotic acid.

10. The compound as recited in claim 5 wherein $R_4$ is neopentyl;

$R_1$ is 7-chloro;

$R_2$ is H; and

Z is 3-carboxylpiperidin-1-yl-carbonyl.

11. The compound as recited in claim 10 wherein the stereoisomer is (−)-N-(trans-7-chloro-5-(1-naphthyl)-1-neopentyl-2-oxo-1,2,3,5-tetrahydro-4,1-benzoxazepin-3-acetyl)-nipecotic acid.

12. The compound as recited in claim 11 wherein said compound is (−)-N-[trans-7-chloro-5-(1-naphthyl)-1-neopentyl-2-oxo-1,2,3,5-tetrahydro-4,1-benzoxazepin-3-acetyl]-(−)-nipecotic acid.

13. The compound as recited in claim 5 wherein $R_4$ is neopentyl;

$R_1$ is 7-chloro;

$R_2$ is H;

V is $-CO_2R_7$;

Z is

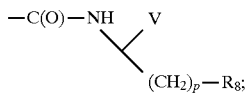

$R_7$ is methyl;

$R_8$ is carboxyl; and p is 1.

14. The compound as recited in claim 13 wherein the stereoisomer is (−)-N-(trans-7-chloro-5-(1-naphthyl)-1-neopentyl-2-oxo-1,2,3,5-tetrahydro-4,1-benzoxazepin-3-acetyl)-L-aspartic acid-α-methyl ester.

15. The compound as recited in claim 5 wherein $R_4$ is neopentyl;

$R_1$ is 7-chloro;

$R_2$ is H;

V is $-CO_2R_7$;

Z is

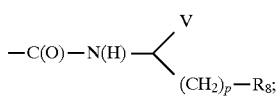

$R_7$ is methyl;

$R_8$ is carboxyl; and p is 2.

16. The compound as recited in claim 15 wherein the stereoisomer is (−)-N-(trans-7-chloro-5-(1-naphthyl)-1-neopentyl-2-oxo-1,2,3,5-tetrahydro-4,1-benzoxazepin-3-acetyl)-L-glutamic-α-methyl ester.

17. The compound as recited in claim 5 wherein $R_4$ is neopentyl;

$R_1$ is 7-chloro;

$R_2$ is H; and

V is $-CO_2R_7$;

Z is

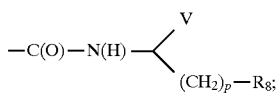

$R_7$ is H;

$R_8$ is thiomethyl; and p is 1.

18. The compound as recited in claim 17 wherein the stereoisomer is (−)-N-(trans-7-chloro-5-(1-naphthyl)-1-neopentyl-2-oxo-1,2,3,5-tetrahydro-4,1-benzoxazepin-3-acetyl)-L-S-methylcysteine.

19. The compound as recited in claim 5 wherein $R_4$ is neopentyl;
$R_1$ is 7-chloro;
$R_2$ is H; and
Z is 4-ethoxycarbonylpiperidin-1-yl-carbonyl.

20. The compound as recited in claim 19 wherein the stereoisomer is

Ethyl ester of (−)-N-trans-(7-chloro-5-(1-naphthyl)-1-neopentyl-2-oxo-1,2,3,5-tetrahydro-4,1-benzoxazepin-3-acetyl)-isonipecotic acid.

21. A compound as recited in claim 5 wherein said compound is

N-[trans-7-trifluoromethyl-5-(1-naphthyl)-1-neopentyl-2-oxo-1,2,3,5-tetrahydro-4,1-benzoxazepin-3-acetyl] isonipecotic acid;

N-[trans-7-trifluoromethyl-5-(1-naphthyl)-1-neopentyl-2-oxo-1,2,3,5-tetrahydro-4,1-benzoxazepin-3-acetyl] nipecotic acid;

N-[trans-7-trifluoromethyl-5-(1-naphthyl)-1-neopentyl-2-oxo-1,2,3,5-tetrahydro-4,1-benzoxazepin-3-acetyl]-L-proline;

trans-7-methyl-5-(naphthalen-1-yl)-1-neopentyl-1,2,3,5-tetrahydro-2-oxo-4,1-benzoxazepine-3-acetic acid;

N-[trans-7-methyl-5-(naphthalen-1-yl)-1-neopentyl-1,2,3,5-tetrahydro-2-oxo-4,1-benzoxazepine-3-acetyl] isonipecotic acid;

N-[trans-7-methyl-5-(naphthalen-1-yl)-1-neopentyl-1,2,3,5tetrahydro-2-oxo-4,1-benzoxazepine-3-acetyl] nipecotic acid;

trans-7-methoxy-5-(naphthalen-1-yl)-1-neopentyl-1,2,3,5-tetrahydro-2-oxo-4,1-benzoxazepine-3-acetic acid;

N-[trans-7-methoxy-5-(naphthalen-1-yl)-1-neopentyl-1,2,3,5-tetrahydro-2-oxo-4,1-benzoxazepine-3-acetyl] isonipecotic acid; or N-[trans-7-methoxy-5-(naphthaien-1-yl)-1-neopentyl-1,2,3,5-tetrahydro-2-oxo-4,1-benzoxazepine-3-acetyl] nipecotic acid.

22. A compound as recited in claim 5 wherein said compound is (−)-trans-7-trifluoromethyl-5-(1-naphthyl)-1-neopentyl-2-oxo-1,2,3,5-tetrahydro-4,1-benzoxazepin-3-acetic acid;

(−)-N-[trans-7-chloro-5-(1-naphthyl)-1-neopentyl-2-oxo-1,2,3,5-tetrahydro-4,1-benzoxazepin-3-acetyl]-L-pipecolinic acid; or (−)-N-[trans-7-chloro-5-(1-naphthyl)-1-neopentyl-2-oxo-1,2,3,5-tetrahydro-4,1-benzoxazepin-acetyl)-L-methionine.

23. A compound as recited in claim 3 wherein said compound is trans-7-methylthio-5-(1-naphthyl)-1-neopentyl-2-oxo-1,2,3,5-tetrahydro-4,1-benzoxazepin-4-acetic acid;

trans-7-trifluoromethoxy-5-(1-naphthyl)-1-neopentyl-2-oxo-1,2,3,5-tetrahydro-4,1-benzoxazepin-3-acetic acid;

trans-7,8-ethylenedioxy-5-(1-naphthyl)-1-neopentyl-2-oxo-1,2,3,5-tetrahydro-4,1-benzoxazepin-3-acetic acid;

N-[trans-7-chloro-5-(1-naphthyl)-1-neopentyl-2-oxo-1,2,3,5-tetrahydro-4,1-benzoxazepin-3-acetyl]-1-amino-1-cyclopentanecarboxylic acid;

N-[trans-7-chloro-5-(1-naphthyl)-1-neopentyl-2-oxo-1,2,3,5-tetrahydro-4,1-benzoxazepin-3-acety3l-1-amino-1-cyclopropanecarboxylic acid; or N-[trans-7-chloro-5-(1-naphthyl)-1-neopentyl-2-oxo-1,2,3,5-tetrahydro-4,1-benzoxazepin-3-acetyl]4-azetidinecarboxylic acid.

24. A compound as recited in claim 1 wherein T forms a 1,3-thiazolidine ring.

25. The compound as recited in claim 24 wherein said compound is (−)-N-[trans-7-chloro-5-(1-naphthyl)-1-neopentyl-2-oxo-1,2,3,5-tetrahydro-4,1-benzothiazepin-3-acetyl]-(R)-thiazolidinecarboxylic acid.

26. A compound as recited in claim 4 wherein

T forms a pyrrolidin-1-yl ring.

27. The compound as recited in claim 26 wherein $R_4$ is neopentyl;
$R_1$ is 7-chloro;
$R_2$ is H; and
Z is L-proline-N-carbonyl or D-proline-N-carbonyl.

28. The compound as recited in claim 27 wherein the compound is (−)-N-(trans-7-chloro-5-(1-naphthyl)-1-neopentyl-2-oxo-1,2,3,5-tetrahydro-4,1-benzoxazepin-3-acetyl)-L-proline.

29. The compound as recited in claim 27 wherein said compound is (−)-N-[trans-7-chloro-5-(1-naphthyl)-1-neopentyl-2-oxo-1,2,3,5-tetrahydro-4,1-benzoxazepin-3-acetyl]-D-proline.

30. A compound as recited in claim 2 wherein the $C^3$ and $C^5$ substituents are trans;
$R_1$ and $R_2$ are each independently hydrogen, halo, $(C_1–C_4)$alkyl, $(C_1–C_4)$alkoxy, hydroxy or trifluoromethyl;
$R_3$ and $R_9$ are H;
X is oxy;
Y is methylene;
V is —$CO_2R_7$; and
Z is carboxyl,

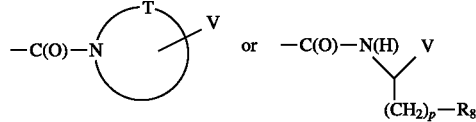

31. A compound as recited in claim 30 wherein

Z is

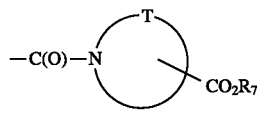

and T forms a piperidin-1-yl ring.

32. The compound as recited in claim 31 wherein $R_4$ is neopentyl;
$R_1$ is 7-chloro;
$R_2$ is H; and Z is 3-carboxylpiperidin-1-yl-carbonyl.

33. The compound as recited in claim 32 wherein the stereoisomer is
(−)-N-(trans-7-chloro-5-(1-naphthyl)-1-neopentyl-1,2,3,5-tetrahydro-4,1-benzoxazepin-3-acetyl)-nipecotic acid.

34. The compound as recited in claim 31 wherein
$R_4$ is neopentyl;
$R_1$ is 7-chloro;
$R_2$ is H; and
Z is 4-carboxylpiperidin-1-yl-carbonyl.

35. The compound as recited in claim 34 wherein the stereoisomer is
(−)-N-(trans-7-chloro-5-(1-naphthyl)-1-neopentyl-1,2,3,5-tetrahydro-4,1-enzoxazepin-3-acetyl)-isonipecotic acid.

36. A compound as recited in claim 2 wherein the $C^3$ and $C^5$ substituents are trans;
$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 fluorines, $(C_1-C_4)$alkanoyl or $R_1$ and $R_2$ taken together form an ethylenedioxy ring;
$R_3$ and $R_9$ are H;
X is thio;
Y is carbonyl;
V is $-CO_2R_7$ or tetrazol-5-yl; and
Z is carboxyl, tetrazol-5-yl,

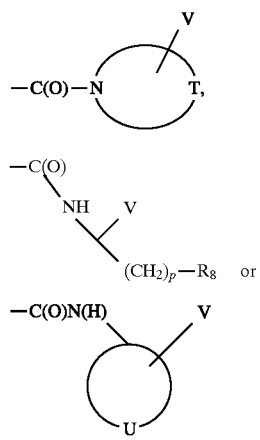

37. A compound as recited in claim 36 wherein
T forms a piperidin-1-yl ring.

38. A compound as recited in claim 37 wherein said compound is
trans-7-acetyl-5-(naphthalen-1-yl)-1-neopentyl-1,2,3,5-tetrahydro-2-oxo-4,1-benzothiazepine-3-acetic acid;
N-[trans-7-acetyl-5-(naphthalen-1-yl)-1-neopentyl-1,2,3,5-tetrahydro-2-oxo-4,1-benzothiazepine-3-acetyl] isonipecotic acid;
trans-7-chloro5(naphthalen-1-yl)-1-neopentyl-3-(1H-tetrazol-5-ylmethyl)-1,2,3,5-tetrahydro-4,1-benzothiazepin-2-one; or
trans-7-chloro-5-(naphthalen-1-yl)-1-neopentyl-3-{2-oxo-2-[4-(1H-tetrazol-5-yl)-piperidin-1-yl]-ethyl}-1,2,3,5-tetrahydro-4,1-benzothiazepin-2-one.

39. A compound as recited in claim 2 wherein the $C^3$ and $C^5$ substituents are trans;
$R_1$ and $R_2$ are each independently hydrogen, halo, $(C_1-C_4)$alkyl, $(C_1-C_4)$alkoxy, hydroxy or trifluoromethyl;
$R_3$ and $R_9$ are H;
X is thio;
Y is carbonyl;
V is $CO_2$-$R_7$; and
Z is carboxyl,

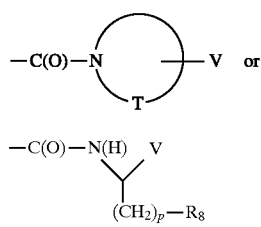

40. A compound as recited in claim 39 wherein
T forms a piperidin-1-yl ring.

41. A compound as recited in claim 40 wherein the compound is
trans-7-methyl-5-(naphthalen-1-yl)-1-neopentyl-1,2,3,5-tetrahydro-2-oxo-4,1-benzothiazepine-3-acetic acid;
N-[trans-7-methyl-5-(naphthalen-1-yl)-1-neopentyl-1,2,3,5-tetrahydro-2-oxo-4,1-benzothiazepine-3-acetyl] isonipecotic acid;
N-[trans-7-methyl-5-(naphthaien-1-yl)-1-neopentyl-1,2,3,5-tetrahydro-2-oxo-4,1-benzothiazepine-3-acetyl] nipecotic acid;
trans-7-methoxy-5-(naphthalen-1-yl)-1-neopentyl-1,2,3,5-tetrahydro-2-oxo-4,1-benzothiazepine-3-acetic acid; or
N-[trans-7-methoxy-5-(naphthalen-1-yl)-1-neopentyl-1,2,3,5-tetrahydro-2-oxo-4,1-benzothiazepine-3-acetyl] isonipecotic acid.

42. The compound as recited in claim 40 wherein
$R_4$ is neopentyl;
$R_1$ is 7-chloro;
$R_2$ is H; and
Z is 3-carboxylpiperidin-1-yl-carbonyl.

43. The compound as recited in claim 42 wherein the stereoisomer is
(−)-N-(trans-7-chloro-5-(1-naphthyl)-1-neopentyl-2-oxo-1,2,3,5-tetrahydro-4,1-benzothiazepin-3-acetyl)-nipecotic acid.

44. The compound as recited in claim 40 wherein
$R_4$ is neopentyl;
$R_1$ is 7-chloro;
$R_2$ is H; and
Z is 4-ethoxycarbonylpiperidin-1-yl-carbonyl.

45. The compound as recited in claim 44 wherein the stereoisomer is
Ethyl ester of (−)-N-(trans-7-chloro-5-(1-naphthyl)-1-neopentyl-2-oxo-1,2,3,5-tetrahydro-4,1-benzothiazepin-3-acetyl)isonipecotic acid.

46. The compound as recited in claim 40 wherein
$R_4$ is neopentyl;
$R_1$ is 7-chloro;
$R_2$ isH;and
Z is 4-carboxylpiperldin-1-yl-carbonyl.

47. The compound as recited in claim 46 wherein the stereoisomer is
(−)-N-(trans-7-chloro-5-(1-naphthyl)-1-neopentyl-2-oxo-1,2,3,5-tetrahydro-4,1-benzothiazepin-3-acetyl)-isonipecotic acid.

48. The compound as recited in claim 39 wherein
$R_4$ is neopentyl;
$R_1$ is 7-chloro;
$R_2$ is H; and
Z is carboxyl.

49. The compound as recited in claim 48 wherein the stereolsomer is
(−)-trans-7-chloro-5-(1-naphthyl)-1-neopentyl-2-oxo-1,2,3,5-tetrahydro-4,1-benzothiazepin-3-acetic acid.

50. The compound as recited in claim 49 wherein the compound is the (R)-α-methylbenzylammonium salt.

51. The compound as recited in claim 39 wherein
$R_4$ is neopentyl;
$R_1$ is 7-chloro;
$R_2$ is H;
V is —$CO_2R_7$;
Z is

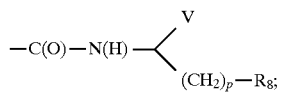

$R_7$ is methyl;
$R_1$ is carboxyl; and
p is 2.

52. The compound as recited in claim 51 wherein the stereoisomer is
(−)-N-(trans-7-chloro-5-(1-naphthyl)-1-neopentyl-2-oxo-1,2,3,5-tetrahydro-4,1-benzothiazepin-3-acetyl)-L-glutamic acid-α-methyl ester.

53. The compound as recited in claim 39 wherein
$R_4$ is neopentyl;
$R_1$ is 7-chloro;
$R_2$ is H;
V is —$CO_2R_7$;
Z is

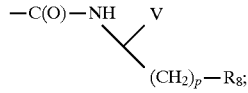

$R_7$ is methyl;
$R_8$ is carboxyl; and
p is 1.

54. The compound as recited in claim 53 wherein the stereoisomer is
(−)-N-(trans-7-chloro-5-(1-naphthyl)-1-neopentyl-2-oxo-1,2,3,5-tetrahydro-4,1-benzothiazepin-3-acetyl)-L-aspartic acid-α-methyl ester.

55. The compound as recited in claim 39 wherein
$R_4$ is neopentyl;
$R_1$ is 7-chloro;
$R_2$ is H;
V is —$CO_2R_7$;
Z is

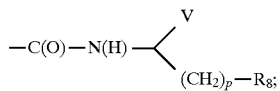

$R_7$ is H;
$R_8$ is thiomethyl; and
p is 1.

56. The compound as recited in claim 55 wherein the stereoisomer is
(−)-N-(trans-7-chloro-S-(1-naphthyl)-1-neopentyl-2-oxo-1,2,3,5-tetrahydro-4,1-benzothiazepin-3-acetyl)-L-S-methylcysteine.

57. A compound as recited in claim 39 wherein
T forms a pyrrolidin-1-yl ring.

58. A compound as recited in claim 57 wherein
$R_4$ is neopentyl;
$R_1$ is 7-chloro;
$R_2$ is H; and
Z is L-proline-N-carbonyl or D-proline-N carbonyl.

59. The compound as recited in claim 58 wherein the stereoisomer is
(−)-N-(trans-7-chloro-5-(1-naphthyl)-1-neopentyl-2-oxo-1,2,3,5-tetrahydro-4,1-benzothiazepin-3-acetyl)-L-proline.

60. The compound as recited in claim 58 wherein the compound is
(−)-N-[trans-7-chloro-5-(1-naphthyl)-1-neopentyl-2-oxo-1,2,3,5-tetrahydro-4,1-benzothiazepin-3-acetyl]-D-proline.

61. A compound as recited in claim 2 wherein
the $C^3$ and $C^5$ substituents are trans;
$R_1$ and $R_2$ are each independently hydrogen, halo, $(C_1-C_4)$alkyl, $(C_1-C_4)$alkoxy, hydroxy, trifluoromethyl, $(C_1-C_4)$alkylthio, fluorinated $(C_1-C_4)$ alkoxy having from 1 to 9 iluorines, $(C_1-C_4)$alkanoyl or $R_1$ and $R_2$ taken together form an ethylenedioxy ring;
$R_3$ is H;
$R_9$ is $(C_1-C_4)$alkoxy
X is oxy;
Y is carbonyl;
V is —$CO_2R_7$ or tetrazol-5-yl; and
Z is carboxyl, tetrazol-5-yl,

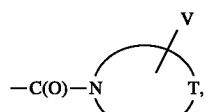

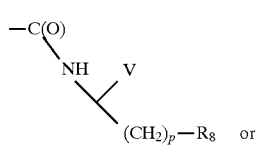 or

-continued

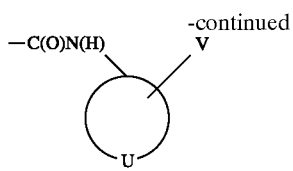
—C(O)N(H)—[ring with V top, U bottom]

62. A compound as recited in claim 61 wherein $R_1$ is 7-chloro;

$R_2$ is H;

$R_4$ is neopentyl;

$R_9$ is methoxy; and

T forms a piperidin-1-yl ring.

63. A compound as recited in claim 62 wherein the compound is trans-7-chloro-5-(4-methoxynaphthalen-1-yl)-1-neopentyl-1,2,3,5-tetrahydro-2-oxo-4,1-benzoxazepine-3-acetic acid;

N-[trans-7-chloro-5-(4-methoxynaphthalen-1-yl)-1-neopentyl-1,2,3,5-tetrahydro-2-oxo-4,1-benzoxazepine-3-acetyl]isonipecotic acid; or N-[trans-7-chloro-5-(4-methoxynaphthalen-1-yl)-1-neopentyl-1,2,3,5-tetrahydro-2-oxo-4,1-benzoxazepine-3-acetyl]nipecotic acid.

64. A method of treating hypercholesterolemia which comprises administering to a mammal in need of such treatment a hypercholesterolemic treating amount of a compound of claim 1.

65. A method of treating atherosclerosis which comprises administering to a mammal in need of such treatment a atherosclerosis treating amount of a compound of claim 1.

66. A method for the antifungal treatment of a mammal in need of such treatment which comprises administering to the mammal an antifungal treating effective amount of a compound of claim 1.

67. A method for the treatment of acne In a mammal in need of such treatment which comprises administering to the mammal an acne treating amount of a compound of claim 1.

* * * * *